(12) United States Patent
Ohuchi et al.

(10) Patent No.: US 10,053,499 B2
(45) Date of Patent: Aug. 21, 2018

(54) POLYPEPTIDE HAVING SIALYLATED SUGAR CHAINS ATTACHED THERETO

(71) Applicant: Glytech, Inc., Kyoto-shi, Kyoto (JP)

(72) Inventors: Masaki Ohuchi, Tokyo (JP); Mika Nishihara, Amagasaki (JP); Katsunari Tezuka, Kyoto (JP); Masatoshi Maeda, Tokyo (JP); Yasuhiro Kajihara, Toyonaka (JP); Izumi Sakamoto, Kyoto (JP)

(73) Assignee: GLYTECH, INC., Kyoto (JP)

( * ) Notice: Subject to any disclaimer, the term of this patent is extended or adjusted under 35 U.S.C. 154(b) by 0 days.

(21) Appl. No.: 14/780,133

(22) PCT Filed: Mar. 24, 2014

(86) PCT No.: PCT/JP2014/058127
§ 371 (c)(1),
(2) Date: Sep. 25, 2015

(87) PCT Pub. No.: WO2014/157107
PCT Pub. Date: Oct. 2, 2014

(65) Prior Publication Data
US 2016/0052987 A1    Feb. 25, 2016

(30) Foreign Application Priority Data

Mar. 29, 2013   (JP) ................. 2013-073703

(51) Int. Cl.
*C07K 14/565* (2006.01)
*A61K 38/00* (2006.01)

(52) U.S. Cl.
CPC ............ *C07K 14/565* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,514,729 B1 | 2/2003 | Bentzien | |
| 6,572,853 B1 | 6/2003 | Schneider-Fresenius et al. | |
| 7,446,173 B2 | 11/2008 | Pepinsky et al. | |
| 7,700,314 B2 | 4/2010 | El-Tayar et al. | |
| 7,829,659 B2 | 11/2010 | Grabstein et al. | |
| 7,985,731 B2 * | 7/2011 | Kajihara .............. | C07K 14/605 514/20.9 |
| 2002/0119516 A1 | 8/2002 | Paulson et al. | |
| 2002/0160460 A1 | 10/2002 | Paulson et al. | |
| 2003/0124645 A1 | 7/2003 | Paulson et al. | |
| 2004/0115168 A1 | 6/2004 | Defrees et al. | |
| 2004/0137581 A1 | 7/2004 | Aguinaldo et al. | |
| 2005/0221344 A1 | 10/2005 | Welcher et al. | |
| 2006/0040353 A1 | 2/2006 | Davidson et al. | |
| 2008/0003202 A1 * | 1/2008 | Guyon ................ | C07K 14/565 424/85.6 |
| 2009/0043076 A1 | 2/2009 | Carr et al. | |
| 2009/0214472 A1 | 8/2009 | Filpula et al. | |
| 2010/0003721 A1 | 1/2010 | Shin et al. | |
| 2010/0145017 A1 | 6/2010 | Narumi et al. | |
| 2011/0172392 A1 | 7/2011 | Kajihara et al. | |
| 2011/0195897 A1 | 8/2011 | Kajihara et al. | |
| 2011/0262945 A1 | 10/2011 | Kajihara et al. | |
| 2014/0058062 A1 | 2/2014 | Kajihara et al. | |
| 2014/0148585 A1 | 5/2014 | Sugihara et al. | |

FOREIGN PATENT DOCUMENTS

| | | |
|---|---|---|
| EP | 237019 A2 | 9/1987 |
| EP | 2330114 A1 | 6/2011 |
| JP | 63-267296 | 11/1988 |
| JP | 2002-543790 | 12/2002 |
| JP | 2002-543790 A | 12/2002 |
| JP | 2008-518631 A | 6/2008 |
| JP | 2009242372 | 10/2009 |
| JP | 2011-024597 A | 2/2011 |
| JP | 2011-24597 A | 2/2011 |
| RU | 2007103479 | 9/2008 |
| RU | 2014116550 | 10/2015 |
| WO | WO 00/23472 | 4/2000 |
| WO | WO 02/20033 A1 | 3/2002 |
| WO | WO 2002/074806 A2 | 9/2002 |
| WO | WO 03/075944 | 9/2003 |
| WO | WO 2004/020468 A2 | 3/2004 |
| WO | WO 2005/019260 A1 | 3/2005 |
| WO | WO 2006/020580 | 2/2006 |
| WO | WO 2007/110231 | 10/2007 |
| WO | 2009/017154 | 2/2009 |
| WO | WO 2009/017154 | 2/2009 |
| WO | WO 2009/153960 A1 | 12/2009 |
| WO | 2010/021126 | 2/2010 |
| WO | WO 2010/015722 | 2/2010 |
| WO | WO 2010/021126 A1 | 2/2010 |
| WO | WO 2012/051615 A1 | 4/2012 |
| WO | WO 2012/121206 A1 | 9/2012 |
| WO | WO 2013/002330 A1 | 1/2013 |

OTHER PUBLICATIONS

Kolchanov, 1988, Journal of Molecular Evolution, vol. 27, pp. 154-162.*

(Continued)

*Primary Examiner* — Daniel E Kolker
*Assistant Examiner* — Jegatheesan Seharaseyon
(74) *Attorney, Agent, or Firm* — Myers Bigel, P.A.

(57) ABSTRACT

The object of the present invention is to provide a polypeptide having interferon β activity glycosylated with highly uniform sialylated sugar chains. The present invention is a glycosylated polypeptide, wherein the polypeptide is any polypeptide selected from the group consisting of the following (1) to (4); (1) a polypeptide consisting of the amino acid sequence represented by SEQ ID NO. 1, (2) a polypeptide having one or a few amino acids deleted, substituted, or added in the polypeptide consisting of the amino acid sequence represented by SEQ ID NO. 1, (3) a polypeptide that is an analog of interferon β, and (4) a polypeptide having 80% or more homology to the polypeptide consisting of the amino acid sequence represented by SEQ ID NO. 1, in which amino acids at 4 to 6 locations are substituted with glycosylated amino acids, and wherein all of the non-reducing terminals of said sugar chain are sialylated.

6 Claims, 12 Drawing Sheets

(56) References Cited

OTHER PUBLICATIONS

Pasquo, 2012, PLoS ONE, vol. 7, Issue 2, e32555.*
Bork, 2000, Genome Research 10:398-400.*
Bork et al., 1996, Trends in Genetics 12:425-427.*
International Search Report corresponding to PCT/JP2014/058127; dated Jun. 10, 2014.
Sakamoto, I., et al., Chemical synthesis of homogeneous human glycosyl-interfereon that exhibits potent antitumor activity in vivo., 2012, Journal of the American Chemical Society, vol. 134, p. 5428-5431 Abstract, Figure 1, Figure 3.
Ishida et al., "Accelerated clearance of PEGylated liposomes in rats after repeated injections", *J. Control. Rel.*, 88, 2003. pp. 35-42.
Extended European Search Report corresponding to International Application No. PCT/JP2014058127, dated Sep. 28, 2016, 8 pages.
Extended European Search Report, EP 12836998 dated Apr. 7, 2015, 9 pages.
Gawlitzek et al. "Characterization of changes in the glycosylation pattern of recombinant proteins from BHK-21 cells due to different culture conditions", *J. Biotechnol.* vol. 42: pp. 117-131 (1995).
Greene T.W. et al, "Protective groups in organic synthesis", 2 edition, John Wiley & Sons, Inc, Canada, 1991, p. 473, line 293.
Gross, G. et al. Interferon-beta [synthetic construct]; Genbank accession AAA72975.1; Apr. 27, 1993.
Haselberg et al. "Capillary electrophoresis-mass spectrometry using noricovalently coated capillaries for the analysis of biopharmaceuticals", *Anal Bioanal Chem* vol. 400: pp. 295-303 (2011).
Imanishi, J. *Gan to Kagaku Ryoho* 21(16):2853-8 (1994) (abstract only).
International Search Report for PCT Application No. PCT/JP2012/075262, dated Nov. 13, 2012.
Karpusas "The structure of human interferon-β: implications for activity", *Cell. Mol. Life Sci.* 54: pp. 1203-1216 (1998).
Karpusas et al. "The crystal structure of human interferon-β at 2.2-Å resolution", *PNAS* 94: pp. 11813-11818 (1997).
Porter, A.G. et al., "Novel Modified β-Interferons: Gene Cloning, Expression, and Biological Activity in Bacterial Extracts", *DNA*, Novel β/a Hybrid Interferons, vol. 5, No. 2, (1986).
Revel, M. Structure, Differential Actions, and Medical Applications, In *Growth Factors and Cyokines in Health and Disease*, vol. 2B: pp. 433-520, JAI Press Inc (1997).
Russian Office Action corresponding to Russian Application No. 2007103479, dated Sep. 27, 2016, 7 pages.
Ruzicka et al. "Binding of recombinant-produced interferon beta ser to human lymphoblastoid cells", Evidence far two binding domains. *J Biological Chem.* 262: pp. 16142-16149 (1987).
Senda et al. "Three-dimensional crystal structure of recombinant murine interferon-β", *The EMBO J.* 11(9): pp. 3193-3201 (1992).
Wadler and Schwartz "New Advances in Interferon Therapy", *The Oncologist* 2:254-267 (1997).
Walsh et al. "Post-translational modifications in the context of therapeutic proteins", Nat. Bioteohnol., (2006), 24(10): 1241-1252.
Ghane, M. et. al., "Design Construction and Expression of a Synthetic βInterferon (IFN-B) Gene in *E. coli*", Pak. J. Biol. Sci., 9:2922-2926 (2006).
Runkle et al. "Systematic Mutational Mapping of Sites on Human Interferon-â-1a That are Important for Receptor Binding and Functonal Activity", Biochemistry, 39:2538-2551 (2000).
Pakula, Andrew "Genetic Analysis of Protein Stability and Function", Annu. Rev. Genet., 23:289-310 (1989).

* cited by examiner

[Figure 1]
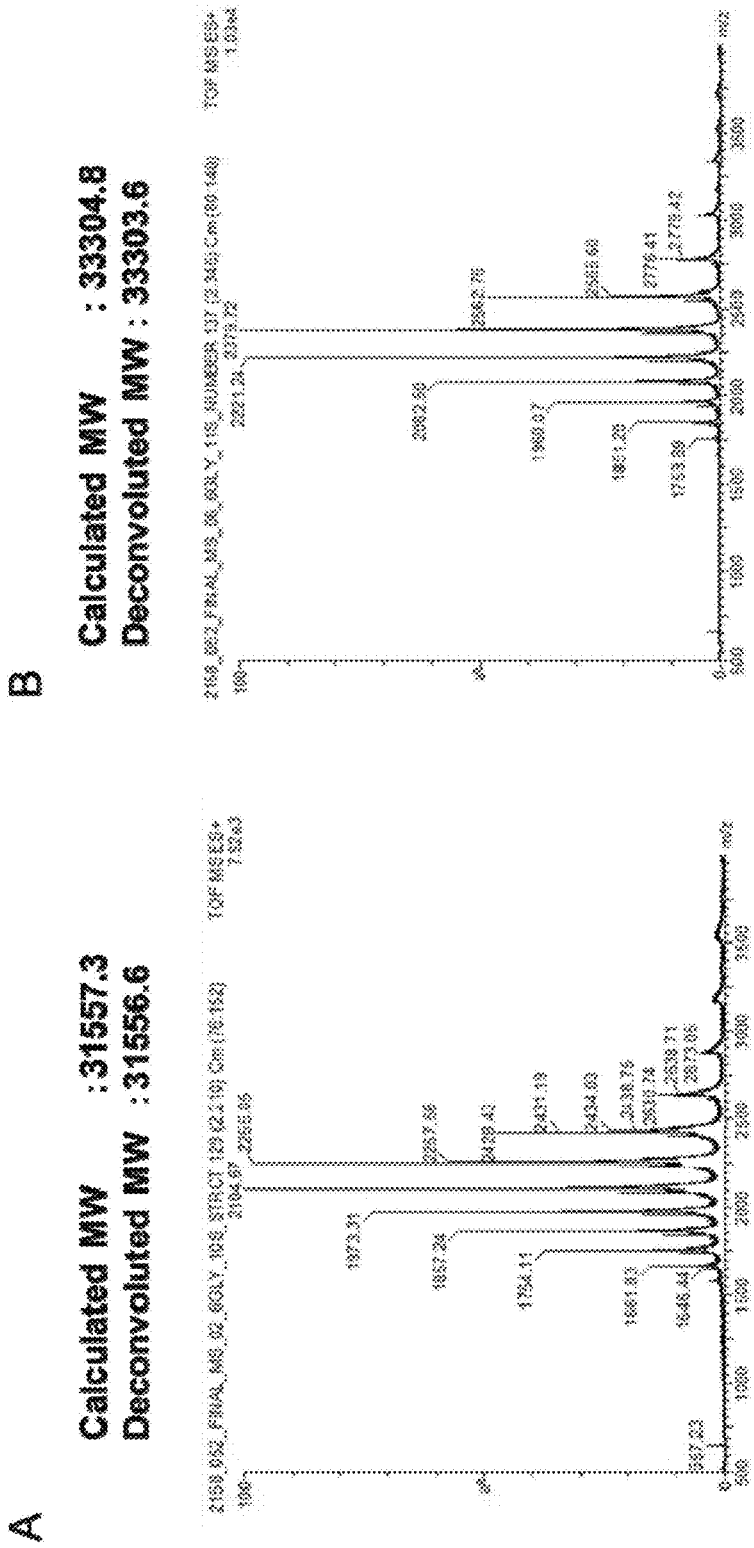
A: monoSialo (S1C-Q48C-N79C-K107C-R112C-R123C)
B: diSialo (S1C-Q48C-N79C-K107C-R112C-R123C)

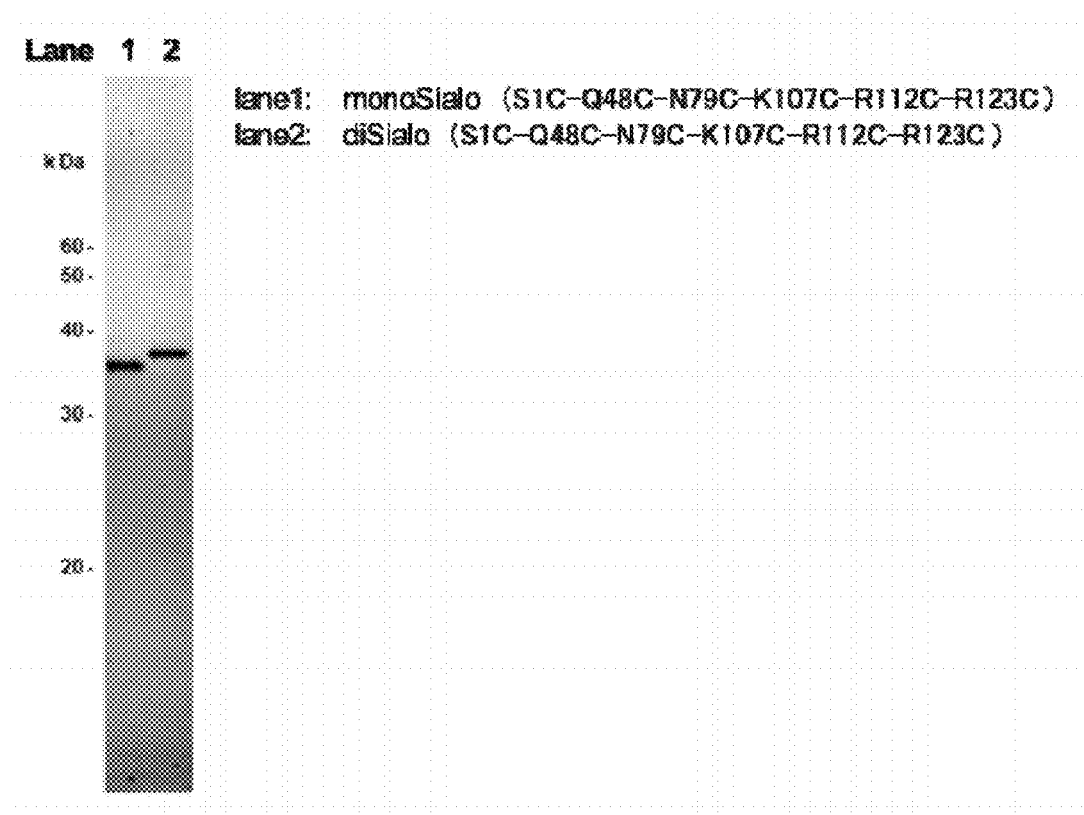
[Figure 2]
lane1: monoSialo (S1C-Q48C-N79C-K107C-R112C-R123C)
lane2: diSialo (S1C-Q48C-N79C-K107C-R112C-R123C)

[Figure 3]
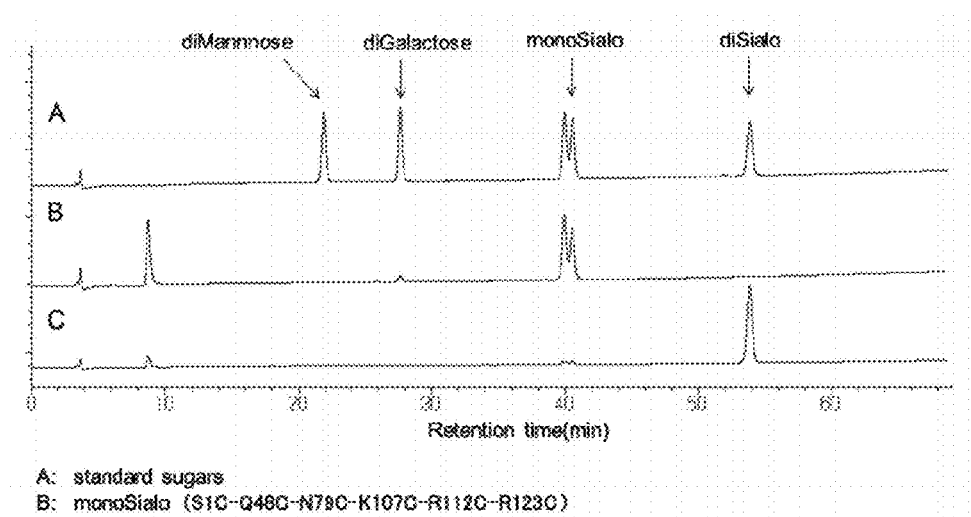
A: standard sugars
B: monoSialo (S1C-Q48C-N79C-K107C-R112C-R123C)
C: diSialo (S1C-Q48C-N79C-K107C-R112C-R123C)
[Figure 4]
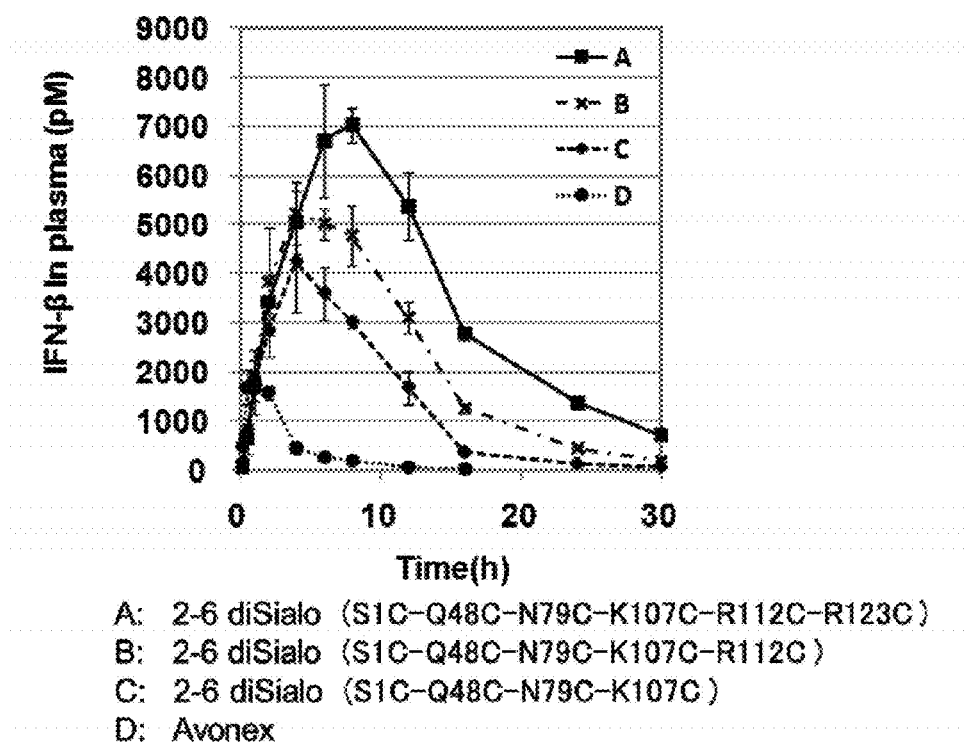
A: 2-6 diSialo (S1C-Q48C-N79C-K107C-R112C-R123C)
B: 2-6 diSialo (S1C-Q48C-N79C-K107C-R112C)
C: 2-6 diSialo (S1C-Q48C-N79C-K107C)
D: Avonex

[Figure 5]
| Multiply Sugar Chain-Modified Form | s.c. | | | | |
|---|---|---|---|---|---|
| | $t_{1/2}$ (h) | AUC∞ (h·pM) | MRT (h) | $C_{max}$ (pM) | $T_{max}$ (h) |
| A | 7.1 | 108351.3 | 13.0 | 7033.5 | 8.0 |
| B | 5.0 | 67000.1 | 9.5 | 5226.0 | 4.0 |
| C | 3.9 | 40608.2 | 7.5 | 4229.1 | 4.0 |
| D | 2.7 | 6876.8 | 3.3 | 1858.3 | 1.0 |
A: 2-6 diSialo (S1C-Q48C-N79C-K107C-R112C-R123C)
B: 2-6 diSialo (S1C-Q48C-N79C-K107C-R112C)
C: 2-6 diSialo (S1C-Q48C-N79C-K107C)
D: Avonex
[Figure 6]
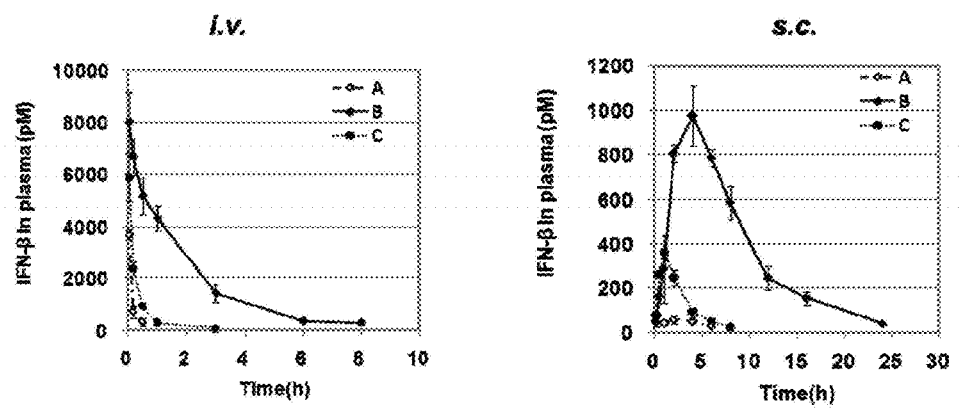
A: 2-6 monoSialo (S1C-Q48C-N79C-K107C)
B: 2-6 diSialo (S1C-Q48C-N79C-K107C)
C: Avonex

[Figure 7]
| 4-gly Sugar Substituted IFN β | i.v. | | | | s.c. | | | | | Bio-availability |
|---|---|---|---|---|---|---|---|---|---|---|
| | $t_{1/2}$ (h) | AUC∞ (h·pM) | MRT (h) | $C_0$ (pM) | $t_{1/2}$ (h) | AUC∞ (h·pM) | MRT (h) | $C_{max}$ (pM) | $T_{max}$ (h) | |
| A | 0.11 | 458.0 | 0.13 | 4245.8 | ND | 458.9 | ND | 57.7 | 2 | 1 |
| B | 2.58 | 11998.9 | 2.33 | 7454.4 | 4.2 | 9066.9 | 7.9 | 975.0 | 4 | 0.76 |
| C | 1.07 | 1589.3 | 0.71 | 5111.8 | 2.19 | 1155.5 | 3.03 | 361.2 | 1 | 0.74 |
A: 2-6 monoSialo (S1C-Q48C-N79C-K107C)
B: 2-6 diSialo (S1C-Q48C-N79C-K107C)
C: Avonex
[Figure 8]
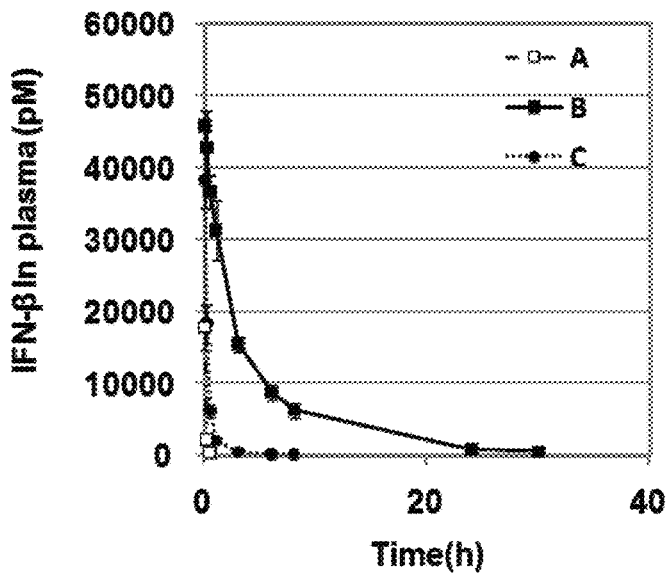
A: 2-6 monoSialo (S1C-Q48C-N79C-K107C-R112C-R123C)
B: 2-6 diSialo (S1C-Q48C-N79C-K107C-R112C-R123C)
C: Avonex

[Figure 9]
| 6-gly Sugar Substituted IFN β | i.v. | | | |
|---|---|---|---|---|
| | $t_{1/2}$ (h) | AUC∞ (h·pM) | MRT (h) | $C_0$ (pM) |
| A | 0.1 | 2092.3 | 0.1 | 29773.9 |
| B | 5.7 | 199219.3 | 5.8 | 46547.0 |
| C | 2.1 | 14536.2 | 1.0 | 46049.0 |
A: 2-6 monoSialo (S1C-Q48C-N79C-K107C-R112C-R123C)
B: 2-6 diSialo (S1C-Q48C-N79C-K107C-R112C-R123C)
C: Avonex
[Figure 10]
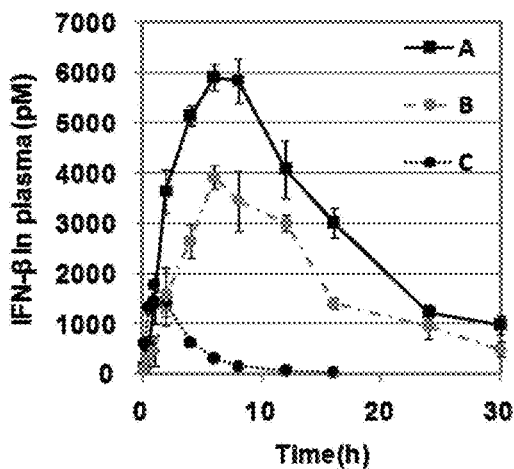
A: 2-6 diSialo (S1C-Q48C-N79C-K107C-R112C-R123C)
B: PEG20K (N terminus)
C: Avonex

[Figure 11]

| IFN β | s.c. | | | |
|---|---|---|---|---|
| | $t_{1/2}$ (h) | AUC∞ (h·pM) | MRT (h) | $C_0$ (pM) |
| A | 8.1 | 102479.3 | 14.3 | 5902.2 |
| B | 7.8 | 60421.7 | 14.4 | 3919.5 |
| C | 3.2 | 6816.8 | 3.5 | 1766.4 |

A: 2-6 diSialo (S1C-Q48C-N79C-K107C-R112C-R123C)
B: PEG20K (N terminus)
C: Avonex

[Figure 12]
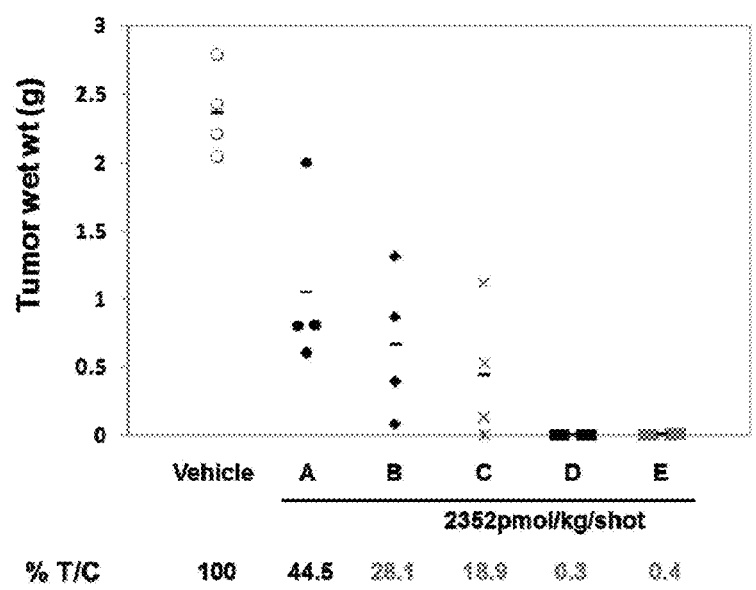
A: Avonex
B: 2-6 diSialo (S1C-Q48C-N79C-K107C)
C: 2-6 diSialo (S1C-Q48C-N79C-K107C-R112C)
D: 2-6 diSialo (S1C-Q48C-N79C-K107C-R112C-R123C)
E: 2-6 diSialo (S1C-N3C-Q48C-N79C-K107C-R112C)

[Figure 13]
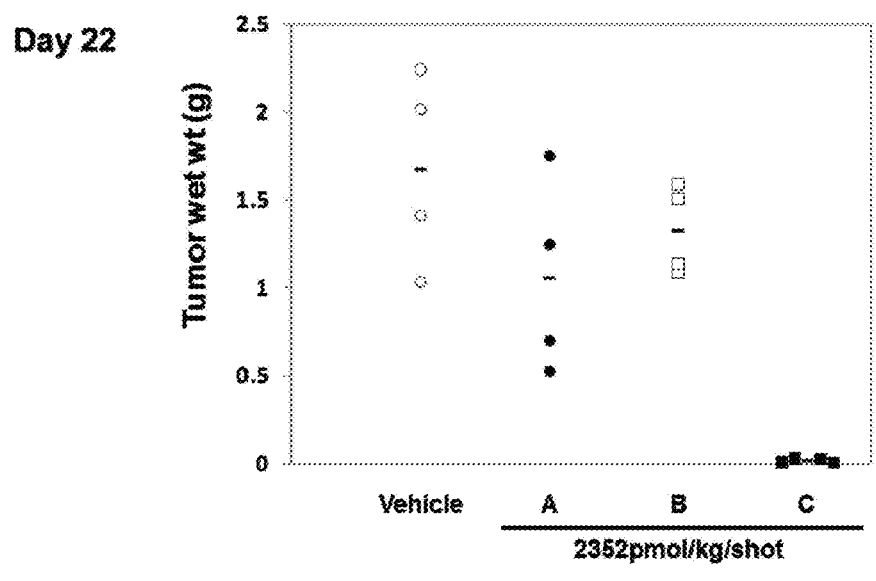
A: Avonex
B: 2-6 monoSialo (S1C-Q48C-N79C-K107C-R112C-R123C)
C: 2-6 diSialo (S1C-Q48C-N79C-K107C-R112C-R123C)

[Figure 14]
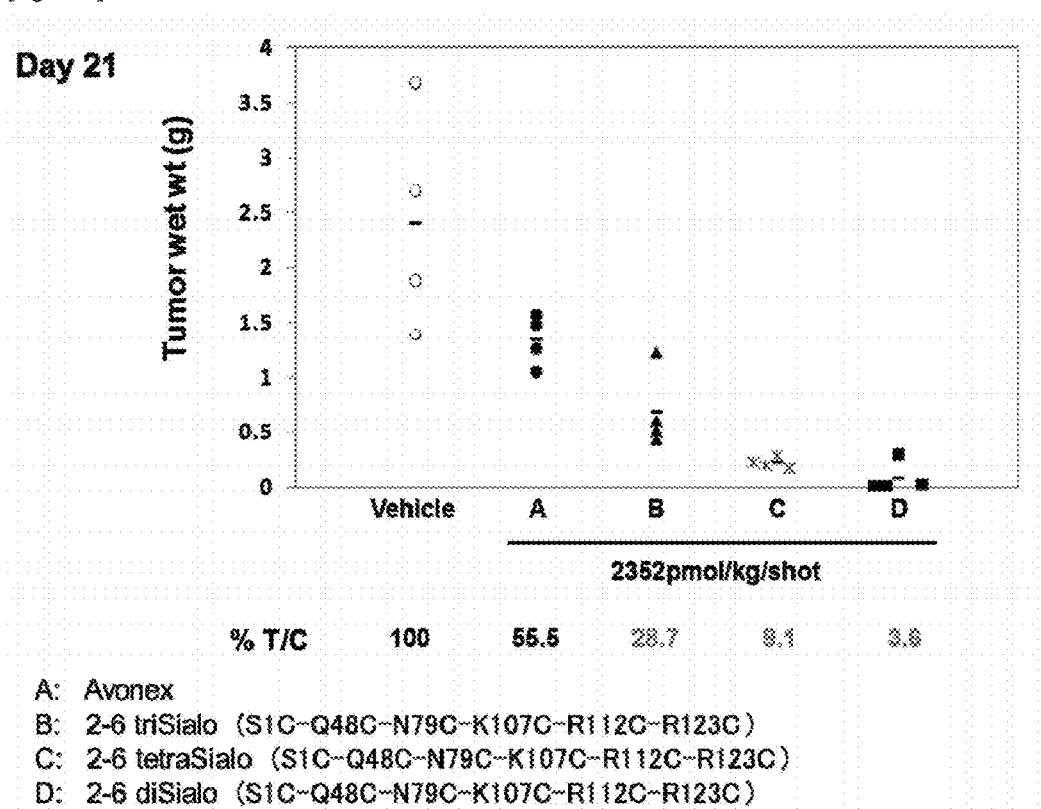
A: Avonex
B: 2-6 triSialo (S1C-Q48C-N79C-K107C-R112C-R123C)
C: 2-6 tetraSialo (S1C-Q48C-N79C-K107C-R112C-R123C)
D: 2-6 diSialo (S1C-Q48C-N79C-K107C-R112C-R123C)

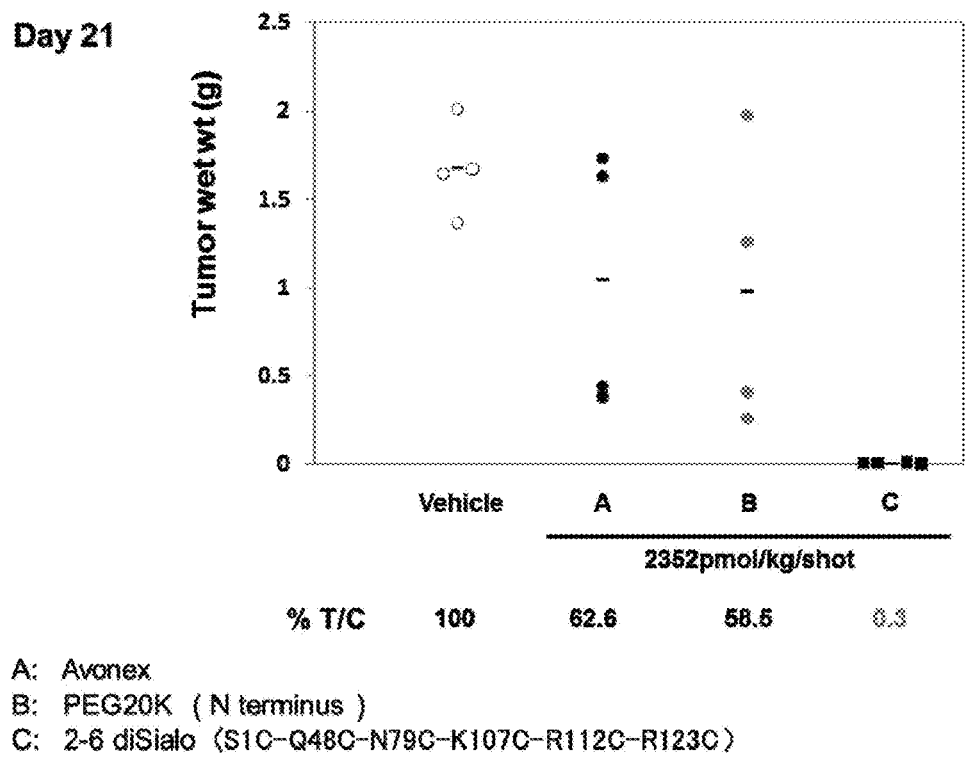
[Figure 15]
A: Avonex
B: PEG20K ( N terminus )
C: 2-6 diSialo (S1C-Q48C-N79C-K107C-R112C-R123C)

[Figure 16]

(SEQ ID NO. 1)

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
|Ser|Tyr|Asn|Leu|Leu|Gly|Phe|Leu|Gln|Arg|Ser|Ser|Asn|Phe|Gln|Ser|Gln|Lys|Leu|Leu|

| 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|
|Trp|Gln|Leu|Asn|Gly|Arg|Leu|Glu|Tyr|Cys|Leu|Lys|Asp|Arg|Met|Asn|Phe|Asp|Ile|Pro|

| 41 | 42 | 43 | 44 | 45 | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|---|---|---|
|Glu|Glu|Ile|Lys|Gln|Leu|Gln|Gln|Phe|Gln|Lys|Glu|Asp|Ala|Ala|Leu|Thr|Ile|Tyr|Glu|

| 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|
|Met|Leu|Gln|Asn|Ile|Phe|Ala|Ile|Phe|Arg|Gln|Asp|Ser|Ser|Ser|Thr|Gly|Trp|Asn|Glu|

| 81 | 82 | 83 | 84 | 85 | 86 | 87 | 88 | 89 | 90 | 91 | 92 | 93 | 94 | 95 | 96 | 97 | 98 | 99 | 100 |
|---|---|---|---|---|---|---|---|---|---|---|---|---|---|---|---|---|---|---|---|
|Thr|Ile|Val|Glu|Asn|Leu|Leu|Ala|Asn|Val|Tyr|His|Gln|Ile|Asn|His|Leu|Lys|Thr|Val|

| 101 | 102 | 103 | 104 | 105 | 106 | 107 | 108 | 109 | 110 | 111 | 112 | 113 | 114 | 115 | 116 | 117 | 118 | 119 | 120 |
|---|---|---|---|---|---|---|---|---|---|---|---|---|---|---|---|---|---|---|---|
|Leu|Glu|Glu|Lys|Leu|Glu|Lys|Glu|Asp|Phe|Thr|Arg|Gly|Lys|Leu|Met|Ser|Ser|Leu|His|

| 121 | 122 | 123 | 124 | 125 | 126 | 127 | 128 | 129 | 130 | 131 | 132 | 133 | 134 | 135 | 136 | 137 | 138 | 139 | 140 |
|---|---|---|---|---|---|---|---|---|---|---|---|---|---|---|---|---|---|---|---|
|Leu|Lys|Arg|Tyr|Tyr|Gly|Arg|Ile|Leu|His|Tyr|Leu|Lys|Ala|Lys|Glu|Tyr|Ser|His|Cys|

| 141 | 142 | 143 | 144 | 145 | 146 | 147 | 148 | 149 | 150 | 151 | 152 | 153 | 154 | 155 | 156 | 157 | 158 | 159 | 160 |
|---|---|---|---|---|---|---|---|---|---|---|---|---|---|---|---|---|---|---|---|
|Ala|Trp|Thr|Ile|Val|Arg|Val|Glu|Ile|Leu|Arg|Asn|Phe|Tyr|Phe|Ile|Asn|Arg|Leu|Thr|

| 161 | 162 | 163 | 164 | 165 |
|---|---|---|---|---|
|Gly|Tyr|Leu|Arg|Asn|

POLYPEPTIDE HAVING SIALYLATED SUGAR CHAINS ATTACHED THERETO

STATEMENT OF PRIORITY

This application is a 35 U.S.C. § 371 national phase application of International Application Serial No. PCT/JP2014/058127, filed Mar. 24, 2014, which claims the benefit, under 35 U.S.C. § 119 (a) of Japanese Patent Application No. 2013-073703, filed Mar. 29, 2013, the entire contents of each of which are incorporated by reference herein.

TECHNICAL FIELD

The present intention relates to a polypeptide glycosylated with a sialylated sugar chain. More specifically, the present invention relates to a polypeptide having interferon β activity glycosylated with highly uniform sialylated sugar chains.

BACKGROUND ART

Natural human interferon β (IFN-β) is a glycoprotein consisting of 166 amino acid residues. Interferon β belong to the cytokine family, and is known to be involved in the immunoregulatory action, the anti-viral activity, and the cell growth inhibitory action. The human interferon β also has three Cys at positions 17, 31, and 141 in the natural amino acid sequence, and has one complex N-linked oligosaccharide at Asn at position 80. It is also known to have a disulfide bond at Cys at positions 31 and 141.

Interferon β as a pharmaceutical is manufactured by utilizing a cell expression system, and is classified into IFN-β-1a or IFN-β-1b depending on the difference in the host for expression. IFN-β-1a is an expression system employing Chinese hamster ovary (CHO) cells, and is a glycoprotein having sugar chains similarly to a natural interferon β. On the other hand, IFN-β-1b is expressed in $E.$ $coli$, and is a protein without sugar chains.

IFN-β-1a is known to have a more potent effect compared to IFN-β-1b in regards to immunogenicity, anti-viral activity, and anti-tumor property. Further, the sugar chain structure contained in a glycoprotein is known to have a strong influence on pharmacokinetics.

It is also known that effects such as improvement in physical stability, heat stability, a plasma stability of the protein are afforded by binding a water-soluble polymer such as polyethylene glycol (PEG) to the protein. There are reports regarding PEGylated IFN-β with expectation for such effects. For example, there are reports regarding an IFN-β complex that has been PEGylated at the N-terminal of IFN-β-1b (Patent Literatures 1 and 2). There is also a report regarding an IFN-β complex that has been PEGylated at the N-terminal of IFN-β-1a (Patent Literature 3). Such modifications may in fact contribute to the above stabilities of the protein, but meanwhile causes concerns that they reduce the activity of IFN-β as a pharmaceutical. For example, it is reported that the activity is dramatically reduced in cases e.g. when the molecular weight of PEG is 20,000 or more (Non-Patent Literature 1).

With consideration for the above-described concerns of PEGylation, there is also a report of selecting a position that may maintain the activity of IFN-β even when a high molecular weight PEG for site-specific PEGylation is bound (Patent Literature 4). However, since PEG is a compound that does not exist in vivo, sufficient investigation has not yet been established in regards to the accumulatability, the safety, and the effectiveness of long-term administration of PEGylated IFN-β.

Meanwhile, there is also a report regarding site-specifically glycosylated IFN-β complexes (Patent Literature 5). In Patent Literature 5, an amino acid mutation is introduced into the amino acid sequence of natural IFNβ so that it will have a consensus sequence (Asn-X-Ser/Thr) which will be the recognition site for an N-linked sugar drain, and this is expressed with CHO cells. However, with this method, amino acid mutations other than the amino acid to be glycosylated will be produced in order to introduce the consensus sequence. It is also known in general that ununiformity of sugar chains will occur when expressed with CHO cells.

CITATION LIST

[Patent Literature 1] U.S. Published Patent Application No. 2009/0214472
[Patent Literature 2] U.S. Pat. No. 7,829,659
[Patent Literature 3] U.S. Pat. No. 7,416,173
[Patent Literature 4] International Publication No. 2005/019260
[Patent Literature 5] International Publication No. 02/074806
[Non-Patent Literature 1] J. Control. Rel. Vol. 88, pp. 35-42 (2003)

SUMMARY OF THE INVENTION

Problems to be Solved by Invention

There is an example of modifying interferon β polypeptide with PEG in order to improve physical stability, heat stability, plasma stability and the like of interferon β as described above. However, as described above, the activity of interferon β as a pharmaceutical may be reduced when modified with PEG. In addition, since PEG is not a substance that exists in vivo, there is a concern drug-induced suffering due to in vivo accumulation.

On the other hand, an example of modifying an interferon β polypeptide with a sugar chain also exists. However, as described above, for example, it is known that ununiformity is caused in the type of sugar chain added or the added position when glycosylated interferon β is to be manufactured by expression in CHO cells. When sugar chains are not uniform, there is a possibility that difference in drug effect as a medicine will be caused between lots, and there also arises a disadvantage that a natural glycosylated interferon β has a short blood retention time.

Means for Solving the Problems

As a result of extensive investigation by the present inventors to solve the above problems, we found that a glycosylated polypeptide having superior retentivity in blood and superior antitumor activity than a natural human interferon β is obtained by substituting amino acids at 4 to 6 locations with glycosylated in which all of the non-reducing terminals of the sugar chain are sialylated in the interferon β polypeptide.

In other words, the present invention, in one aspect, relates to a glycosylated polypeptide having interferon β activity, characterized in that said glycosylated polypeptide is any polypeptide selected from the group consisting of the following (1) to (4);

(1) a polypeptide consisting of the amino acid sequence represented by SEQ ID NO. 1,
(2) a polypeptide having one or a few amino acids deleted, substituted, or added in the polypeptide consisting of the amino acid sequence represented by SEQ ID NO. 1,
(3) a polypeptide that is an analog of interferon β, and
(4) a polypeptide having 80% or more homology to the polypeptide consisting of the amino acid sequence represented by SEQ ID NO. 1,
in which amino acids at 4 to 6 locations are substituted with glycosylated amino acids, and wherein all of the non-reducing terminals of said sugar chain are sialylated.

In one aspect of the present invention, said respective glycosylated amino acid may be each independently a glycosylated Cys or a glycosylated Asn.

In one aspect of the present invention, the sugar chains in said respective glycosylated amino acid may be all independently selected from the group consisting of a disialo sugar chain, a trisialo sugar chain, and a tetrasialo sugar chain.

In one aspect of the present invention, the sugar chains in said respective glycosylated amino acid may be all independently selected from the group consisting of the following Formula (1), Formula (2), Formula (3), and Formula (4).

[Chemical Formula 1]

Formula (1)

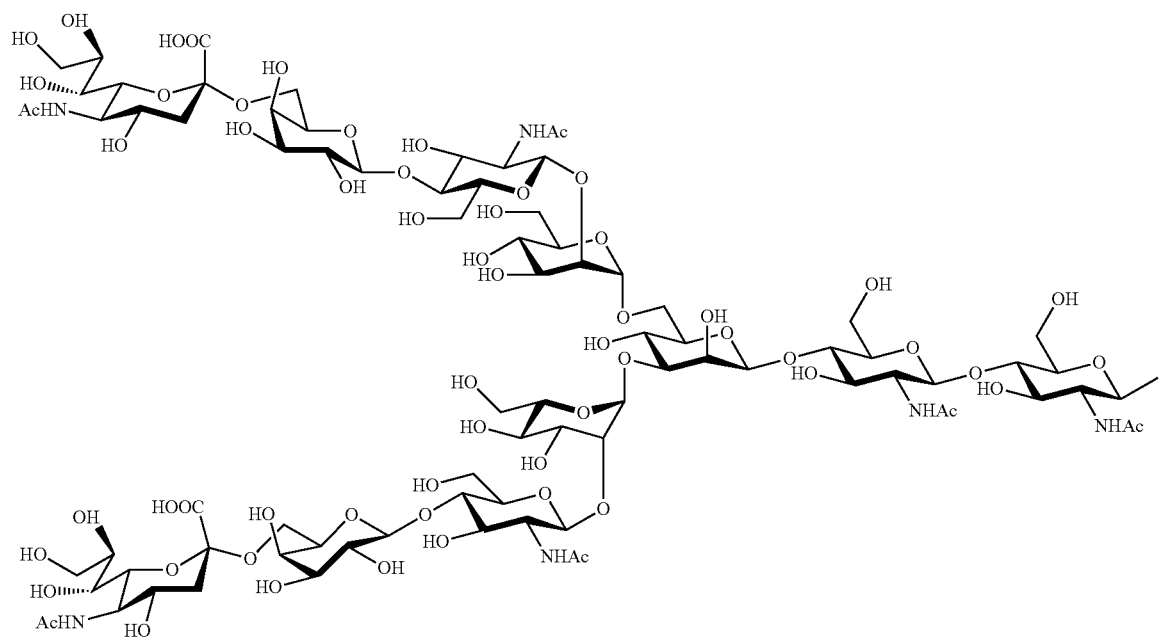

[Chemical Formula 2]

Formula (2)

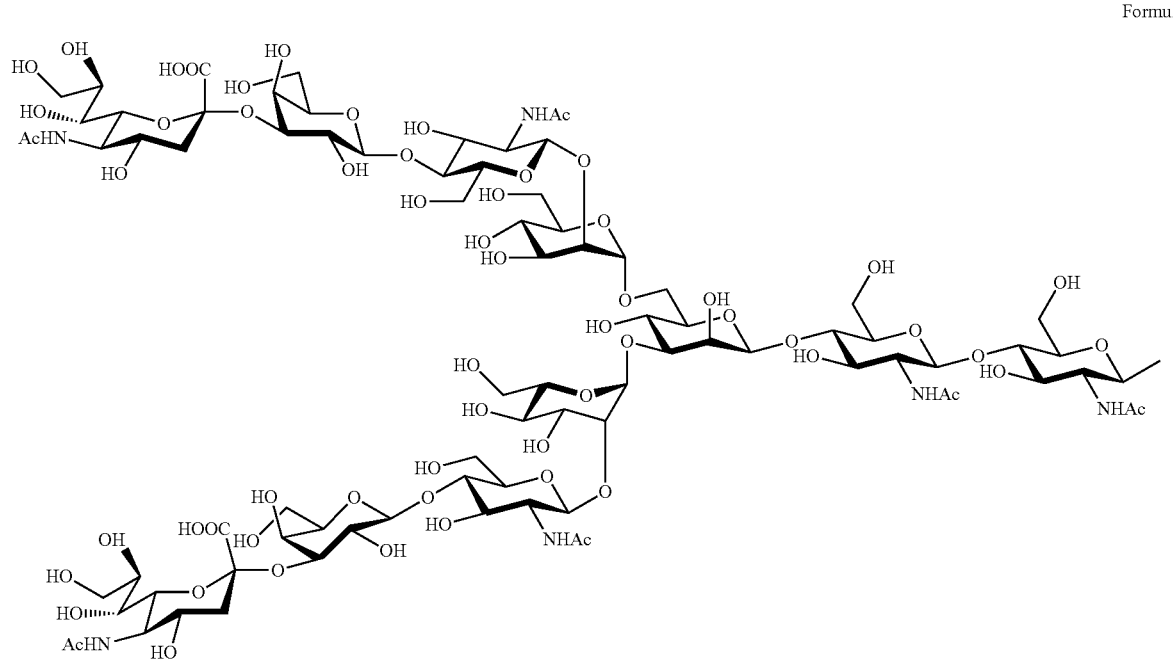

[Chemical Formula 3]

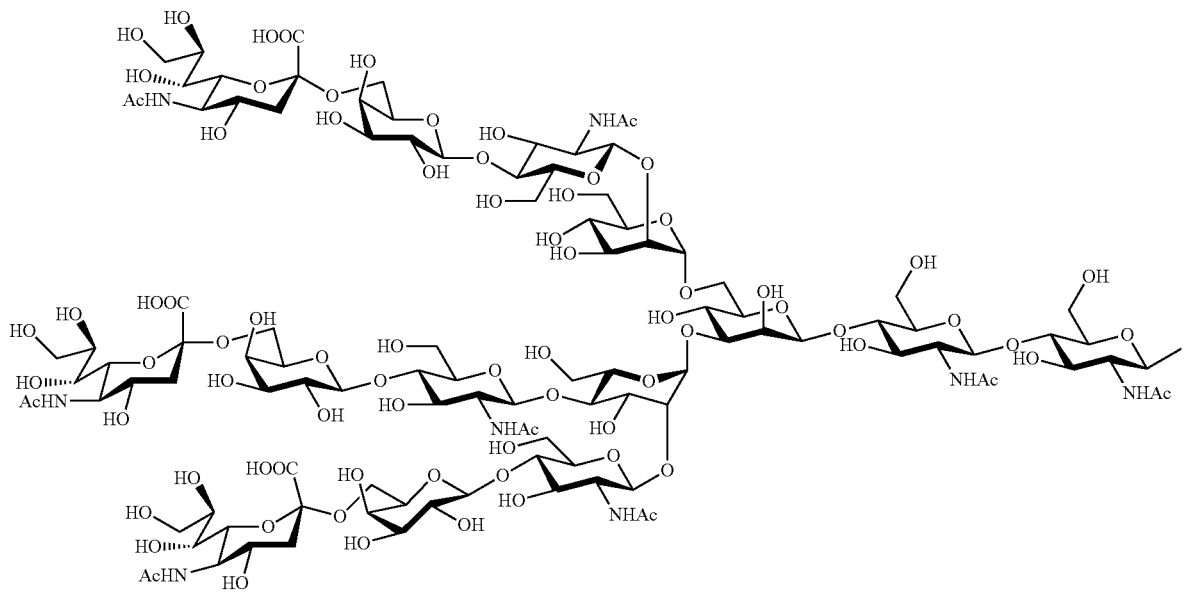

Formula (3)

[Chemical Formula 4]

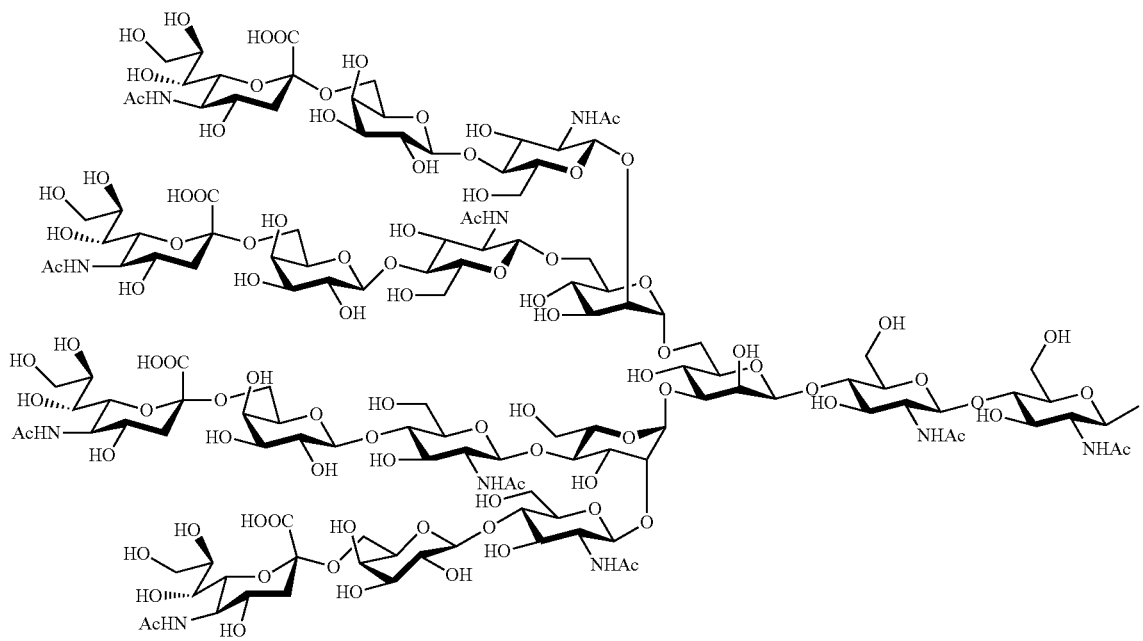

Formula (4)

In one aspect of the present invention, the sugar chains in said respective glycosylated amino acid may be all identical.

In one aspect of the present invention, at least one of said respective glycosylated amino acids may be present at the position corresponding to a position selected from the group consisting of positions 1, 3, 7, 24, 25, 28, 29, 32, 35, 38, 41, 42, 45, 46, 47, 48, 49, 50, 70, 75, 79, 99, 103, 106, 107, 109, 112, 115, 123, 130, 136, 139, and 164 in the amino acid sequence represented by SEQ ID NO. 1.

Here, further in one aspect of the present invention, all of said respective glycosylated amino acids can be those that do not exist at the position corresponding to position 2, 5, 6, 9, 12, 13, 16, 19, 20, 23, 27, 33, 37, 39, 40, 43, 53, 54, 55, 57, 58, 61, 62, 64, 65, 68, 69, 73, 78, 83, 86, 87, 90, 93, 94, 100, 124, 125, 128, 131, 132, 138, 141, 142, 145, 148, 149, 152, 153, 156, 159, 160, or 163 in the amino acid sequence represented by SEQ ID NO. 1.

In one aspect of the present invention, at least one of said respective glycosylated amino acids may be present at the position corresponding to a position selected from the group consisting of positions 1, 3, 41, 48, 75, 79, 107, 112, 123, and 136 in the amino acid sequence represented by SEQ ID NO. 1.

In one aspect of the present invention, at least three of said respective glycosylated amino acids may be present at the position corresponding to a position selected from the group consisting of positions 1, 3, 41, 48, 75, 79, 107, 112, 123, and 136 in the amino acid sequence represented by SEQ ID NO. 1.

In one aspect of the present invention, said respective glycosylated amino acids may be present at the position corresponding to a position selected from the group consisting of positions 1, 3, 7, 24, 25, 28, 29, 32, 35, 38, 41, 42, 45, 46, 47, 48, 49, 50, 70, 75, 79, 99, 103, 106, 107, 109, 112, 115, 123, 130, 136, 139, and 161 in the amino acid sequence represented by SEQ ID NO. 1.

In one aspect of the present invention, said glycosylated polypeptide may be chemically synthesized.

Moreover, in one aspect, the present invention relates to a pharmaceutical composition comprising:
(1) said glycosylated polypeptide and/or pharmaceutically acceptable salt thereof, and
(2) a pharmaceutically acceptable carrier.

In one aspect of the present invention, said pharmaceutical composition may be employed for therapy or prevention of a disease related to interferon β. Here, said disease may be selected from the group consisting of brain tumor, cutaneous malignant melanoma, chronic active hepatitis B, chronic hepatitis C, subacute sclerosing panencephalitis, compensated cirrhosis C, and multiple sclerosis.

Moreover, in one aspect of the present invention, the sequence of the glycosylated polypeptide, the amino acid in the glycosylated amino acid, the type and structure of the sugar chain in the glycosylated amino acid, the position of amino acid substitution by the glycosylated amino acid, the method for synthesizing the glycosylated polypeptide, and the target disease as a pharmaceutical composition as previously described can be any combination selected from the above group, respectively.

Effects of the Invention

The glycosylated polypeptide of the present invention has uniform sugar chain structure because it can be chemically synthesized. According to the present invention, there can thus be provided a glycosylated polypeptide having interferon β activity with stable quality and less variability between lots, as well as a pharmaceutical composition comprising the aforementioned glycosylated polypeptide.

Moreover, glycosylated polypeptide of the present invention may be a polypeptide having a sugar chain that exits in vivo added thereto. According to the present invention, there can therefore be provided a glycosylated polypeptide that is safe for the human body even when administered in long-term, as well as a pharmaceutical composition comprising the aforementioned glycosylated polypeptide.

Moreover, according to the present invention, there can be provided a glycosylated polypeptide retentivity in blood and higher antitumor activity compared to a natural interferon β, as well as a pharmaceutical composition comprising the aforementioned glycosylated polypeptide.

The glycosylated polypeptide of the present invention was shown to have higher retentivity in blood and further higher antitumor activity compared to a natural interferon β.

Although PEGylated interferon β known as the conventional technology is improved in retentivity in blood compared to a natural human interferon β, no improvement in antitumor activity was observed. It is surprising that by virtue of the present invention, improvement in retentivity in blood which was similar to or more than the PEGylated form could be realized by employing a sugar chain having a smaller molecular weight than PEG, and further that antitumor activity was significantly improved in the glycosylated form of the present invention even when it was not improved in the PEGylated form. Accordingly, the glycosylated polypeptide according to the present invention is thought to have high interferon β activity and be extremely useful for treating a disease related to interferon β.

BRIEF DESCRIPTION OF THE DRAWINGS

FIG. 1 is the mass spectra showing the results of performing mass spectrometry (ESI ionization method) on 2-6 diSialo(S1C-Q48C-N79C-K107C-R112C-R123C) obtained in (Example 3-1) and 2-6 monoSialo(S1C-Q48C-N79C-K107C-R112C-R123C) obtained in (Example 4-1).

FIG. 2 is a photograph showing the results of performing SDS-PAGE on 2-6 diSialo(S1C-Q48C-N79C-K107C-R112C-R123C) obtained in (Example 3-1) and 2-6 monoSialo(S1C-Q48C-N79C-K107C-R112C-R123C) obtained in (Example 4-1).

FIG. 3 is the mass spectra showing the results of performing analysis by normal phase HPLC on the sugar chain components 2-6 diSialo(S1C-Q48C-N79C-K107C-R112C-R123C) obtained in (Example 3-1) and 2-6 monoSialo(S1C-Q48C-N79C-K107C-R112C-R123C) obtained in (Example 4-1).

FIG. 4 is a graph showing the transition of plasma concentration for each glycosylated polypeptide when 2-6 diSialo(S1C-Q48C-N79C-K107C), 2-6 diSialo(S1C-Q48C-N79C-K107C-R112C), and 2-6 diSialo(S1C-Q48C-N79C-K107C-R112C-R123C) were subcutaneously administered.

FIG. 5 is a table showing the pharmacokinetical parameters for each glycosylated polypeptide when 2-6 diSialo(S1C-Q48C-N79C-K107C), 2-6 diSialo(S1C-Q48C-N79C-K107C-R112C), and 2-6 diSialo(S1C-Q48C-N79C-K107C-R112C-R123C) were subcutaneously administered.

FIG. 6 is graph representations showing the transition of plasma concentration for each glycosylated polypeptide when 2-6 diSialo(S1C-Q48C-N79C-K107C), 2-6 monoSialo(S1C-Q48C-N79C-K107C) were intravenously and subcutaneously administered. The left graph is a graph representation of the transition of plasma concentration for each glycosylated polypeptide when intravenously administered, and the right graph is a graph showing the transition of plasma concentration for each glycosylated polypeptide when subcutaneously administered.

FIG. 7 is a table showing the pharmacokinetical parameters for each glycosylated polypeptide when 2-6 diSialo(S1C-Q48C-N79C-K107C) and 2-6 monoSialo(S1C-Q48C-N79C-K107C) were intravenously and subcutaneously administered.

FIG. 8 is a graph showing the transition of plasma concentration for each glycosylated polypeptide when 2-6 diSialo(S1C-Q48C-N79C-K107C-R112C-R123C) and 2-6 monoSialo(S1C-Q48C-N79C-K107C-R112C-R123C) were intravenously administered.

FIG. 9 is a table showing the pharmacokinetical parameters for each glycosylated polypeptide when 2-6 diSialo(S1C-Q48C-N79C-K107C-R112C-R123C) and 2-6 monoSialo(S1C-Q48C-N79C-K107C-R112C-R123C) were intravenously administered.

FIG. 10 is a graph showing the transition of plasma concentration for each glycosylated polypeptide when 2-6 diSialo(S1C-Q48C-N79C-K107C-R112C-R123C) and PEG20K-modified IFNβ were subcutaneously administered.

FIG. 11 is a table showing the pharmacokinetical parameters for each glycosylated polypeptide when 2-6 diSialo (S1C-Q48C-N79C-K107C-R112C-R123C) and PEG20K-modified IFNβ were subcutaneously administered.

FIG. 12 is a graph showing the results of antitumor activity evaluation in biliary cancer mice that were subcutaneously administered 2-6 diSialo(S1C-Q48C-N79C-K107C), 2-6 diSialo(S1C-N3C-Q48C-N79C-K107C-R112C), 2-6 diSialo(S1C-Q48C-N79C-K107C-R112C-R123C), and 2-6 diSialo(S1C-N3C-Q48C-N79C-K107C-R112C).

FIG. 13 is a graph showing the results of antitumor activity evaluation in biliary cancer mice that were subcutaneously administered 2-6 diSialo(S1C-Q48C-N79C-K107C-R112C-R123C) and 2-6 monoSialo(S1C-N3C-Q48C-N79C-K107C-R112C), 2-6 diSialo(S1C-Q48C-N79C-K107C-R112C-R123C).

FIG. 14 is a graph showing the results of antitumor activity evaluation in biliary cancer mice that were subcutaneously administered 2-6 diSialo(S1C-Q48C-N79C-K107C-R112C-R123C), 2-6 triSialo(S1C-Q48C-N79C-K107C-R112C-R123C), and 2-6 tetraSialo(S1C-Q48C-N79C-K107C-R112C-R123C).

FIG. 15 is a graph showing the results of antitumor activity evaluation in biliary cancer mice that were subcutaneously administered 2-6 diSialo(S1C-Q48C-N79C-K107C-R112C-R123C) and PEG20K-modified IFN-β.

FIG. 16 shows the amino acid sequence of interferon β-1b (SEQ ID NO. 1) as an example of the amino acid sequence of interferon β herein.

DESCRIPTION OF EMBODIMENTS

The present invention relates to a polypeptide glycosylated with a sialylated sugar chain. Specifically, the present invention relates to a glycosylated polypeptide having interferon β activity glycosylated with highly uniform sialylated sugar chains.

A "sugar chain" herein refers to a compound made of one or more unit sugars (a monosaccharide and/or a derivative thereof) connected together. When two or more unit sugars are connected together, each unit sugar is bound by a dehydration condensation by a glycoside bond in between. Such sugar chains include, but are not limited to, for example, a broad range such as monosaccharides and polysaccharides contained in vivo (glucose, galactose, mannose, fucose, xylose, N-acetylglucosamine, N-acetylgalactosamine, sialic acid, and complexes and derivatives thereof), as well as sugar chains that have been degraded or induced from complex biological materials such as degraded polysaccharides, glycoproteins, proteoglycans, glycosaminoglycans, and glycolipids.

The preferred sugar chain herein is a sugar chain that does not dissipate interferon β activity of the interferon complex. Such a sugar chain is not particularly limited, and may be a sugar chain that exists as a glycoconjugate in vivo (such as a glycopeptide or a glycoprotein, a proteoglycan, and a glycolipid), or it may be a carbohydrate that does not exist as a glycoconjugate in vivo.

A sugar chain that exists as a glycoconjugate in vivo is preferred with respect to the fact that the interferon complex of the present invention is administered in vivo. Examples of a sugar chain that exists as a glycoconjugate in vivo include N- or O-linked sugar chains and the like which are sugar chains bound to a peptide or protein in vivo as a glycopeptide or a glycoprotein.

In one aspect of the present invention, an N-linked sugar chain is preferably employed. N-linked sugar chains can include, e.g., a high-mannose form, a complex form, or a hybrid form, particularly preferably a complex form.

The sugar chains herein are characterized in that all of the non-reducing terminals of the sugar chains are sialylated. "All of the non-reducing terminals of the sugar chains are sialylated" herein, for example, means that both of the two non-reducing terminals are sialylated in the case of a biantennary complex sugar chain, all of the three non-reducing terminals are sialylated in the case of a triantennary complex sugar chain, and all of the four non-reducing terminals are sialylated in the case of a tetraantennary complex sugar chain.

Sialylation herein means that a sialic acid is bound to the non-reducing terminal of the sugar chain. Sialic acid is a generic term for a neuraminic acid having the amino group or the hydroxy group substituted. In the present invention, the sialic acid present in the non-reducing terminal of the sugar chain may include any and all substituted forms of neuraminic acid, as long as it does not dissipate or significantly reduce interferon activity of the glycosylated polypeptide of the present invention. Among these, the sialylation of the sugar chain in the glycosylated polypeptide according to the present invention is preferably a naturally-occurring sialic acid with respect to the fact that the glycosylated polypeptide of the present invention is administered in vivo. For example, N-acetylneuramic acid (Neu5Ac) acetylated at position 5 or N-glycolyl neuraminic acid (Neu5Gc) modified with glycolic acid at position 5 and the like are known as naturally-occurring sialic acids.

As one aspect of the present invention, specific examples of sugar chains having all of the non-reducing terminals sialylated include, e.g., as a sugar chain known to exist in vivo, a complex sugar chain of an N-linked sugar chain. As the complex sugar chain of an N-linked sugar chain, those differing in its binding mode, the presence or absence of fucose, the presence or absence of modification on the side chain substituent, and the like are also included, as long as it has the basic skeleton of a sugar chain generally known as a complex sugar chain of an N-linked sugar chain. Examples of an N-linked complex sugar chain can include, depending on the difference in the branching structure of the sugar chain, e.g., a disialo sugar chain, a trisialo sugar chain, and a tetrasialo sugar chain. In other words, a "disialo sugar chain" herein refers to an N-linked complex sugar chain that has a biantennary structure and has all of the non-reducing terminals sialylated. Similarly, a "trisialo sugar chain" refers to an N-linked complex sugar chain that has a triantennary structure and has all of the non-reducing terminals sialylated. Similarly, a "tetrasialo sugar chain" refers to an N-linked complex sugar chain that has a tetraantennary structure and has all of the non-reducing terminals sialylated.

More specifically, these sugar chains can include the α2-6 disialo sugar chain represented by the following Formula (1), the α2-3disialo sugar chain represented by the Formula (2), the α2-6 trisialo sugar chain represented by Formula (3), the α2-6 tetrasialo sugar chain represented by Formula (4), and the like.

[Chemical Formula 5]
Formula (1)
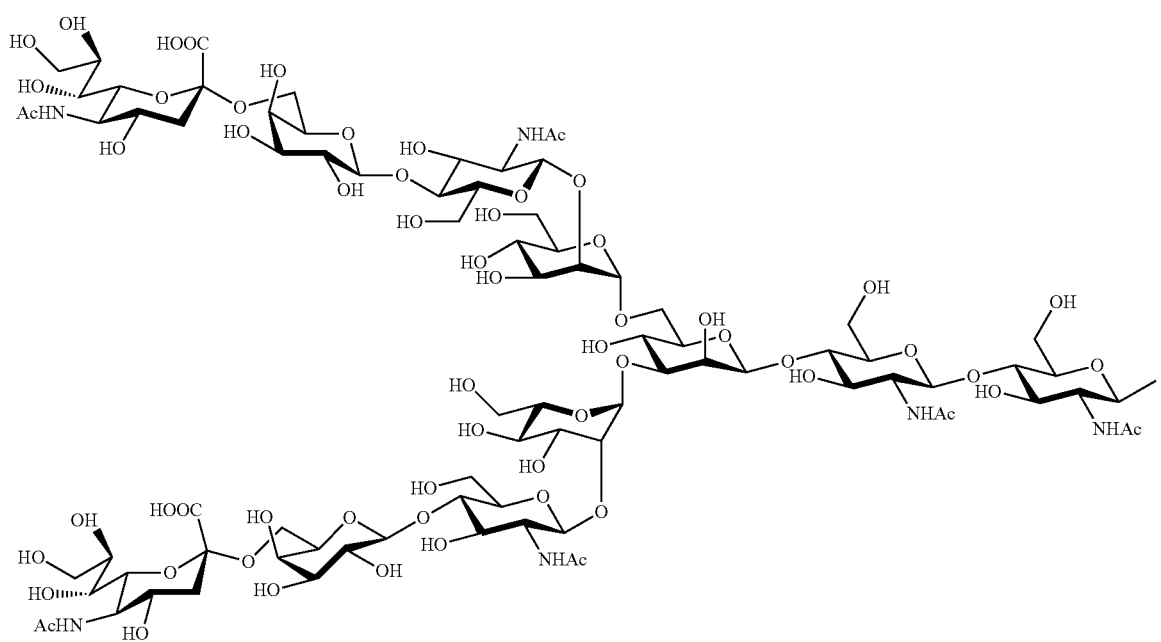
[Chemical Formula 6]
Formula (2)
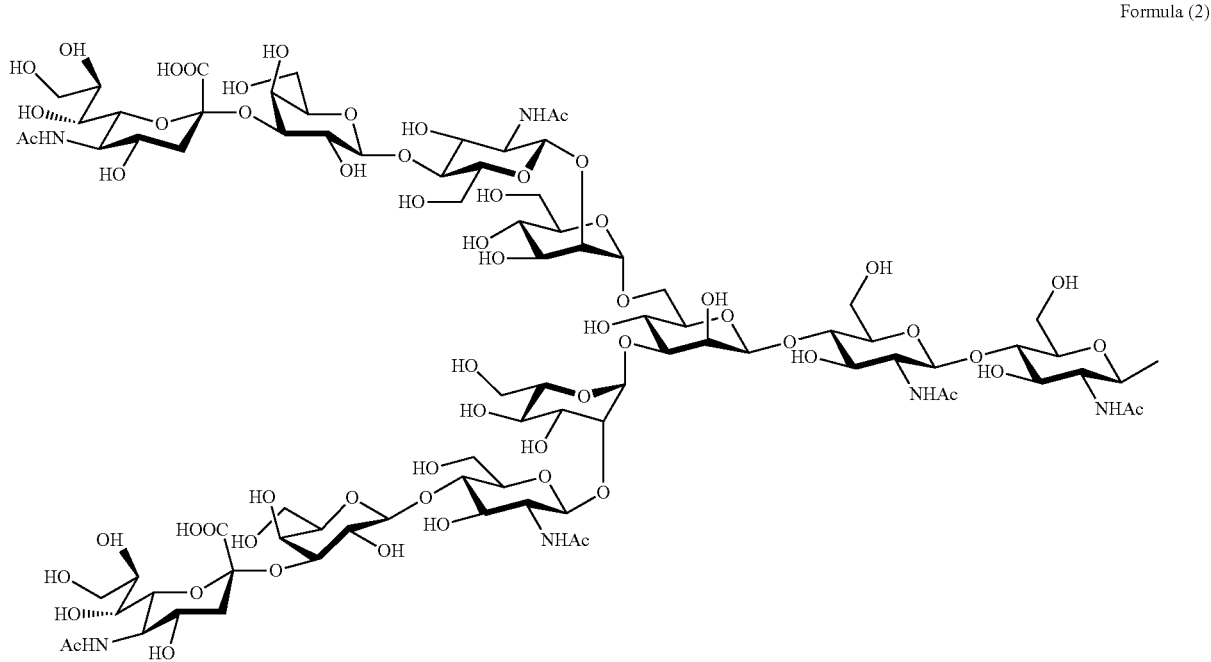

[Chemical Formula 7]

Formula (3)

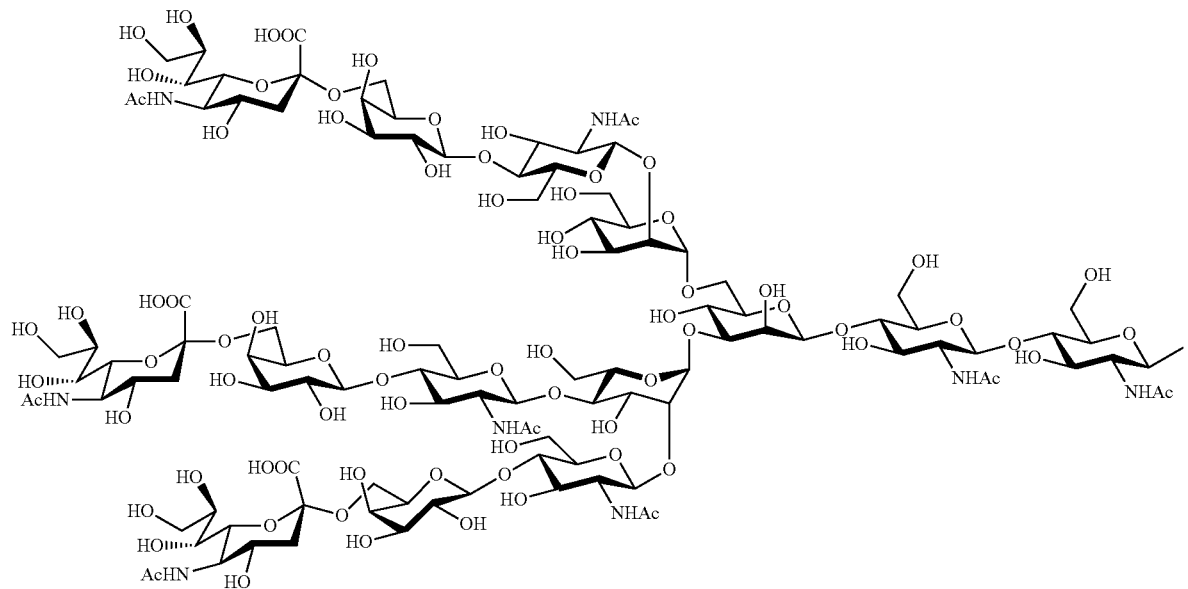

[Chemical Formula 8]

Formula (4)

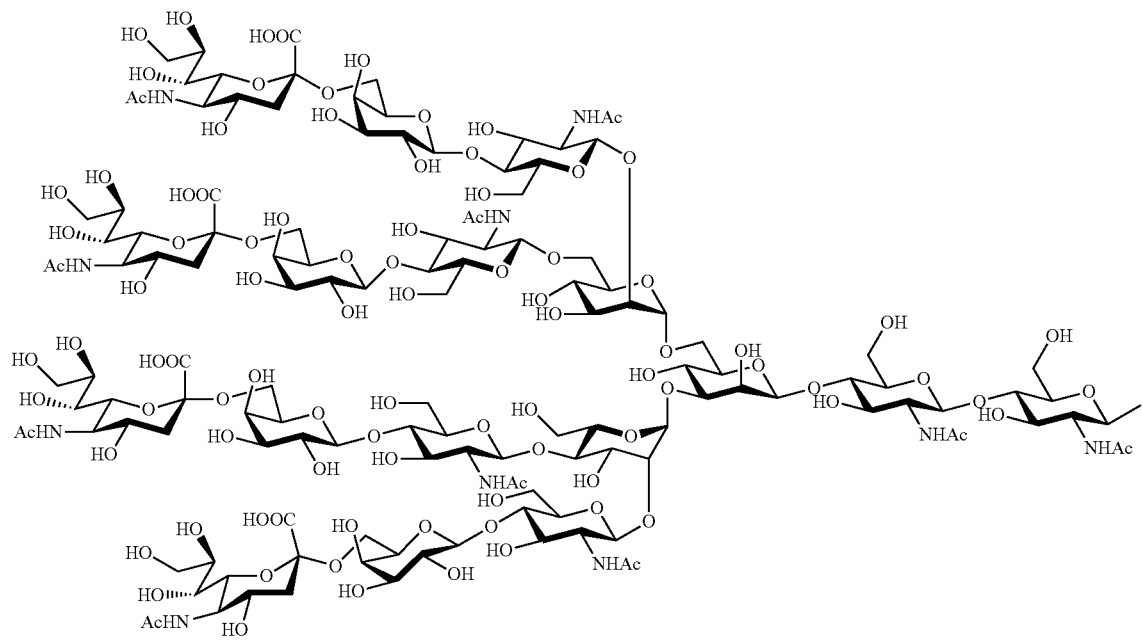

The sialylated sugar chains herein are not limited to the above specific examples, and include those wherein the binding mode between the sugar chain and the sialic acid is different such as α2-3 trisialo and α2-3 tetrasialo sugar chains. As for the binding mode, all branched chains in the sialylated sugar chain may be an identical binding mode, or may include different binding modes.

Moreover, the sialylated sugar chain herein also includes those having a fucose added thereto. Specific examples of a complex sugar chain having a fucose added can include, the following Formula (13) in case of a disialo sugar chain, the following Formula (15) and Formula (16) in case of a trisialo sugar chain, and the following Formula (17) in case of a tetrasialo sugar chain.

[Chemical Formula 9]
Formula (13)
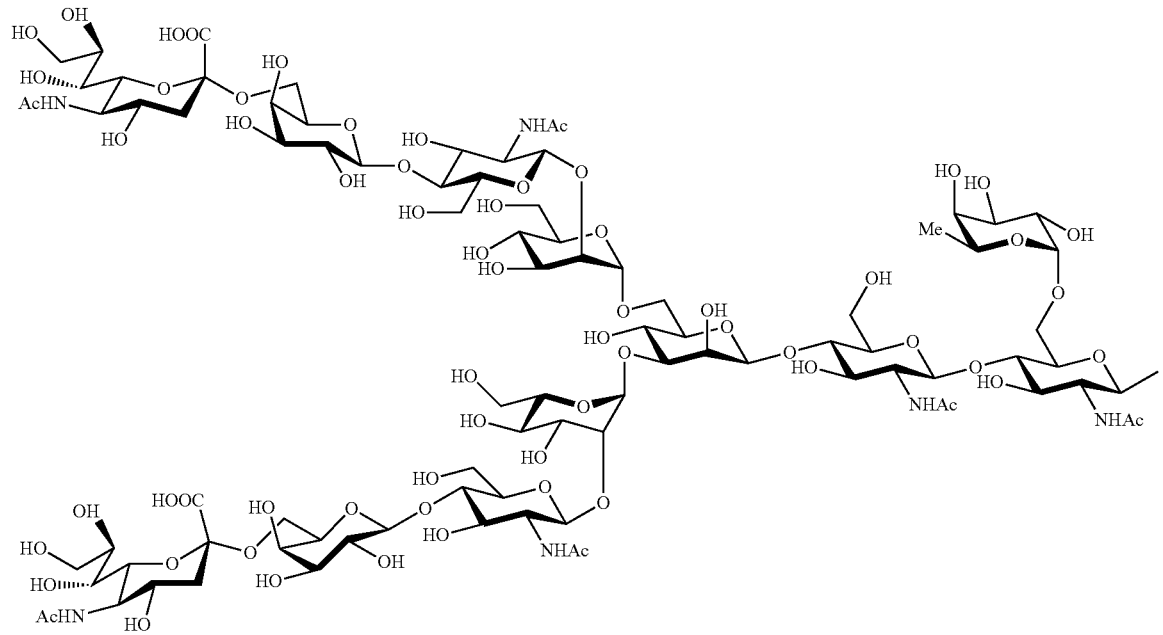
[Chemical Formula 10]
Formula (15)
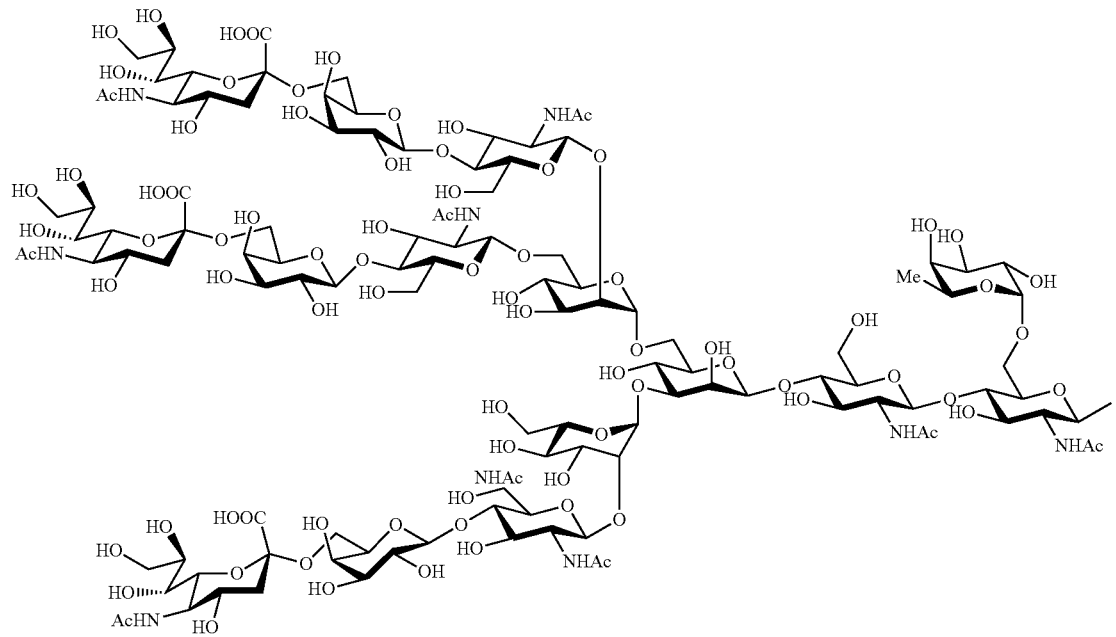

[Chemical Formula 11]

Formula (16)

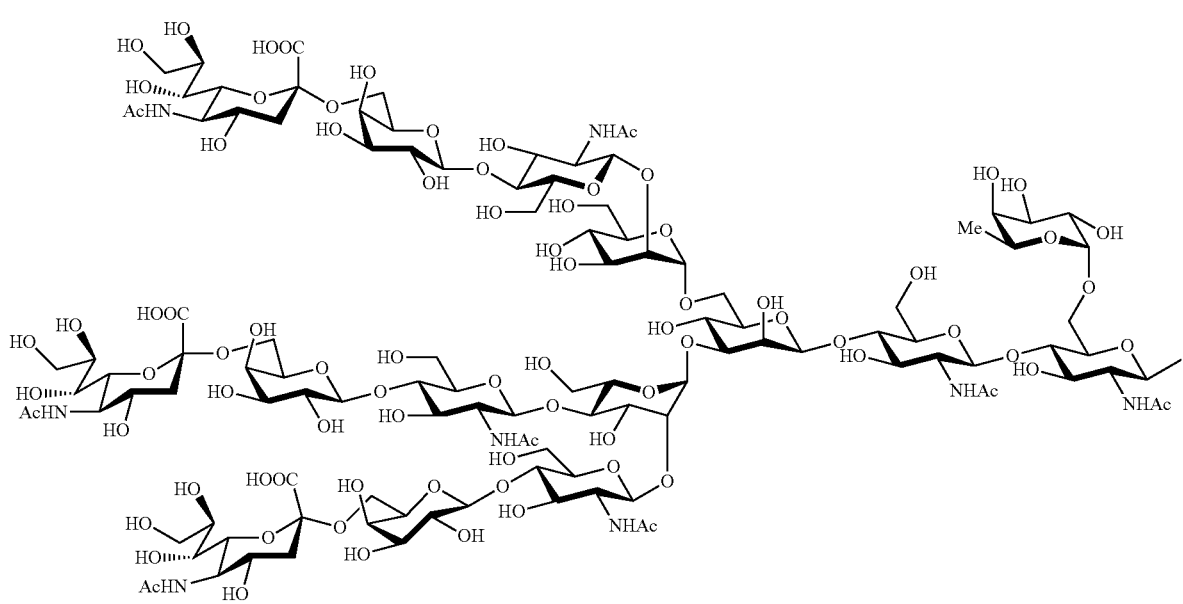

[Chemical Formula 12]

Formula (17)

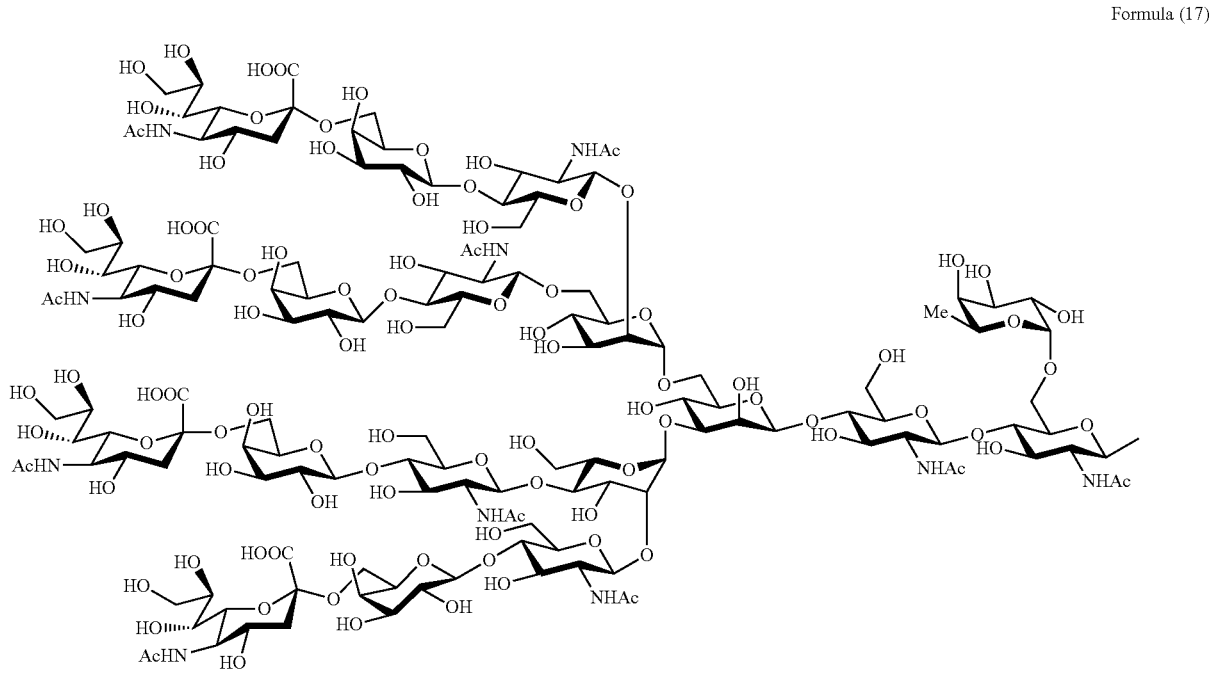

In one aspect of the present invention, the sugar chains of the respective glycosylated amino acid in the glycosylated polypeptide of the present invention can all be identical, or they can also comprise different sugar chains. The sugar chains of the respective glycosylated amino acid in the glycosylated polypeptide are identical as used herein refers to the fact that when amino acids at 4 to 6 locations are substituted with glycosylated amino acids in the present invention, the type of sugar configuring the sugar chain, the binding order, and the binding mode are identical within the glycosylated polypeptide when the sugar chains at the glycosylated amino acids at the 4 to 6 locations are compared with each other.

Moreover, in one aspect of the present invention, in a composition containing the glycosylated polypeptide of the present invention, each sugar chain in the glycosylated polypeptide is preferably each substantially uniform. Each sugar chain in the glycosylated polypeptide is each substantially uniform as used herein refers to the fact that when each sugar chain is compared between glycosylated polypeptides for ever glycosylation position, the positions on the polypeptide are identical, and the type of sugar configuring the sugar chain at each position, the binding order, and the binding mode between sugars are each substantially identical in each sugar chain. In the present invention, each sugar chain in the glycosylated polypeptide is at least 90% ore more, preferably 95% or more, and more preferably 99% or more uniform.

A composition comprising a glycosylated polypeptide wherein each sugar chain in the glycosylated polypeptide is each substantially uniform has constant quality, and is particularly preferred in fields such as medicinal manufacturing and assays. The proportion of uniform sugar chains can be measured for example by a method employing HPLC, capillary electrophoresis, mass spectrometry, and the like.

The "amino acid sequence represented by SEQ ID NO. 1" herein is the amino acid sequence of interferon-β-1b (see FIG. 16). Interferon β-1b is known to have Met at position 1 deleted and Cys at position 17 substituted to Ser in a natural human interferon β.

A "glycosylated polypeptide" herein refers to e.g. a polypeptide consisting of the amino acid sequence represented by SEQ ID NO. 1 having amino acids at 4 to 6 locations substituted with "glycosylated amino acids."

A "glycosylated amino acid" herein is an amino acid having a sugar chain bound thereto, wherein the sugar chain and the amino acid may be bound via a linker.

The type of the amino acid to be glycosylated is not particularly limited, and any of natural amino acids and non-natural amino acids can be employed.

When the sugar chain and the amino acid are bound via a linker, the preferred amino acid of the glycosylated amino acid, with respect to easy binding with the linker, is an amino acid having two or more carboxy groups in a molecule such as aspartic acid and glutamic acid, an amino acid having two or more amino groups in a molecule such as lysine, arginine, histidine, and tryptophan, an amino acid having a hydroxyl group in the molecule such as serine, threonine, and tyrosine, an amino acid having a thiol group in the molecule such as cysteine, and an amino acid having an amide group in the molecule such as asparagine and glutamine. In particular, cysteine, aspartic acid, glutamic acid, lysine, arginine, serine, threonine, and glutamine are preferred with respect to reactivity.

For any glycosylated polypeptide of the present invention, if the sugar chain structure, the structure other than the sugar chain, the glycosylation site, and the number of sugar chains added are identical, there is thought to be no major difference in the half-life in blood of the glycosylated polypeptide of the present invention between when the glycosylated amino acid is a glycosylated Asn and when it is a glycosylated Cys.

When the sugar chain and the amino acid are bound via a linker, those employed in the fields concerned can be broadly used as the linker, examples of which can include —NH—(CO)—(CH$_2$)$_a$—CH$_2$— (wherein a indicates an integer which is not limited as long as it does not inhibit the target linker function, but is preferably an integer from 0 to 4), C$_{1-10}$ polymethylene, —CH$_2$-R— (wherein R is a group produced by detaching one hydrogen atom from a group selected from the group consisting of an alkyl, a substituted alkyl, an alkenyl, a substituted alkenyl, an alkynyl, a substituted alkynyl, an aryl, a substituted aryl, a carbocyclic group, a substituted carbocyclic group, a heterocyclic group, and a substituted heterocyclic group, —(CO)—(CH$_2$)$_a$—(CO)— (wherein a indicates an integer which is not limited as long as it does not inhibit the target linker function, but is preferably an integer from 0 to 4), and the like.

The manufacturing method of the glycosylated polypeptide of the present invention is not to be limited in any way by the description thereof (such as the description "glycosylated polypeptide having an amino acid is substituted with a glycosylated amino acid"), and a glycosylated polypeptide manufactured by either of methods A or B described below is included in the "glycosylated polypeptide having an amino acid is substituted with a glycosylated amino acid." Moreover, for example, a glycosylated polypeptide in which a sugar chain without any amino acid bound thereto is bound directly or via a linker to an acid on a peptide; a glycosylated polypeptide in which a sugar or a sugar chain is further added to the sugar chain added in the glycosylated polypeptide in order to elongate; the already added sugar chain; a glycosylated polypeptide in which one or a few amino acids are bound to the amino and/or carboxy group of a glycosylated amino acid, and further linked to one or more interferon β fragments; and a glycosylated polypeptide in which a sugar chain having an amino acid bound thereto is bound via a linker to an amino acid on a peptide, and the like are also included in the glycosylated polypeptide of the present invention, as long as the final structure matches.

In one aspect of the present invention, the positions for substituting the "amino acids at 4 to 6 locations" described above with glycosylated amino acids should be selected in light of various respects so that interferon β activity will not be reduced by substitution of the glycosylated amino acid. For example, Asn at position 80 (corresponding to position 79 in the amino acid sequence represented by SEQ ID NO. 1) where the sugar chain is bound to in a natural interferon β is preferred herein as a position to be substituted by a glycosylated amino acid.

In one aspect of the present invention, the substitution position for the glycosylated amino acid is preferably selected so that it will not disturb the formation of interferon β conformation in polypeptide folding. In order to avoid disturbing the formation of interferon β conformation, the substitution position for the glycosylated amino acid can be the position of amino acids present at the surface of the conformational structure when interferon β had formed a conformation similar to that in nature. In other words, the position can be amino acid positions that do not configure the vicinity of the conformational structure surface when interferon β had formed a conformation similar to that in nature (also referred to herein as "the position of non-surface amino acids.") Moreover, in one aspect of the present invention, the substitution position for the glycosylated amino acid is preferably not the receptor binding site of interferon β. The present invertors performed extensive investigations with data such as conformational analysis of interferon β to estimate the positions of non-surface amino acids of interferon β, and estimated positions that may disturb other conformational formation or positions that may disturb binding with the receptor. From such perspective, in one aspect of the present invention, the glycosylated amino acid is preferably not present at the position corresponding to positions 2, 5, 6, 9, 12, 13, 16, 19, 20, 23, 27, 33, 37, 39, 40, 43, 53, 54, 55, 57, 58, 61, 62, 64, 65, 68, 69, 73, 78, 83, 86, 87, 90, 93, 94, 100, 124, 125, 128, 131, 132, 138, 141, 142, 145, 148, 149, 152, 153, 156, 159, 160, or 163 in the amino acid sequence represented by SEQ ID NO. 1. Moreover, those skilled in the art having seen this specification will be able to appropriately investigate similarly unpreferable substitution positions for the glycosylated amino acid according to these positions.

In one aspect of the present invention, the substitution position for the glycosylated amino acid is preferably not Cys positions 31 and 141 that forms a disulfide bond in a natural interferon β (corresponding to positions 30 and 140 in the amino acid sequence represented by SEQ ID NO. 1).

The present inventors performed extensive research from the perspective described above to synthesize numerous glycosylated polypeptides having various amino acids on the amino acid sequence substituted with glycosylated amino acids and measured their interferon β activities. As a result, it was found that at least positions 1, 3, 7, 24, 25, 28, 29, 32, 35, 38, 41, 42, 45, 46, 47, 48, 49, 50, 70, 75, 79, 99, 103, 106, 107, 109, 112, 115, 123, 130, 136, 139, and 164 in the amino acid sequence represented by SEQ ID NO. 1 are positions that contribute to the maintenance or improvement of interferon β activity by glycosylation.

From the above reasons, in one aspect of the present invention, at least one of the respective glycosylated amino acids is preferably present at the position corresponding to a position selected from the group consisting of positions 1, 3, 7, 24, 25, 28, 29, 32, 35, 38, 41, 42, 45, 46, 47, 48, 49, 50, 70, 75, 79, 99, 103, 106, 107, 109, 112, 115, 123, 130, 136, 139, and 164 in the amino acid sequence represented by SEQ ID NO. 1.

Moreover, in one aspect of the present invention, at least two of the respective glycosylated amino acids are preferably present at the position corresponding to a position selected from the group consisting of positions 1, 3, 7, 24, 25, 28, 29, 32, 35, 38, 41, 42, 45, 46, 47, 48, 49, 50, 70, 75, 79, 99, 103, 106, 107, 109, 112, 115, 123, 130, 136, 139, and 164 in the amino acid sequence represented by SEQ ID NO. 1.

Moreover, in one aspect of the present invention, at least three of the respective glycosylated amino acids are preferably present at the position corresponding to a position selected from the group consisting of positions 1, 3, 7, 24, 25, 28, 29, 32, 35, 38, 41, 42, 45, 46, 47, 48, 49, 50, 70, 75, 79, 99, 103, 106, 107, 109, 112, 115, 123, 130, 136, 139, and 164 in the amino acid sequence represented by SEQ ID NO. 1.

Moreover, in one aspect of the present invention, at least four of the respective glycosylated amino acids are preferably present at the position corresponding to a position selected from the group consisting of positions 1, 3, 7, 24, 25, 28, 29, 32, 35, 38, 41, 42, 45, 46, 47, 48, 49, 50, 70, 75, 79, 99, 103, 106, 107, 109, 112, 115, 123, 130, 136, 139, and 164 in the amino acid sequence represented by SEQ ID NO. 1.

Moreover, in one aspect of the present invention, when 5 or more locations are substituted by glycosylated amino acids, at least five of the respective glycosylated amino acids are preferably present at the position corresponding to a position selected from the group consisting of positions 1, 3, 7, 24, 25, 28, 29, 32, 35, 38, 41, 42, 45, 46, 47, 48, 49, 50, 70, 75, 79, 99, 103, 106, 107, 109, 112, 115, 123, 130, 136, 139, and 164 in the amino acid sequence represented by SEQ ID NO. 1.

In one aspect of the present invention, it is more preferred that each of the glycosylated amino acids described above are all present at the position corresponding to a position selected from the group consisting of positions 1, 3, 7, 24, 25, 28, 29, 32, 35, 38, 41, 42, 45, 46, 47, 48, 49, 50, 70, 75, 79, 99, 103, 106, 107, 109, 112, 115, 123, 130, 136, 139, and 164 in the amino acid sequence represented by SEQ ID NO. 1.

In one aspect of the present invention, it is more preferred that one of the glycosylated amino acids is present at the position corresponding to position 79 in the amino acid sequence represented by SEQ ID NO. 1.

Moreover, in one aspect of the present invention, it is more preferred that one or more of each of the other glycosylated amino acids (other than position 79) are present at the position corresponding to a position selected from the group consisting of positions 1, 3, 7, 24, 25, 28, 29, 32, 35, 38, 41, 42, 45, 46, 47, 48, 49, 50, 70, 75, 79, 99, 103, 106, 107, 109, 112, 115, 123, 130, 136, 139, and 164 in the amino acid sequence represented by SEQ ID NO. 1.

Moreover, these positions are preferred specific examples, and are not to limit the positions listed herein. Those skilled in the art having seen the present invention will be able to select the positions to be substituted with glycosylated amino acids similarly to the present invention.

In one aspect of the present invention, one of the respective glycosylated amino acids is preferably present at the position corresponding to position 1 in the amino acid sequence represented by SEQ ID NO. 1.

In one aspect of the present invention, one of the respective glycosylated amino acids is preferably present at the position corresponding to position 3 in the amino acid sequence represented by SEQ ID NO. 1.

In one aspect of the present invention, one of the respective glycosylated amino acids is preferably present at the position corresponding to position 41 in the amino acid sequence represented by SEQ ID NO. 1.

In one aspect of the present invention, one of the respective glycosylated amino acids is preferably present at the position corresponding to position 48 in the amino acid sequence represented by SEQ ID NO. 1.

In one aspect of the present invention, one of the respective glycosylated amino acids is preferably present at the position corresponding to position 75 in the amino acid sequence represented by SEQ ID NO. 1.

In one aspect of the present invention, one of the respective glycosylated amino acids is preferably present at the position corresponding to position 79 in the amino acid sequence represented by SEQ ID NO. 1.

In one aspect of the present invention, one of the respective glycosylated amino acids is preferably present at the position corresponding to position 107 in the amino acid sequence represented by SEQ ID NO. 1.

In one aspect of the present invention, one of the respective glycosylated amino acids is preferably present at the position corresponding to position 112 in the amino acid sequence represented by SEQ ID NO. 1.

In one aspect of the present invention, one of the respective glycosylated amino acids is preferably present at the position corresponding to position 123 in the amino acid sequence represented by SEQ ID NO. 1.

In one aspect of the present invention, one of the respective glycosylated amino acids is preferably present at the position corresponding to position 136 in the amino acid sequence represented by SEQ ID NO. 1.

Moreover, in one aspect of the present invention, when substituting an amino acid glycosylated amino acid, the position can be any combination of positions selected from the above substitution positions.

Specific examples of preferable combination of positions in which respective glycosylated amino acids are present described above herein can be exemplified by the positions corresponding to the following positions in the amino acid sequence represented by SEQ ID NO. 1, but are not limited thereto.

positions 1, 48, 79, 107, 112, and 123;
positions 1, 3, 48, 79, 107 and 112;
positions 1, 48, 79, 99, 107, and 112;
positions 1, 48, 79, 107, 112, and 130;

positions 1, 48, 79, 107, 112, and 136;
positions 1, 48, 79, 107, 112, and 139;
positions 1, 48, 79, 107, 112, and 164;
positions 1, 29, 48, 79, 107, and 136;
positions 1, 35, 48, 79, 107, and 136;
positions 1, 41, 48, 79, 107, and 136;
positions 1, 48, 75, 79, 107, and 136;
positions 48, 75, 79, 107, 112, and 136;
positions 41, 75, 79, 103, 107, and 136;
positions 41, 75, 79, 106, 107, and 136;
positions 41, 75, 79, 107, 109, and 136;
positions 41, 75, 79, 107, 112, and 136;
positions 41, 75, 79, 107, 115, and 136;
positions 41, 75, 79, 107, 119, and 136;
positions 1, 28, 48, 70, and 79;
positions 1, 48, 79, 107, and 112;
positions 24, 79, 107, 112, and 136;
positions 25, 79, 107, 112, and 136;
positions 32, 79, 107, 112, and 136;
positions 35, 79, 107, 112, and 136;
positions 38, 79, 107, 112, and 136;
positions 41, 79, 107, 112, and 136:
positions 7, 79, 107, 112, and 136;
positions 48, 79, 107, 112, and 136;
positions 75, 79, 107, 112, and 136;
positions 41, 75, 79, 107, and 136;
positions 42, 75, 79, 107, and 136;
positions 45, 75, 79, 107, and 136;
positions 46, 75, 79, 107, and 136;
positions 47, 75, 79, 107, and 136;
positions 48, 75, 79, 107, and 136;
positions 49, 75, 79, 107, and 136;
positions 50, 75, 79, 107, and 136;
positions 1, 48, 79, and 107;
positions 1, 3, 48, and 79;
positions 79, 107, 112, and 136;
positions 1, 79, 107, and 136;
positions 28, 79, 107, and 136;
positions 35, 79, 107, and 136;
positions 70, 79, 117, and 136; and
positions 75, 79, 107, and 136.

The position corresponding to the position in the amino acid sequence represented by SEQ ID NO. 1 herein refers to the amino acid at the position corresponding to the amino acid position in the amino acid sequence represented by SEQ ID NO. 1, as long as there is no addition, deletion, etc. of amino acids. Further, when addition or deletion of amino acids is present in the amino acid sequence represented by SEQ ID NO. 1, the term refers to the amino acid at the position that takes into consideration the shift on the amino acid sequence due to the addition or deletion of amino acids. For example, in a glycosylated interferon β-1b having the sequence Ser$_1$-Tyr$_2$-Asn$_3$-Leu$_4$- at positions 1 to 4, when one amino acid (Trp) is added between amino acids at positions 1 and 2 (Ser-Trp-Tyr-Asn-Leu-), "the position corresponding to position 2 (Tyr)" refers to the position of the amino acid (Tyr) which is shifted one towards the C-terminal due to Trp addition.

An "amino acid" herein is used in its broadest meaning, and may include not only natural amino acids but also non-natural amino acids such as amino acid variants and derivatives. Those skilled in the art will recognize that in light of this broad definition, amino acids herein include, e.g., natural proteinogenic L-amino acids; D-amino acids; chemically modified amino acids such as amino acid variants and derivatives; natural non-proteinogenic amino acids such as norleucine, β-alanine, and ornithine; chemically synthesized compounds having properties well-known in the art which are characteristic of amino acids, and the like. Examples of non-natural amino acids include α-methyl-amino acids (such as α-methylalanine), D-amino acids, histidine-like amino acids (such as 2-amino-histidine, β-hydroxy-histidine, α-fluoromethyl-histidine, and α-methyl-histidine), amino acids having excess methylenes on the side chain ("homo" amino acids), and amino acids in which the carboxylate functional group amino acid in the side chain is substituted with a sulfonate group (such as cysteic acid). In a preferred aspect, the amino acids contained in the compound of the present invention consist only of natural amino acids.

"The amino acid sequence represented by SEQ ID NO. 1" herein indicates the amino acid sequence of interferon β-1b (see FIG. 16). Interferon β-1b is known to have Met at position 1 deleted an Cys at position 17 substituted to Ser in a natural human interferon β.

When referred to as "having one or a few amino acids deleted, substituted, or added in the amino acid sequence" herein, the number of amino acids to be substituted etc. is not particularly limited as long as interferon β activity is retained, and for example means that about 2, 3, 4, 5, 6, 7, 8, 9, or 10 amino acids are different. Alternatively, it may also include cases where 20% or less, preferably 10% or less amino acids of the entire length of the amino acid sequence are different. The amino acid to be substituted or added may be a natural amino acid, a non-natural amino acid, or an amino acid analog, preferably a natural amino acid. As one aspect of the present invention, a polypeptide "having one or a few amino acids deleted, substituted, or added in the amino acid sequence" includes a natural human interferon β. As described above, the polypeptide consisting of the amino acid sequence represented by SEQ ID NO. 1, i.e. interferon β-1b, has Met at position 1 deleted and Cys at position 17 substituted to Ser in a natural human interferon β. In other words, the natural human interferon β has one amino acid added and one amino acid substituted in a polypeptide consisting of the amino acid sequence represented by SEQ ID NO. 1. Those skilled in the art having seen the specification herein can employ the amino acid sequence of natural human interferon (interferon β-1a) instead of the amino acid sequence of human interferon β-1b employed in the present Examples, and still manufacture and use the present glycosylated peptide similarly to the present invention by referring to the disclosures herein. The amino acid sequence of natural human interferon β-1a is shown as SEQ ID NO. 2. In one aspect of the present invention, when the amino acid sequence of natural human interferon β-1a is used instead of the amino acid sequence of natural human interferon β-1b employed in the present Examples, it is preferred to employ an amino acid sequence that does not have ununiform sugar chains bound at the natural position 80.

An "analog of interferon β" herein includes a polypeptide structurally similar to interferon β and/or a polypeptide having a structure overlapping interferon β, e.g. a polypeptide having one or a few amino acids among the amino acids of interferon β conservatively substituted, a modified interferon β, an interferon β fragment having interferon β activity, and an elongated interferon β having interferon β activity.

"Having one or a few amino acids among the amino acids conservatively substituted" herein refers to an amino acid substitution wherein the hydrophilic index and/or the hydrophobic index between the original amino acid and the amino acid to be substituted are similar, wherein the substitution does not cause apparent reduction or dissipation of interferon β activity between before and after such substitution.

A "modified interferon β" herein is a modified form of interferon β which in naturally-occurring variants of interferon β or artificially modified compounds of interferon β, and such modifications include e.g. alkylation, acylation (such as acetylation), amidation, carboxylation, esterification, disulfide bond formation, glycosylation, lipidation, phosphorylation, hydroxylation, binding of a labeling component, and the like of one or more amino acid residues of interferon β.

An "interferon β fragment having interferon β activity" herein is a peptide that has one or more amino acids added to the N- and/or C-terminal of interferon β and maintains interferon β activity.

An "an elongated interferon β having interferon β activity" herein is a peptide that has one or more amino acids added to the N- and/or C-terminal of interferon and maintains interferon β activity.

The glycosylated polypeptide of the present invention may include a polypeptide consisting of an amino acid sequence having 80% or more homology with the amino acid sequence represented by SEQ ID NO. 1, in which amino acids at 4 to 6 locations are substituted with glycosylated amino acids.

The glycosylated polypeptide of the present invention can be manufactured by integrating a glycosylation step into a peptide synthesis method well-known to those skilled in the art. Although a method utilizing enzymes represented by transglutaminase can also be employed for glycosylation, there are problems in this case such as the need for a large amount of the sugar chain to be added, complication of purification after the final step, and restriction of glycosylation positions and sugar chains that can be added. As a result, although it is possible to employ this in a small-scale synthesis such as for assays, it cannot be said to be a practical method for a large-scale manufacture such as for medicinal manufacturing.

Specific examples of methods which are easy manufacturing methods for the glycosylated polypeptide of the present invention, as well as stable manufacturing methods for a glycosylated polypeptide having uniform sugar chain structure are exemplified as follows: a method of using glycosylated Asn as the glycosylated amino acid, and applying a well-known peptide synthesis method such as solid phase and liquid phase synthesis to thereby manufacture a glycosylated polypeptide (method A); and a method of manufacturing a polypeptide having any amino acid of the polypeptide consisting of the amino acid sequence represented by SEQ ID NO. 1 and the like substituted with Cys according to a well-known peptide synthesis method, and then glycosylating the Cys by chemical synthesis to manufacture a glycosylated polypeptide (method B). Those skilled in the art will be able to manufacture various glycosylated polypeptides by referring to these manufacturing methods, and the glycosylated polypeptides obtained as well as the manufacturing method thereof are extremely useful especially in the field of medicinal manufacturing.

Moreover, these methods A and B can be performed in a combination of two or more. In the case of a small-scale synthesis employed for assays etc., the above method can further be combined with a sugar chain elongation reaction by a transferase. Method A is described in International Publication No. 2004/005330 (US2005222382 (A1)) and method B is described in International Publication No. 2005/010053 (US2007060543 (A1)), the disclosures of which are incorporated herein by reference in their entireties. Moreover, the manufacture of a sugar chain having uniform sugar chain structure employed in methods A and B are described in e.g. International Publication No. 03/008431 (US2004181054 (A1)). International Publication No. 2004/058984 (US2006228784 (A1)), International Publication No. 2004/058824 (US2006009421 (A1)), International Publication No. 2004/070046 (US2006205039 (A1)), and International Publication No. 2007/011055, the disclosures of which are incorporated herein by reference in their entireties.

Method for Manufacturing Glycosylated Polypeptide (Method A)

The glycosylated polypeptide can be manufactured by e.g. solid phase synthesis employing glycosylated Asn outlined below.

(1) The carboxy group of an amino acid having the amino group nitrogen protected with a lipophilic protecting group is bound to a resin. In this case, since the amino group nitrogen of the amino acid is protected with a lipophilic protecting group, self-condensation of amino acids with each other is prevented, and the resin and the amino acid react to produce a bond.

(2) The lipophilic protecting group of the reactant obtained is detached to form a free amino group.

(3) This free amino group and the carboxy group of any amino acid having the amino group nitrogen protected with a lipophilic protecting group are subjected to an amidation reaction.

(4) The lipophilic protecting group is detached to form a free amino group.

(5) The above steps (3) and (4) are repeated once or more times to yield a peptide of any number of any amino acids linked together, having a resin bound on one end and a free amino group on the other end.

(6) Finally, the resin is cleaved with an acid and a peptide having a desired amino acid sequence can be obtained.

Here, if a glycosylated Asn having the amino group nitrogen protected with a lipophilic protecting group is employed instead of the amino acid having the amino group nitrogen protected with a lipophilic protecting group, and the carboxy group of the aforementioned asparagine moiety and the hydroxyl group of the resin are reacted in (1), a peptide having glycosylated Asn at the C-terminal can be obtained.

Moreover, after (2), or after repeating (3) and (4) for any number of times that is once or more, if the glycosylated Asn having the amino group nitrogen protected with a lipophilic protecting group is employed instead of the amino acid having the amino group nitrogen protected with a lipophilic protecting group (3), a sugar chain can be added at any location.

In this manner, by employing a glycosylated Asn having the amino group nitrogen protected with a lipophilic protecting group instead of the amino acid having the amino group nitrogen protected with a lipophilic protecting group two or more times in any of steps (1) and (3), a peptide having sugar chains added at any two or more locations can be obtained.

If, after binding the glycosylated amino acid, the lipophilic protecting group is detached and the free amino group is formed, and step (6) is performed immediately thereafter, a peptide having a glycosylated Asn at the N-terminal can be obtained.

The resin may be resins ordinarily used for solid phase synthesis, and e.g. 2-chlorotrityl chloride resin functionalized with chlorine (from Merck & Co., Inc.), Amino-PEGA resin functionalized with an amino group (from Merck &

Co., Inc.), NovaSyn TGT alcohol resin having a hydroxyl group (from Merck & Co., Inc.), Wang resin (from Merck & Co., Inc.), and HMPA-PEGA resin (from Merck & Co., Inc.) can be employed. Moreover, a linker may be present between the Amino-PEGA resin and the amino acid, and examples of such linkers can include 4-hydroxymethylphenoxyacetic acid (HMPA), 4-(4-hydroxymethyl-3-methoxyphenoxy)-butylacetic acid (HMPB), and the like.

Moreover, when amidating the C-terminal, it is preferred to employ e.g. Rink-Amide-PEGA resin functionalized with an amino group (from Merck & Co., Inc.). By cleaving this resin and the peptide with an acid, the C-terminal amino acid of the peptide can be amidated.

For the binding between a resin and an amino acid having the amino group nitrogen protected with a lipophilic protecting group, for example in order to use a resin having a hydroxyl group or a resin functionalized with chlorine, the carboxy group of the amino acid is subjected to an ester binding with the resin. Further, when using a resin functionalized with an amino group, the carboxy group of the amino acid is bound to the resin by an amide bond.

Any amino acid can be used as the amino acid, examples of which can include the natural amino acids serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenylalanine (Phe), tryptophan (Trp), and proline (Pro).

The D-form of the above natural amino acids can also can be used.

Examples of a lipophilic protecting group can include, e.g., a carbonate- or an amide-based protecting group such as a 9-fluorenylmethoxycarbonyl (Fmoc) group, a t-butyloxycarbonyl (Boc) group, a benzyl group, an allyl group, an allyloxycarbonyl group, and an acetyl group. In order to introduce a lipophilic protecting group into an amino acid, e.g. when introducing an Fmoc group, introduction can be carried out by adding 9-fluorenylmethyl-N-succinimidyl carbonate and sodium hydrogen carbonate and subjecting to reaction. The reaction may be carried out at 0 to 50° C., preferably at room temperature for about 1 to 5 hours.

Those commercially available can also be used as an amino acid protected with a lipophilic protecting group. Examples can include Fmoc-Ser-OH, Fmoc-Asn-OH, Fmoc-Val-OH, Fmoc-Leu-OH, Fmoc-Ile-OH, Fmoc-Ala-OH, Fmoc-Tyr-OH, Fmoc-Gly-OH, Fmoc-Lys-OH, Fmoc-Arg-OH, Fmoc-His-OH, Fmoc-Asp-OH, Fmoc-Glu-OH, Fmoc-Gln-OH, Fmoc-Thr-OH, Fmoc-Cys-OH, Fmoc-Met-OH, Fmoc-Phe-OH, Fmoc-Trp-OH, and Fmoc-Pro-OH.

Moreover, examples of an amino acid protected with a lipophilic protecting group having a protecting group introduced in the side chain can include Fmoc-Arg(Pbf)-OH, Fmoc-Asn(Trt)-OH, Fmoc-Asp(OtBu)-OH, Fmoc-Cys (Acm)-OH, Fmoc-Cys(StBu)-OH, Fmoc-Cys(tBu)-OH, Fmoc-Cys(Trt)-OH, Fmoc-Glu(OtBu)-OH, Fmoc-Gln(Trt)-OH, Fmoc-His(Trt)-OH, Fmoc-Lys(Boc)-OH, Fmoc-Ser (tBu)-OH, Fmoc-Thr(tBu)-OH, Fmoc-Trp(Boc)-OH, and Fmoc-Tyr(tBu)-OH.

Moreover, when a linker is to be added in the amino acid sequence of the glycosylated polypeptide, a linker can be inserted at the preferred position by using a linker protected with a lipophilic protecting group instead of the above amino acid protected with a lipophilic protecting group during the process of solid phase synthesis.

When employing 2-chlorotrityl chloride resin, esterification can be performed by employing a base such as diisopropylethylamine (DIPEA), triethylamine, pyridine, and 2,4,6-collidine. Moreover, when employing a resin having a hydroxyl group, e.g. a well-known dehydration condensing agent such as 1-mesitylenesulfonyl-3-nitro-1,2,4-triazole (MSNT), dicyclohexylcarbodiimide (DCC), and diisopropylcarbodiimide (DIC) can be employed as the esterification catalyst. The proportion of use between the amino acid and the dehydration condensing agent is 1 part by weight of the former to ordinarily 1 to 10 parts by weight, preferably 2 to 5 parts by weight of the latter.

The esterification reaction is preferably performed by e.g. placing a resin in a solid phase column, washing this resin with a solvent, and then adding an amino acid solution. Examples of the washing solvent can include dimethylformamide (DMF), 2-propanol, dichloromethane, and the like. Examples of the solvent for dissolving the amino acid can include dimethyl sulfoxide (DMSO), DMF, dichloromethane, and the like. The esterification reaction may be performed at 0 to 50° C., preferably at room temperature for approximately about 10 minutes to 30 hours, preferably for approximately 15 minutes to 24 hours.

At this time, it is also preferred to cap the unreacted hydroxyl group on the solid phase by acetylation with acetic anhydride and the like.

The detachment of the lipophilic protecting group can be performed by e.g. treating with a base. Examples of the base can include piperidine, morpholine, and the like. It is preferred to perform this in the presence of a solvent. Examples of the solvent can include DMSO, DMF, methanol, and the like.

The amidation reaction between the free amino group and the carboxy group of any amino acid having the amino group nitrogen protected with a lipophilic protecting group is preferably performed in the presence of an activator and a solvent.

Examples of the activator can include dicyclohexylcarbodiimide (DCC), 1-ethyl-3-(3-dimethylaminopropyl)carbodiimide hydrochloride salt (WSC/HCl), diphenylphosphorylazide (DPPA), carbonyldiimidazole (CDI), diethylcyanophosphonate (DEPC), benzotriazol-1-yloxytrispyrrolidinophosphonium (DIPCI), benzotriazol-1-yloxytrispyrrolidinophosphonium hexafluorophospate (PyBOP), 1-hydroxybenzotriazole (HOBt), hydroxysuccinimide (HOSu), dimethylaminopyridine (DMAP), 1-hydroxy-7-axabenzotriazole (HOAt), hydroxyphthalimide (HOPht), pentafluorophenol (Pfp-OH), 2-(1H-benzotriazol-1-yl)-1,1,3,3-tetramethyluronium hexafluorophosphate (HBTU), 1-[bis (dimethylamino)methylene]-5-chloro-1H-benzotriazolium 3-oxide hexafluorophosphate (HCTU), O-(7-azabenzotriazol-1-yl)-1,1,3,3-tetramethyluronium hexafluorophosphate (HATU), O-benzotriazol-1-yl)-1,1,3,3-tetramethyluronium tetrafluoroborate (TBTU), 3,4-dihydro-3-hydrodi-4-oxa-1,2, 3-benzotriazine (Dhbt) and the like.

It is preferred that the amount of the activator used is 1 to 20 equivalents, preferably 1 to 10 equivalents, and further preferably 1 to 5 equivalents to the any amino acid having the amino group nitrogen protected with a lipophilic protecting group.

Examples of the solvent can include DMSO, DMF, dichloromethane, and the like. The reaction may be performed at 0 to 50° C., preferably at room temperature for approximately about 10 to 30 hours, preferably for approximately 15 minutes to 24 hours. The detachment of the lipophilic protecting group can be performed similarly to the above.

Treatment with an acid is preferred for cleaving the peptide chain from the resin. Examples of the acid can include trifluoroacetic acid (TFA), hydrogen fluoride (HF), and the like.

In this way, a glycosylated polypeptide having the desired position substituted by a glycosylated Asn can be obtained.

In one embodiment of the present invention, when the non-reducing terminal on the sugar chain in the glycosylated Asn employed for solid phase synthesis comprises a sialic acid, it is preferred to protect the carboxy group of the aforementioned sialic acid by a protecting group in order to prevent the sialic acid from being cleaved by acid treatment. Examples of the protecting group can include a benzyl group, an allyl group, a diphenylmethyl group, and the like. Methods for introducing the protecting group and detaching the protecting group can be performed by well-known methods.

Method for Manufacturing Glycosylated Polypeptide (Method B)

The glycosylated polypeptide can also be manufactured by a method of first synthesizing a peptide chain, and then later glycosylating the synthesized peptide chain. Specifically, a peptide comprising Cys at the position to be glycosylated is manufactured by solid phase synthesis method, liquid phase synthesis method, a method of synthesizing by a cell, a method of separating and extracting those present in nature, and the like. Cys that is not to be glycosylated such as Cys at the position predetermined to form a disulfide bond is protected here with e.g. an acetoamidomethyl (Acm) group. Moreover, when introducing Cys that is not to be glycosylated and not used for forming a disulfide bond into the glycosylated polypeptide, it can be introduced by protecting the Cys with a protecting group during the glycosylation step and the disulfide bond formation step, and then deprotecting it. Examples of such a protecting group can include tert-butyl (tBu) and 4-methoxybenzyl.

In addition, when adding a different sugar chain to the Cys in the glycosylated polypeptide, a different sugar chain can be introduced by first rendering the Cys for introducing a sugar chain to be in an unprotected state, and then protecting the Cys for introducing a different sugar chain by StBu and the like. Specifically, when synthesizing the peptide by solid phase synthesis etc., the Cys for introducing a first sugar chain is rendered unprotected, and the Cys for introducing a second sugar chain is rendered to be Cys having a protecting group such as StBu is still retained. A different sugar chain can then be introduced into the Cys rendered unprotected by deprotecting the StBu group etc. The Cys for introducing the first sugar chain and the Cys for introducing the second sugar chain can be one or more.

The deprotection of the StBu group can be performed by subjecting to a reaction with a reductant such as tris(2-carboxyethyl)phosphine hydrochloride salt (TCEP), dithiothreitol (DTT), and tributylphosphine. The above reaction may be performed ordinarily at 0 to 80° C., preferably at 5 to 60° C., and further preferably at 10 to 35° C. Preferably, the reaction time is ordinarily approximately 30 minutes to 5 hours. Upon completion of the reaction, this may be purified with a well-known method (such as high performance liquid column chromatography (HPLC)) as appropriate.

When a linker is to be added in the amino acid sequence of the glycosylated polypeptide, a linker can be inserted at the preferred position of the synthesized polypeptide by e.g. using a linker protected with a lipophilic protecting group instead of the amino acid protected with a lipophilic protecting group during the process of solid phase synthesis.

Next, by reacting a haloacetylated complex sugar chain derivative with the peptide comprising an unprotected Cys obtained above, the sugar chain is reacted with the thiol group of the unprotected Cys and bound to the peptide. The above reaction may be performed in a phosphate buffer, a tris-hydrochloride buffer, a citrate buffer, or a mixed solution thereof, ordinarily 0 to 80° C., preferably at 10 to 60° C., and further preferably at 15 to 35° C. Preferably, the reaction time is ordinarily 10 minutes to 24 hours, and preferably, ordinarily approximately 30 minutes to 5 hours. Upon completion of the reaction, this may be purified with a well-known method (such as HPLC) as appropriate.

The haloacetylated complex sugar chain derivative is e.g. a compound having the hydroxyl group bound to the carbon at position 1 of a complex asparagine-linked sugar chain substituted with —NH—$(CH_2)_a$—(CO)—$CH_2X$ (wherein X indicates a halogen atom, and a indicates an integer which is not limited as long as it does not inhibit the target linker function, but is preferably an integer from 0 to 4).

Specifically, the haloacetylated complex sugar chain derivative and the Cys-containing peptide are reacted in a phosphate buffer at room temperature. Upon completion of the reaction, the glycosylated polypeptide substituted with a glycosylated Cys can be obtained by purification with HPLC.

The reaction can also be performed in a mixed solution of an organic solvent such as DMSO, DMF, methanol, and acetonitrile with the above buffer. In the case, the organic solvent can be added to the above buffer at a ratio in the range of 0 to 99% (v/v). Since the addition of such organic solvent can improve the solubility against the reaction solution, this is preferred for a peptide comprising unprotected Cys with low solubility against the buffer.

The reaction can also be performed in an organic solvent such as DMSO, DMF, methanol, and acetonitrile or a mixed solution thereof. In the case, it is preferred to be performed in the presence of a base. Examples of the base can include DIPEA, triethylamine, pyridine, 2,4,6-collidine, and the like.

The reaction can also be performed in a mixed solution of guanidine hydrochloride or urea added to the buffer solution. Guanidine hydrochloride or urea can be added to the above buffer so that the final concentration will be 1 M to 8 M. This is preferred since the addition of guanidine hydrochloride or urea can also improve the solubility of peptide with low solubility against the buffer.

Further, the reaction can also be performed with addition of tris(2-carboxyethyl)phosphine hydrochloride salt (TCEP) or dithiothreitol (DTT) to the buffer in order to prevent the formation of a dimer of peptides comprising unprotected Cys via a disulfide bond. TCEP or DTT can be added to the buffer so that the final concentration will be 10 μM to 10 mM.

Moreover, after the sugar chain is bound to the target Cys, the protecting group of Cys protected with Acm and the like is deprotected. When the protecting group is an Acm group, deprotection can be performed by allowing reaction with iodine, mercury acetate (II), silver nitrate (I), or silver acetate (I), and the like in water, methanol, acetic acid, or a mixed solution thereof.

The above reaction may be performed ordinarily at 0 to 80° C., preferably at 5 to 60° C., and further preferably at 10 to 35° C. Preferably, the reaction time is ordinarily approximately 5 minutes to 24 hours. Upon completion of the reaction, this may be purified with a well-known method (such as HPLC) as appropriate after treatment with DTT or hydrochloric acid and the like.

In this way, a glycosylated polypeptide having the desired position substituted with a glycosylated Cys can be obtained. Moreover, as described below, the glycosylated polypeptide purified as such will form a disulfide bond between deprotected Cys.

Moreover, when manufacturing a glycosylated polypeptide having multiple sialic acid-containing sugar chains such as disialo or monosialo sugar chains in the peptide sequence, a sialic acid-containing sugar chain having the carboxy group of the sialic acid on the sugar chain to be introduced protected with a benzyl (Bn) group, an allyl group, a diphenylmethyl group, a phenacyl group, and the like can be employed.

When a sugar chain having the carboxy group of the sialic acid protected is introduced, a step of deprotecting the sialic acid protecting group can be performed after the step of forming a disulfide bond in the glycosylated polypeptide.

In this way, by protecting the carboxy group of the sialic acid with a benzyl group and the like, the separation/purification step by HPLC etc. in the manufacturing step will be facilitated. The protection of the carboxy group of the sialic acid will also enable prevention of detachment of an acid-labile sialic acid.

The protection reaction of the carboxy group of the sialic acid on the sugar chain can be performed by a method well-known to those skilled in the art. Moreover, in the glycosylated polypeptide that has formed a disulfide bond, the protecting group of the carboxy group of the sialic acid can be deprotected by hydrolysis under basic conditions. The above reaction may be performed ordinarily at 0 to 50° C., preferably at 0 to 40° C., and further preferably at 0 to 30° C. Preferably, the reaction time is ordinarily approximately 5 minutes to 5 hours. Upon completion of the reaction, this may be purified with a well-known method (such as HPLC) as appropriate after neutralization by a weak acid such as phosphoric acid or acetic acid.

Moreover, the glycosylated polypeptide created by the above methods A and B can form a disulfide bond between Cys with a method well-known to those skilled in the art employing air and/or oxygen, iodine, DMSO, a mixture of oxidated and reduced glutathione, potassium ferricyanide, Ellman's reagent (5,5'-dithiobis(2-nitrobenzoic acid)), thallium trifluoroacetate (III), alkyltrichlorosilane sulfoxide, and the like.

When forming a disulfide bond between Cys-Cys, Cys in a glycosylated polypeptide that is not desired to form a disulfide bond is protected by a protecting group. A protecting group stable under oxidizing conditions such as Acm, tBu, 4-methoxybenzyl, 4-methylbenzyl, and the like can be employed as such a protecting group.

In method B, the formation of a disulfide bond can also be performed before the introduction of the sugar chain. However, when a protecting group is introduced in the Cys to form a disulfide bond, the deprotection step will precede the disulfide bond formation step.

(Activity)

The glycosylated polypeptide of the present invention has interferon β activity. "Interferon β activity" herein means having at least one activity among well-known activities such as immunoregulatory action, anti-viral activity, and antitumor activity.

For example, interferon β activity of the glycosylated polypeptide can be measured with the antitumor activity measurement test described in Examples 11 to 14 and the like.

The antitumor activity measurement test can be examined by e.g. subcutaneously administering the subject glycosylated polypeptide to mice processing a tumor and measuring the tumor volume over time.

(Pharmaceutical Composition)

A pharmaceutical composition containing the glycosylated polypeptide of the present invention as the active ingredient is effective for therapy or prevention of a disease related to interferon β. Examples of a disease related to interferon β include brain tumor, cutaneous malignant melanoma, chronic active hepatitis B, chronic hepatitis C, subacute sclerosing panencephalitis, compensated cirrhosis C, multiple sclerosis, and the like. The above brain tumor includes glioblastoma, medulloblastoma, astrocytoma, and the like. The pharmaceutical composition containing the glycosylated polypeptide of the present invention as the active ingredient is effective for therapy or prevention of the above disease.

Moreover, the administration subject of the pharmaceutical composition containing the glycosylated polypeptide of the present invention as the active ingredient means any biological individual, preferably an animal, further preferably a mammal, and further preferably a human individual.

The above pharmaceutical composition is those formulated into an ordinary pharmaceutical composition from with a diluent or an excipient such as ordinarily used fillers, expanders, binders, wetting agents, disintegrants, surfactants, lubricants, and the like.

Examples of such pharmaceutical compositions include tablets, pills, powders, liquids, suspensions, emulsions, granules, capsules, suppositories, inhalant, ophthalmic solutions, injections, and the like.

The amount of the glycosylated polypeptide of the present invention contained in the pharmaceutical composition is not particularly limited and may be selected as appropriate from a broad range. It is ordinarily preferred to contain 1 to 90% by weight, more preferably contain 1 to 70% by weight of the glycosylated polypeptide of the present invention in the pharmaceutical composition.

The pharmaceutical composition containing the glycosylated polypeptide of the present invention as the active ingredient may further contain other active ingredients, or can also be employed in combination with a pharmaceutical composition containing other active ingredients. Moreover, the pharmaceutical composition containing the glycosylated polypeptide of the present invention as the active ingredient can comprise the glycosylated polypeptide as a pharmaceutically acceptable salt, or it can also comprise one or more further different glycosylated polypeptide of the present invention as the active ingredient. It can also be employed in combination with one or more different pharmaceutical composition containing the glycosylated polypeptide of the present invention as the active ingredient. Moreover, other ingredients that can be contained in the pharmaceutical composition can include a pharmaceutically acceptable carrier and the like known to those skilled in the art.

The administration method of the pharmaceutical composition according to the present invention is not particularly restricted, and it is administered in a method that complies with various drug formulations, the patient's age, sex, disease state, and other conditions. An example of the administration method in the case of tablets, pills, liquids, suspensions, emulsions, granules, and capsule includes oral administration. Further, in the case of injections, it can be intravenously, intramuscularly, intradermally, subcutaneously, or intraperitoneally administered alone or in a mixture with ordinary fluid replacements such as glucose and amino acids. In the case of suppositories, it is rectally administered. In the case of ophthalmic solutions, it is applied to the eye tissue such as the conjuctival sac. In the case of inhalants, it is applied to the bronchial tube or the lung.

The dosage of the above pharmaceutical composition may be selected as appropriate according to usage, the patient's age, sex, the extent of disease, and other conditions. For example, the dosage can be 0.001 to 100 nmol, preferably 0.01 to 10 nmol, and more preferably 0.01 to 1 nmol of the glycosylated polypeptide of the present invention per 1 kg of body weight.

The administration frequency of the above pharmaceutical composition may be selected as appropriate according to usage, the patient's age, sex, the extent of disease, and other conditions. For example, an administration frequency that is three times/day, twice/day, once/day, or further an even less frequency depending on its stability in blood (such as once/week or once/month) may also be selected. The administration frequency of the above pharmaceutical composition is preferably once or less/day.

The sugar chain added to the glycosylated polypeptide of the present invention is easily degraded by the metabolic system in the body. Moreover, in one aspect of the present invention, said sugar chain has a structure that exists as bound to a glycopeptide (or a glycoprotein) in vivo. Accordingly, a pharmaceutical composition that comprises the glycosylated polypeptide of the present invention and the aforementioned glycosylated polypeptide as active ingredients has advantages such as not showing side effects or antigenicity even when administered in vivo, and causing less concerns for losing drug effect due to allergic reactions or antibody production.

Further, the glycosylated polypeptide of the present invention is also extremely useful with respect to enabling stable and easy large-scale supply, and providing high quality medicine with stable quality.

The terms used herein are to be employed to describe particular embodiments, and do not intend to limit the invention.

The term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and shall not be construed as having idealized or excessively formal meanings.

Terms such as first and second are sometimes employed to express various elements, and it should be recognized that these elements are not to be limited by these terms. These terms are employed solely for the purpose of discriminating one element from another, and it is for example possible to describe a first element as a second element, and similarly, to describe a second element as a first element without departing from the scope of the present invention.

The present invention will now be more specifically described by Examples. However, the present invention can be embodied by various forms, and shall not be construed as being limited to the Examples described herein.

EXAMPLES

The notation system of the polypeptide fragments herein will be described below.

For example, IFN 1-78(S1Thi-C30Acm)MESNA indicates a peptide fragment that has a peptide sequence equivalent to the 1st-78th amino acid sequence in the amino acid sequence represented by SEQ ID NO. 1, wherein the 1st serine is substituted to cysteine having a thiazolidine structure, the side chain of the 30th cysteine is protected by Acm, and the C-terminal is alkylthioesterified by 2-mercaptoethanesulfonate (MESNA) in its peptide sequence.

Moreover, IFN 1-78(S1Thi-C30Acm-Q48C)MESNA indicates a peptide fragment that has a peptide sequence equivalent to the 1st-78th amino acid sequence in the amino acid sequence represented by SEQ ID NO. 1, wherein the 1st serine is substituted to cysteine having a thiazolidine structure, the side chain of the 30th cysteine is protected by Acm, the 35th methionine is substituted to cysteine, the 48th glutamine is substituted to cysteine, and the C-terminal is alkylthioesterified by 2-mercaptoethanesulfonate (MESNA) in its peptide sequence.

Similarly, IFN 1-78(S1Thi-C30Acm-Q48C)Ethan indicates a peptide fragment that has a peptide sequence equivalent to the 1st-78th amino acid sequence in the amino acid sequence represented by SEQ ID NO. 1, wherein the 1st serine is substituted to cysteine having a thiazolidine structure, the side chain of the 30th cysteine is protected by Acm, the 48th glutamine is substituted to cysteine, and the C-terminal is alkylthioesterified by ethanthiol in its peptide sequence.

Moreover, IFN 79-165(N79C-K107C-R112C-R123C-C140Acm) indicates a peptide fragment that has a peptide sequence equivalent to the 79th-165th amino acid sequence in the amino acid sequence represented by SEQ ID NO. 1, wherein the 79th asparagine is substituted to cysteine, the 107th lysine is substituted to cysteine, the 112nd lysine is substituted to cysteine, the 123rd arginine is substituted to cysteine, and the 140th cysteine is protected by an Acm group in its peptide sequence.

The notation system of glycosylated polypeptides will be described below.

For example, 2-6 diSialo(S1C-Q48C-N79C-K107C-R112C-R123C) indicates that each amino acid of serine at position 1, glutamine at position 48, asparagine at position 79, lysine at position 107, arginine at position 112, and arginine at position 123 in the amino acid sequence represented by SEQ ID NO. 1 is substituted to Cys, and the α2-6 disialo sugar chain structure shown in the following Formula (1) is bound to Cys in each substitution.

[Chemical Formula 13]

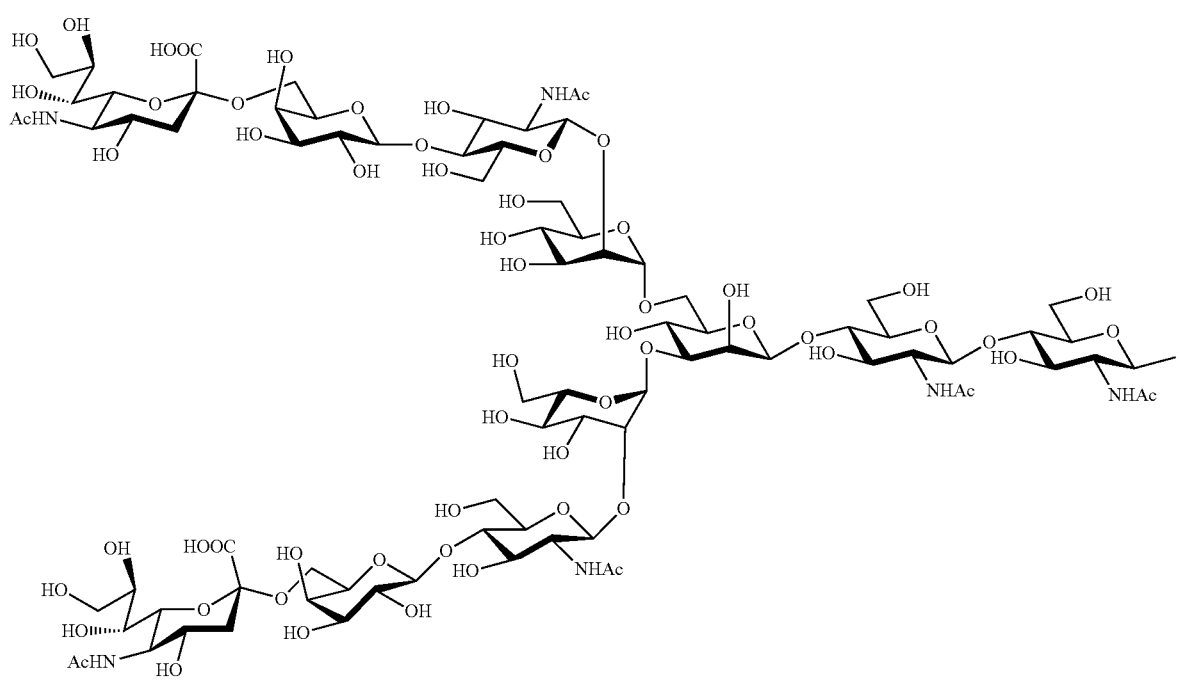

Formula(1)

Moreover, 2-3diSialo(S1C-Q48C-N79C-K107C-R112C-R123C) indicates that each amino acid of serine at position 1, glutamine at position 48, asparagine at position 79, lysine at position 107, arginine at position 112, and arginine at position 123 in the amino acid sequence represented by SEQ ID NO. 1 is substituted to Cys, and the α2-3disialo sugar chain structure shown in the following Formula (2) is bound to Cys in each substitution.

[Chemical Formula 14]

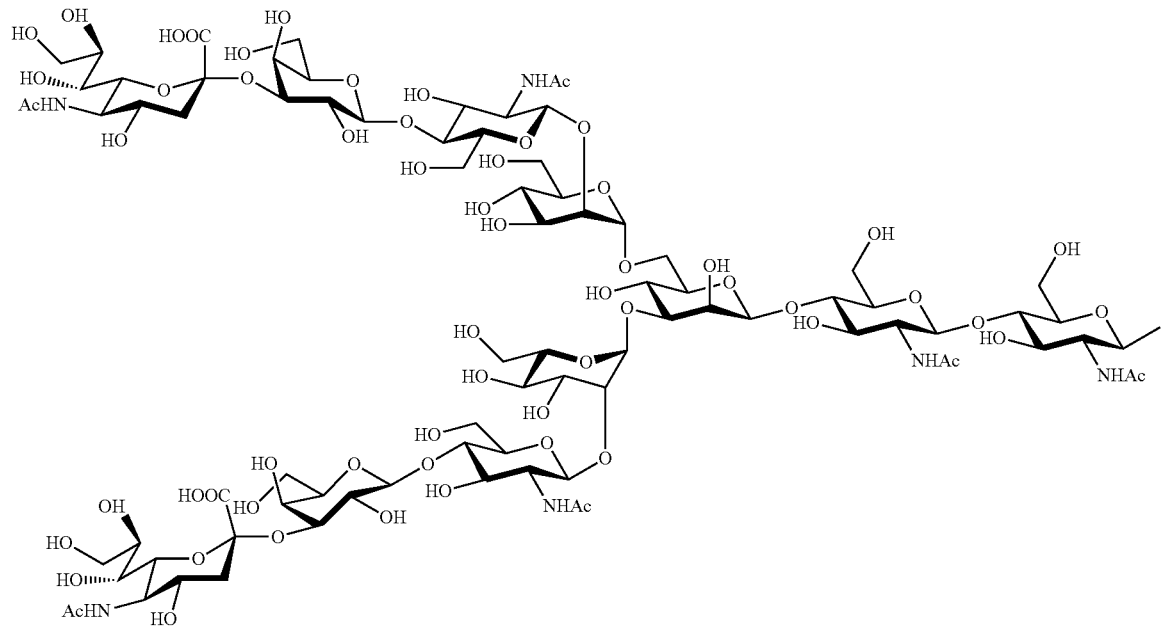

Formula (2)

Moreover, 2-6 monoSialo(S1C-Q48C-N79C-K107C-R112C-R123C) indicates that each amino acid of serine at position 1, glutamine at position 48, asparagine at position 79, lysine at position 107, arginine at position 112, and arginine at position 123 in the amino acid sequence represented by SEQ ID NO. 1 is substituted to Cys, and the α2-6 monosialo sugar chain structure shown in the following Formula (5) or (6) is bound to Cys in each substitution.

[Chemical Formula 15]

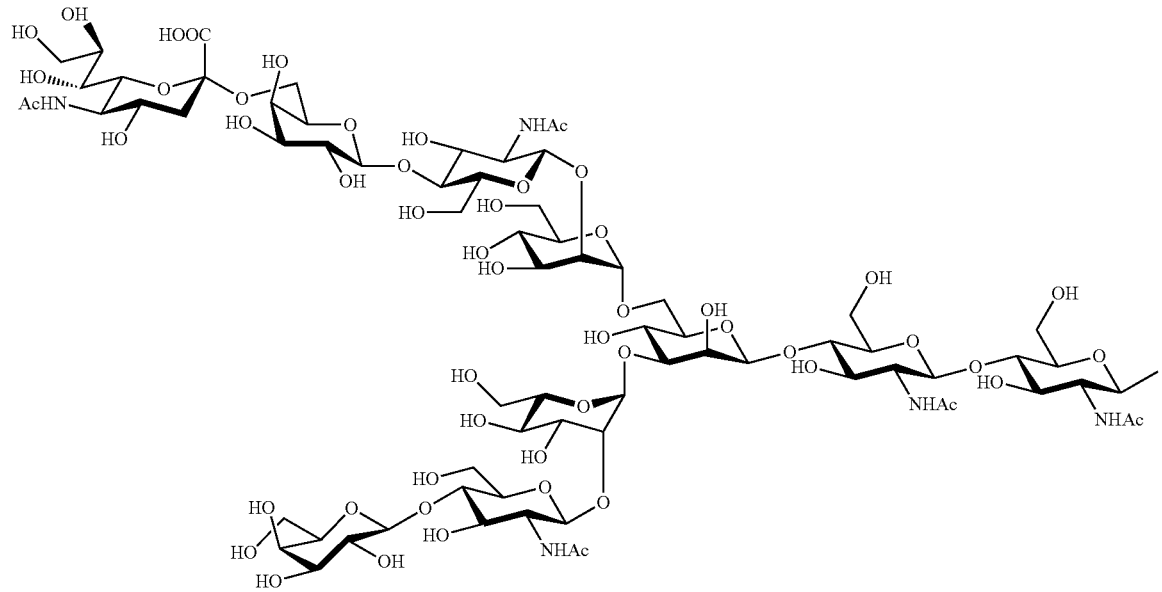

Formula (5)

[Chemical Formula 16]

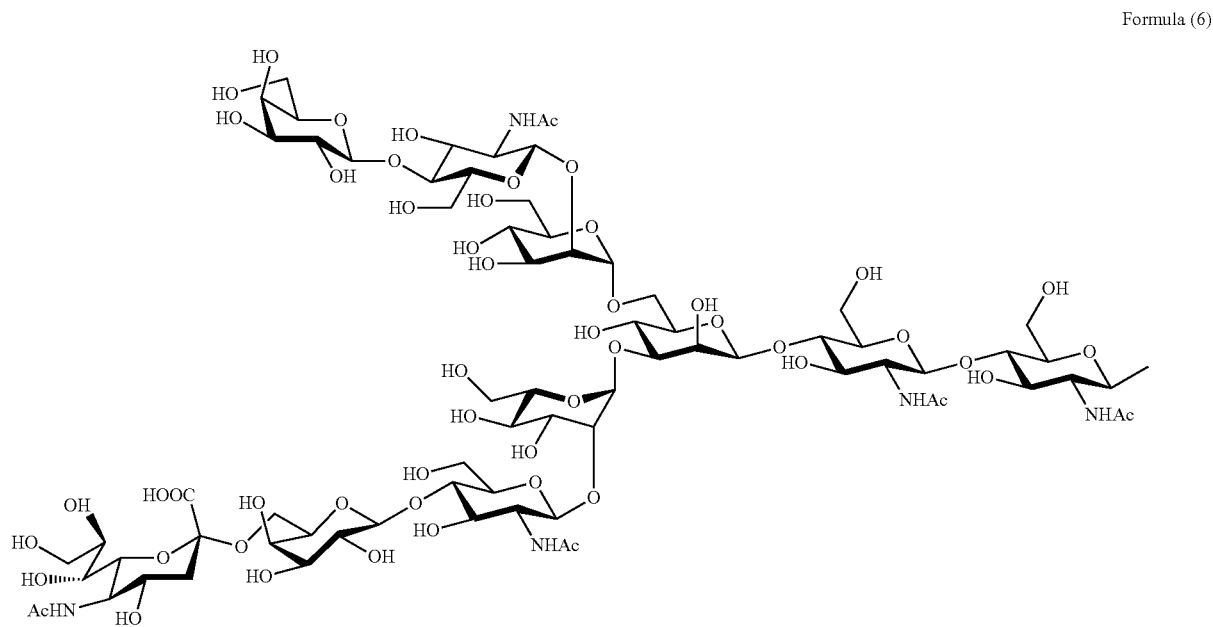

Formula (6)

Moreover, 2-6 triSialo(S1C-Q48C-N79C-R112C-R123C) indicates that each amino acid of serine at position 1, glutamine at position 48, asparagine at position 79, lysine at position 107, arginine at position 112, and arginine at position 123 in the amino acid sequence represented by SEQ ID NO. 1 is substituted to Cys, and the α2-6 trisialo sialo sugar chain structure shown in the following Formula (3) is bound to Cys in each substitution.

[Chemical Formula 17]

Formula (3)

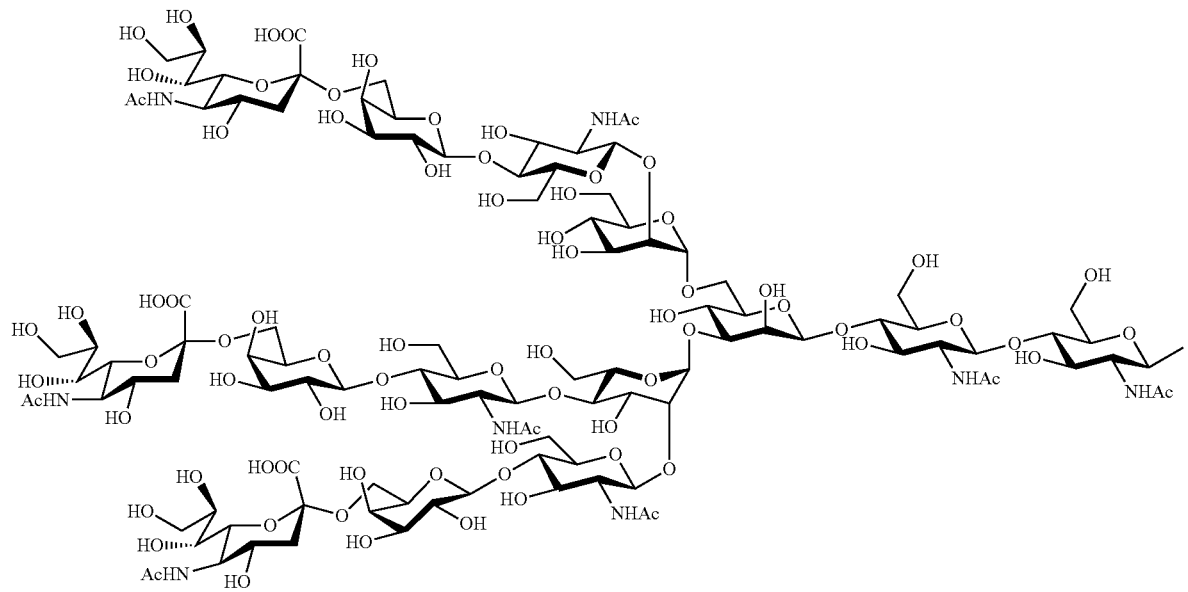

Moreover, 2-6 tetraSialo(S1C-Q48C-N79C-K107C-R112C-R123C) indicates that each amino acid of serine at position 1, glutamine at position 48, asparagine at position 79, lysine at position 107, arginine at position 112, and arginine at position 123 in the amino acid sequence represented by SEQ ID NO. 1 is substituted to Cys, and the α2-6 tetrasialo sugar chain structure shown in the following Formula (4) is bound to Cys in each substitution.

[Chemical Formula 18]

Formula (4)

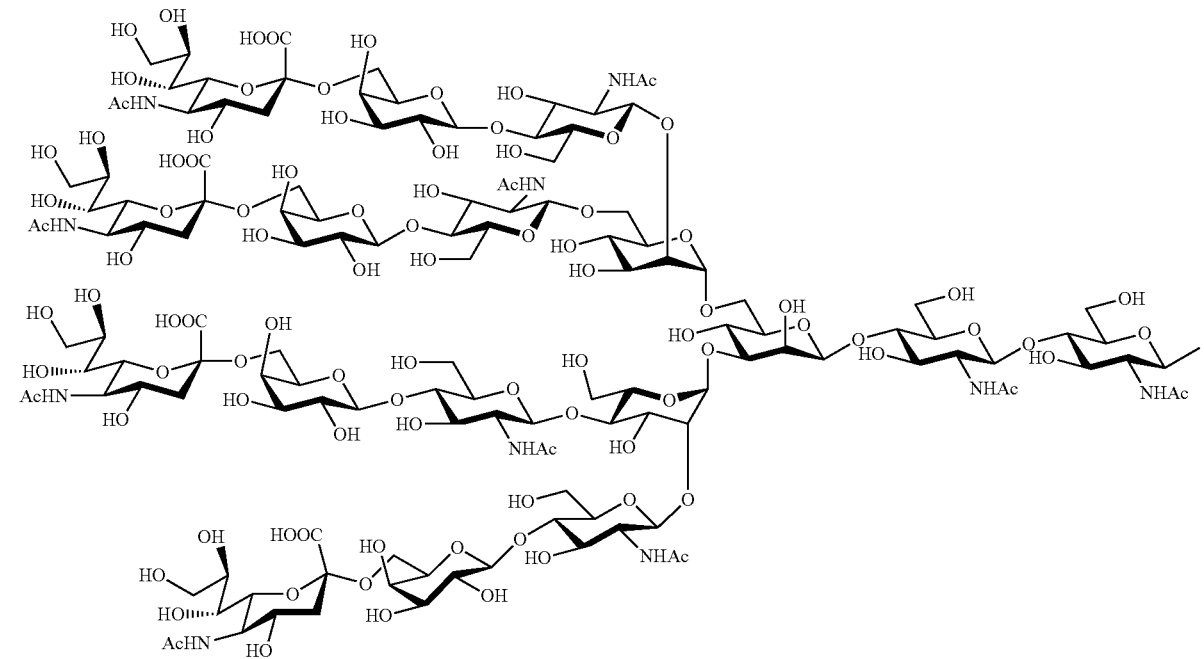

The structure of a sugar chain structure bound to Cys is shown in the following Formula (14) with α2-6 disialo sugar chain as an example. In the following formula, wave lines indicate that drawings of adjacent amino acids bound by peptide bonds to the cysteine drawn at the right edge of the following formula are omitted.

[Chemical Formula 19]

Formula(14)

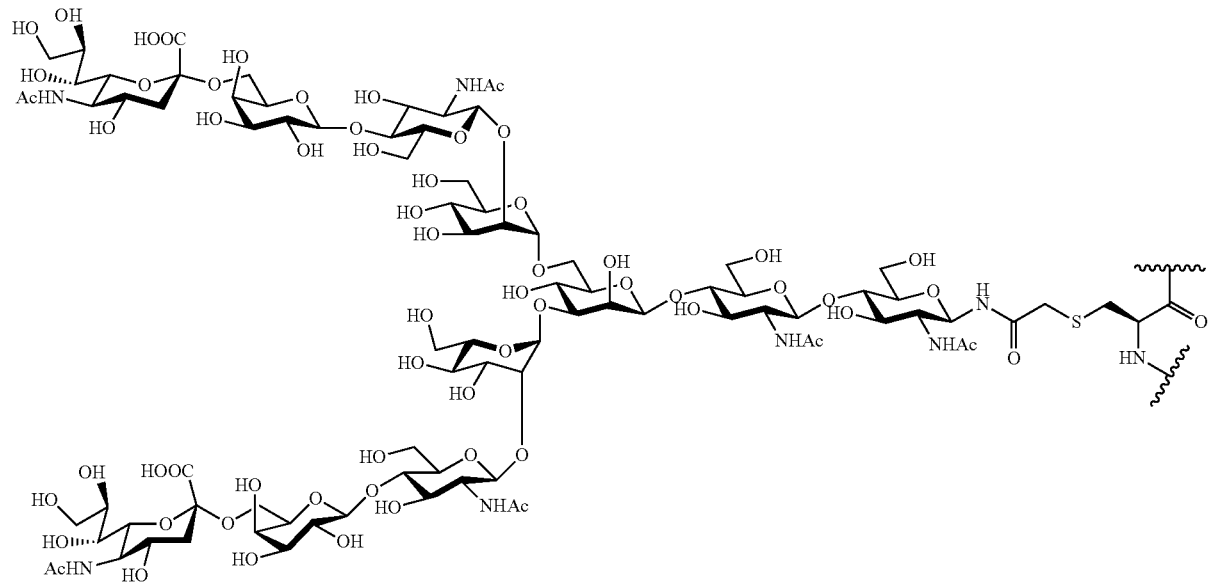

"DiSialo" means a disialo sugar chain, "monoSialo" means a monosialo sugar chain, "triSialo" means a trisialo sugar chain, and "tetraSialo" means a tetrasialo sugar chain.

Moreover, 2-6 diSialo(S1C-Q48C-N79-K107C-R112C-R123C) indicates that each amino acid of serine at position 1, glutamine at position 48, lysine at position 107, arginine at position 112, and arginine at position 123 in the amino acid sequence represented by SEQ ID NO. 1 is substituted to Cys, and the α2-6 disialo sugar chain structure shown in the following Formula (1) is bound to Cys in the above each substitution and asparagine at position 79.

[Chemical Formula 20]

Formula (1)

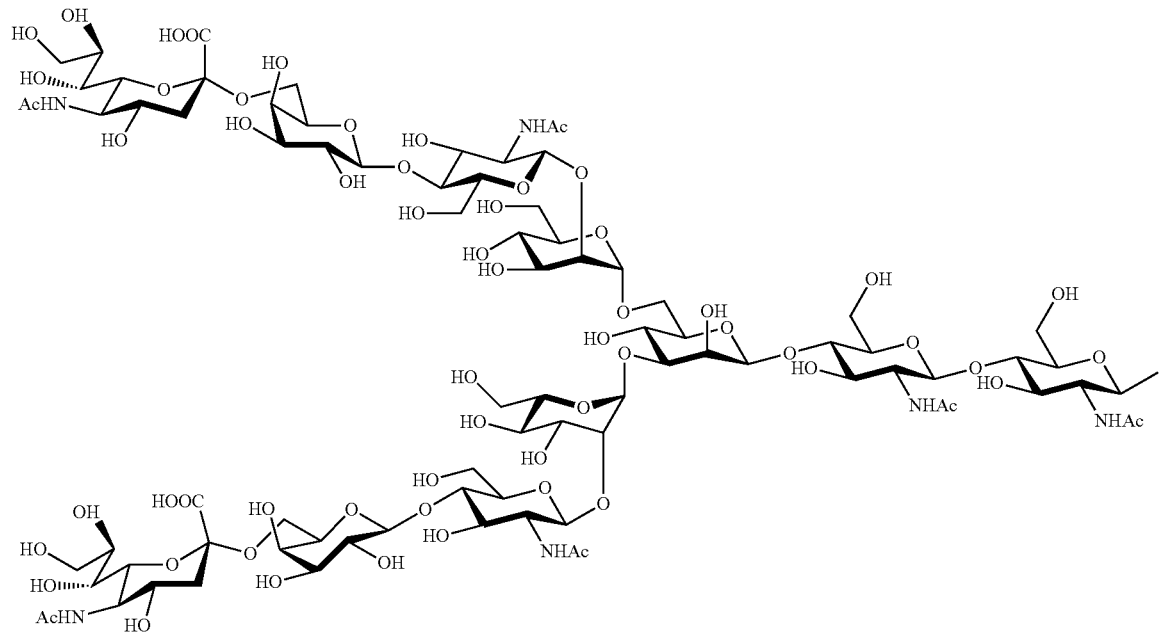

Moreover, in the following Examples, IFN-β having amino acids at 4, 5, and 6 locations substituted with glycosylated amino acids may be represent as "quadruple, quintuple, and sextuple-glycosylated IFN-β," respectively. In the present invention, "a glycosylated polypeptide having amino acids at 4 locations substituted with glycosylated amino acids" and "a quadruple-glycosylated IFN-β" are synonymous, and similarly, "a glycosylated polypeptide having amino acids at 5 locations substituted with glycosylated amino acids" and "a quintuple-glycosylated IFN-β" are synonymous, and similarly, "a glycosylated polypeptide having amino acids at 6 locations substituted with glycosylated amino acids" and "a sextuple-glycosylated IFN-β" are synonymous.

Example 1

Synthesis of Thioester Fragments

Example 1-1

Synthesis of IFN 1-78(S1Thi-C30Acm-Q48C)Ethan SEQ ID NO. 3)

Amino-PEGA resin (from Merck & Co., Inc.) (50 μmol) was added onto a column for solid phase synthesis, 4-hydroxymethyl-3-methoxyphenoxy butyric acid (HMPB) (125 μmol), O-benzotriazol-1-yl-1,1,3,3-tetramethyluronium tetrafluoroborate (TBTU) (125 μmol), and N-ethylmorpholine (125 μmol) were dissolved in dimethylformamide (DMF) (125 ml), and stirred at room temperature for 4 hours. The resin was sufficiently washed with DMF and dichloromethane (DCM). Subsequently, Fmoc-Trp(Boc)-OH (0.25 mmol), 1-mesitylenesulfonyl-3-nitro-1,2,4-triazole (MSNT) (0.25 mmol), and N-methylimidazole (0.187 mmol) were dissolved DCM (1.25 ml) and added to the column for solid phase synthesis, and then stirred for 4 hours.

The resin was washed with DCM and DMF, and the Fmoc group was treated for 15 minutes with 20% piperidine/DMF solution (2 ml) to allow deprotection. This was washed with DMF, and the subsequent peptide chain elongation employed the method shown below to sequentially condense amino acids.

The amino acid protected with an Fmoc or Boc group was dissolved in DMF, and the solution was added to the solid phase synthesis column (0.25 mmol). 0.2 M 1-[bis(dimethylamino)methylene]-5-chloro-1H-benzotriazolium 3-oxide hexafluorophosphate (HCTU)/DMF (0.25 mmol) was added to the solid phase synthesis column, and 0.8 M N-methyl morpholine/DMF (0.50 mmol) or 0.8 M 2,6,4-trimethylpyridine/DMF (0.50 mmol) was added to the column for solid phase synthesis. After stirring at room temperature for 15 or 30 minutes, the resin was washed with DMF, and the Fmoc group was treated for 10 minutes with 20% piperidine/DMF solution (2 ml) to allow deprotection. This operation was repeated, and amino acids were sequentially condensed by Fmoc solid phase synthesis method.

After washing the resin obtained with DCM and DMF, a mixed solution of trifluoroethanol and acetic acid (1:1) was added, and the protected peptide was separated from the resin by stirring for 18 hours at room temperature. The reaction solution comprising the protected peptide was concentrated under reduced pressure, and then dried under reduced pressure. The dried protected peptide was dissolved in DMF (3.0 mL), and then cooled under nitrogen atmosphere to −15° C. to −20° C. To this was added ethanthiol (5.0 mmol), and then benzotriazol-1-yloxy-trispyrrolidinophosphonium hexafluorophospate (PyBOP) (0.50 mmol), then diisopropylethylamine (DIPEA) (0.5 mmol) were added. After stirring at −15° C. to −20° C. for 2 hours, acetic acid (0.8 mL) was added, and this was allowed to gradually return to room temperature. When the temperature was back to room temperature, the reaction solution was concentrated under reduced pressure. To the residue obtained was added trifluoroacetic acid:water:phenol:thioanisole:triisopropylsilane (=95:2.5:2.5:2.5:5), and this was stirred at room temperature. After 2 hours, this solution was again added to a separately prepared diethyl ether and allowed to precipitate, then subjected to centrifugal separation, and the solution portion was removed to obtain a residue comprising the target peptide thioester form. This residue obtained was purified with HPLC [column: SHISEIDO Proteonavi], and as a result of mass analysis by ESI-MS, the mass of the compound obtained corresponded with the mass of the target IFN 1-78(S1Thi-C30Acm-Q48C)Ethan (calculated value=9445.8 Da, actual value=9445.5 Da).

Example 1-2

Synthesis of IFN 1-78(S1Thi-C30Acm-Q48C-S75C)MESNA (SEQ ID NO. 4)

Amino-PEGA resin (from Merck & Co., Inc.) (50 μmol) was added onto a column for solid phase synthesis, 3-Fmoc-4-diaminobenzoic acid (150 μmol) 1-[bis(dimethylamino)methylene]-5-chloro-1H-benzotriazolium 3-oxide hexafluorophosphate (HCTU) (150 μmol), and diisopropylethylamine (300 μmol) were dissolved in DMF (1.25 ml), and stirred at room temperature for 2 hours.

After stirring the resin was washed with DMF, the Fmoc group was treated for 15 minutes with 20% piperidine/DMF solution (2 ml) to allow deprotection, and then the resin was sufficiently washed with DMF. Amino acids were sequentially condensed in the subsequent peptide chain elongation employing the method shown below.

The amino acid protected with an Fmoc or Boc group was dissolved in DMF, and the solution was added to tic solid phase synthesis column (0.25 mmol). 0.2 M 1-[bis(dimethylamino)methylene]-5-chloro-1H-benzotriazolium 3-oxide hexafluorophospate (HCTU)/DMF (0.25 mmol) was added to the solid phase synthesis column, and 0.8 M N-methyl morpholine/DMF (0.50 mmol) or 0.8 M 2,6,4-trimethylpyridine/DMF (0.50 mmol) was added to the column for solid phase synthesis. After stirring at room temperature for 15 or 30 minutes, the resin was washed with DMF, and the Fmoc group was treated for 10 minutes with 20% piperidine/DMF solution (2 ml) to allow deprotection. This operation was repeated, and amino acids were sequentially condensed by Fmoc solid phase synthesis method.

After washing the resin obtained with DMF and DCM, 4-Nitrophenyl Chloroformate (0.25 mmol) was dissolved in DCM, added to the solid phase synthesis column, and then stirred at room temperature for 30 minutes. After stirring, the resin was washed with DCM and DMF, diisopropyl (2.5 mmol) was added, and stirred at room temperature for 15 minutes. After washing the resin obtained with DMF and DCM, trifluoroacetic acid:water:phenol:thioanisole:triisopropylsilane (=95:2.5:2.5:2.5:5) was added, and this was stirred at room temperature. After 5 hours, the resin was sufficiently washed with a buffer solution at pH 7.2 comprising sodium 2-mercaptoethanesulfonate (8 M guanidine hydrochloric acid solution, 0.1 M phosphoric acid solution, and 300 mM sodium 2-mercaptoethanesulfonate). The above buffer was added to the resin, and stirred at room temperature for 12 hours.

After stirring, the solution obtained was purified with HPLC [column: SHISEIDO Proteonavi], and as a result of mass analysis by ESI-MS, the mass of the compound obtained corresponded with the mass of the target IFN 1-78(S1Thi-C30Acm-Q48C-N75C)MESNA (calculated value=9540.9 Da, actual value=9541.6 Da).

Example 1-3

Synthesis of Other Thioester Fragments

Thioester fragments shown below were synthesized similarly to (Example 1-1).

IFN 1-78(S1Thi-N3C-C30Acm-Q48C)Ethan (SEQ ID NO. 5)
IFN 1-78(S1Thi-E28C-C30Acm-Q48C-R70C)Ethan (SEQ ID NO. 6)

The following thioester fragments were synthesized similarly to (Example 1-2).
IFN 1-78(C30Acm)MESNA (SEQ ID NO. 7)
IFN 1-78(S1Thi-C30Acm)MESNA (SEQ ID NO. 8)
IFN 1-78(F7C-C30Acm)MESNA (SEQ ID NO. 9)
IFN 1-78(N24C-C30Acm)MESNA (SEQ ID NO. 10)
IFN 1-78(G25C-C30Acm)MESNA (SEQ ID NO. 11)
IFN 1-78(E28C-C30Acm)MESNA (SEQ ID NO. 12)
IFN 1-78(C30Acm-K32C)MESNA (SEQ ID NO. 13)
IFN 1-78(C30Acm-M35C)MESNA (SEQ ID NO. 14)
IFN 1-78(C30Acm-D38C)MESNA (SEQ ID NO. 15)
IFN 1-78(C30Acm-E41C)MESNA (SEQ ID NO. 16)
IFN 1-78(C30Acm-Q48C)MESNA (SEQ ID NO. 17)
IFN 1-78(C30Acm-R70C)MESNA (SEQ ID NO. 18)
IFN 1-78(C30Acm-S75C)MESNA (SEQ ID NO. 19)
IFN 1-78(C30Acm-E41C-S75C)MESNA (SEQ ID NO. 20)
IFN 1-78(C30Acm-E42C-S75C)MESNA (SEQ ID NO. 21)
IFN 1-78(C30Acm-Q45C-S75C)MESNA (SEQ ID NO. 22)
IFN 1-78(C30Acm-L46C-S75C)MESNA (SEQ ID NO. 23)
IFN 1-78(C30Acm-Q47C-S75C)MESNA (SEQ ID NO. 24)
IFN 1-78(C30Acm-Q48C-S75C)MESNA (SEQ ID NO. 25)
IFN 1-78(C30Acm-F49C-S75C)MESNA (SEQ ID NO. 26)
IFN 1-78(C30Acm-Q50C-S75C)MESNA (SEQ ID NO. 27)
IFN 1-78(S1Thi-Y29C-C30Acm-Q48C)MESNA (SEQ ID NO. 28)
IFN 1-78(S1Thi-C30Acm-M35C-Q48C)MESNA (SEQ ID NO. 29)
IFN 1-78(S1Thi-C30Acm-E41C-Q48C)MESNA (SEQ ID NO. 30)

Mass spectrometry results of compounds combined in (Example 1-1), (Example 1-2), and (Example 1-3) are shown in (Table 1) below.

TABLE 1

| Example | Compound | Theoretical value (MW) | Actual value (MW) | Ionization method |
| --- | --- | --- | --- | --- |
| 1-1 | IFN I-78 (S1Thi-C30Acm-Q48C) Ethan | 9445.8 | 9445.5 | ESI |
| 1-2 | IFN I-78 (S1Thi-C30Acm-Q48C-S75C) MESNA | 9540.9 | 9541.6 | ESI |
| 1-3 | IFN I-78 (S1Thi-N3C-C30Acm-Q48C) Ethan | 9434.8 | 9434.8 | ESI |
| 1-3 | IFN I-78 (S1Thi-E28C-C30Acm-Q48C-R70C) Ethan | 9366.7 | 9365.8 | ESI |
| 1-3 | IFN I-78 (C30Acm) MESNA | 9521.7 | 9522.0 | ESI |
| 1-3 | IFN I-78 (S1Thi-C30Acm) MESNA | 9549.8 | 9551.1 | ESI |
| 1-3 | IFN I-78 (F7C-C30Acm) MESNA | 9477.7 | 9479.3 | ESI |
| 1-3 | IFN I-78 (N24C-C30Acm) MESNA | 9510.8 | 9510.3 | ESI |
| 1-3 | IFN I-78 (G25C-C30Acm) MESNA | 9567.8 | 9567.3 | ESI |
| 1-3 | IFN I-78 (E28C-C30Acm) MESNA | 9495.7 | 9496.4 | ESI |
| 1-3 | IFN I-78 (C30Acm-K32C) MESNA | 9496.7 | 9496.3 | ESI |
| 1-3 | IFN I-78 (C30Acm-M35C) MESNA | 9493.7 | 9493.3 | ESI |
| 1-3 | IFN I-78 (C30Acm-D38C) MESNA | 9509.8 | 9509.4 | ESI |
| 1-3 | IFN I-78 (C30Acm-E41C) MESNA | 9495.7 | 9495.3 | ESI |
| 1-3 | IFN I-78 (C30Acm-Q48C) MESNA | 9496.7 | 9496.4 | ESI |
| 1-3 | IFN I-78 (C30Acm-R70C) MESNA | 9468.7 | 9468.3 | ESI |
| 1-3 | IFN I-78 (C30Acm-S75C) MESNA | 9537.8 | 9538.4 | ESI |
| 1-3 | IFN I-78 (C30Acm-E41C-S75C) MESNA | 9511.8 | 9511.3 | ESI |
| 1-3 | IFN I-78 (C30Acm-E42C-S75C) MESNA | 9511.8 | 9510.7 | ESI |
| 1-3 | IFN I-78 (C30Acm-Q45C-S75C) MESNA | 9512.8 | 9512.7 | ESI |
| 1-3 | IFN I-78 (C30Acm-L46C-S75C) MESNA | 9527.8 | 9527.7 | ESI |
| 1-3 | IFN I-78 (C30Acm-Q47C-S75C) MESNA | 9512.8 | 9512.7 | ESI |
| 1-3 | IFN I-78 (C30Acm-Q48C-S75C) MESNA | 9512.8 | 9513.9 | ESI |
| 1-3 | IFN I-78 (C30Acm-F49C-S75C) MESNA | 9493.8 | 9493.7 | ESI |
| 1-3 | IFN I-78 (C30Acm-Q50C-S75C) MESNA | 9512.8 | 9513.7 | ESI |
| 1-3 | IFN I-78 (S1Thi-Y29C-C30Acm-Q48C) MESNA | 9464.8 | 9465.6 | ESI |
| 1-3 | IFN I-78 (S1Thi-C30Acm-M35C-Q48C) MESNA | 9496.8 | 9496.6 | ESI |
| 1-3 | IFN I-78 (S1Thi-C30Acm-E41C-Q48C) MESNA | 9498.8 | 9499.6 | ESI |

Example 2

Synthesis of Peptide Fragments

Example 2-1

Synthesis of IFN 79-165(N79C-K107C-R112C-R123C-C140Acm) (SEQ ID NO. 31)

Amino-PEGA resin (from Merck & Co., Inc.) (50 µmol) was added onto a column for solid phase synthesis, 4-hydroxymethyl-3-methoxyphenoxy butyric acid (HMPB) (125 µmol), O-benzotriazol-1-yl-1,1,3,3-tetramethyluronium tetrafluoroborate (TBTU) (125 µmol), and N-ethylmorpholine (125 µmol) were dissolved in (DMF) (1.25 ml), and stirred at room temperature for 4 hours. The resin was sufficiently washed with DMF and DCM. Subsequently, Fmoc-Asn (Trt)-OH (0.25 mmol), 1-mesitylenesulfonyl-3-nitro-1,2,4-triazole (MSNT) (0.25 mmol), N-methylimidazole (0.187 mmol) were dissolved in DCM (1.25 ml) and placed in the column for solid phase synthesis, and then stirred for 4 hours.

After stirring, the resin was washed with DCM and DMF, and the Fmoc group was treated for 15 minutes with 20% piperidine/DMF solution (2 ml) to allow deprotection. After washing with DMF, the subsequent peptide chain elongation employed the method shown below to sequentially condense amino acids.

The amino acid protected with an Fmoc or Boc group was dissolved in DMF, and the solution was added to the solid phase synthesis column (0.25 mmol). 0.2 M 1-[bis(dimethylamino)methylene]-5-chloro-1H-benzotriazolium 3-oxide hexafluorophosphate (HCTU)/DMF (0.25 mmol) was added to the solid phase synthesis column and 0.8 M N-methyl morpholine/DMF (0.50 mmol) or 0.8 M 2,6,4-trimethylpyridine/DMF (0.50 mmol) was added to the column for solid synthesis. After stirring at room temperature for 15 or 30 minutes, the resin was washed with DMF, and the Fmoc group was treated for 10 minutes with 20% piperidine/DMF solution (2 ml) to allow deprotection. This operation was repeated, and amino acids were sequentially condensed by Fmoc solid phase synthesis method.

To the resin obtained was added trifluoroacetic acid:water:phenol:thioanisole:triisopropylsilane (=95:2.5:2.5:2.5:5), and this was stirred at room temperature. After 3 hours, this solution was again added to a separately prepared diethyl ether and allowed to precipitate, then subjected to centrifugal separation, and the solution portion was removed to obtain a residue comprising the target peptide. This residue obtained was purified with reverse phase HPLC [column: SHISEIDO Proteonavi], and as a result of mass analysis by ESI-MS, the mass of the compound obtained corresponded with the mass of IFN 79-165(N79C-K107C-R112C-R123C-C140Acm) (calculated value=10499.1 Da, actual value=10498.1 Da.

Example 2-2

Synthesis of Other Peptide Fragments

The following peptide fragments were synthesized similarly to (Example 2-1).
IFN 79-165(N79C-C140Acm) (SEQ ID NO. 32)
IFN 79-165(N79C-K107C-C140Acm) (SEQ ID NO. 33)
IFN 79-165(N79C-K107C-R112C-C140Acm) (SEQ ID NO. 34)
IFN 79-165(N79C-K107C-E136C-C140Acm) (SEQ ID NO. 35)
IFN 79-165(N79C-T99C-K107C-R112C-C140Acm) (SEQ ID NO. 36)
IFN 79-165(N79C-E103C-K107C-E136C-C140Acm) (SEQ ID NO. 37)
IFN 79-165(N79C-E106C-K107C-E136C-C140Acm) (SEQ ID NO. 38)
IFN 79-165(N79C-K107C-D109C-E136C-C140Acm) (SEQ ID NO. 39)
IFN 79-165(N79C-K107C-L115C-E136C-C140Acm) (SEQ ID NO. 40)
IFN 79-165(N79C-K107C-L119C-E136C-C140Acm) (SEQ ID NO. 41)
IFN 79-165(N79C-K107C-R112C-H130C-C140Acm) (SEQ ID NO. 42)
IFN 79-165(N79C-K107C-R112C-E136C-C140Acm) (SEQ ID NO. 43)
IFN 79-165(N79C-K107C-R112C-H139C-C140Acm) (SEQ ID NO. 44)
IFN 79-165(N79C-K107C-R112C-C140Acm-R164C) (SEQ ID NO. 45)

Mass spectrometry results of compounds obtained in (Example 2-1) and (Example 2-2) are shown in (Table 2) below.

TABLE 2

| Example | Compound | Theoretical value (MW) | Actual value (MW) | Ionization method |
|---|---|---|---|---|
| 2-1 | IFN 79-165 (N79C-K107C-R112C-R123C-C140Acm) | 10499.1 | 10498.1 | ESI |
| 2-2 | IFN 79-165 (N79C-C140Acm) | 10630.3 | 10630.1 | ESI |
| 2-2 | IFN 79-165 (N79C-K107C-C140Acm) | 10605.2 | 10605.6 | ESI |
| 2-2 | IFN 79-165 (N79C-K107C-R112C-C140Acm) | 10552.2 | 10552.4 | ESI |
| 2-2 | IFN 79-165 (N79C-K107C-E136C-C140Acm) | 10579.3 | 10578.5 | ESI |
| 2-2 | IFN 79-165 (N79C-T99C-K107C-R112C-C140Acm) | 10554.2 | 10554.3 | ESI |
| 2-2 | IFN 79-165 (N79C-E103C-K107C-E136C-C140Acm) | 10553.3 | 10554.0 | ESI |
| 2-2 | IFN 79-165 (N79C-E106C-K107C-E136C-C140Acm) | 10553.3 | 10553.0 | ESI |
| 2-2 | IFN 79-165 (N79C-K107C-D109C-E136C-C140Acm) | 10567.3 | 10568.0 | ESI |
| 2-2 | IFN 79-165 (N79C-K107C-L115C-E136C-C140Acm) | 10569.2 | 10568.9 | ESI |
| 2-2 | IFN 79-165 (N79C-K107C-L119C-E136C-C140Acm) | 10569.2 | 10568.8 | ESI |
| 2-2 | IFN 79-165 (N79C-K107C-R112C-H130C-C140Acm) | 10518.2 | 10517.3 | ESI |
| 2-2 | IFN 79-165 (N79C-K107C-R112C-E136C-C140Acm) | 10526.2 | 10525.4 | ESI |
| 2-2 | IFN 79-165 (N79C-K107C-R112C-H139C-C140Acm) | 10518.2 | 10517.3 | ESI |
| 2-2 | IFN 79-165 (N79C-K107C-R112C-C140Acm-R164C) | 10499.1 | 10498.3 | ESI |

Example 3

Synthesis of Disialo Glycosylated IFN-β

Example 3-1

Synthesis of 2-6 DiSialo(S1C-Q48C-N79C-K107C-R112C-R123C) (SEQ ID NO. 46)

IFN 1-78(S1Thi-C30Acm-Q48C)Ethan (SEQ ID NO. 3) and IFN 79-165(N79C-K107C-R112C-R123C-C140Acm) (SEQ ID NO. 31) were dissolved in a buffer solution at pH 7.2 comprising 4-mercaptophenylacetic acid (8 M guanidine hydrochloric acid solution, 0.1 M phosphoric acid solution, and 125 mM 4-mercaptophenylacetic acid), and left at room temperature. After 24 hours, dithiothreitol solution (2 M dithiothreitol) was added to the reaction solution, and left at room temperature for 3 hours. Upon completion of the fraction, methoxyamine solution (1 M methoxyamine hydrochloride) and hydrochloric acid solution (1 M hydrochloric acid and 8 M guanidine were added to the solution, the pH was adjusted to 4.0, and then left at room temperature for 24 hours. The solution after the reaction had completed was demineralized by reverse phase HPLC [column: SHISEIDO Proteonavi] and lyophilized.

The crude purified product obtained was dissolved in a buffer solution at pH 8.5 (8 M guanidine hydrochloric acid solution and 0.1 M trishydroxymethylaminomethane), the bromoacetylated disialo sugar chain represented by the following Formula (7) (5 equivalents) was added, and left for 1 hour.

added, and left for 1 hour under cooling conditions (4° C.). The solution after reaction was subjected to overnight substitution to acetic acid solution (10 mM acetic acid solution) under cooling conditions (4° C.) to remove the denaturing agent. The solution after folding was purified by HPLC [column: SHISEIDO Proteonavi] and a result of mass spectrometry (ESI ionization method), the mass of the compound obtained corresponded with the mass of the target 2-6 diSialo(S1C-Q48C-N79C-K107C-R112C-R123C) (calculated value=33304.8 Da, actual value=33303.6 Da).

[Chemical Formula 21]

Formula (7)

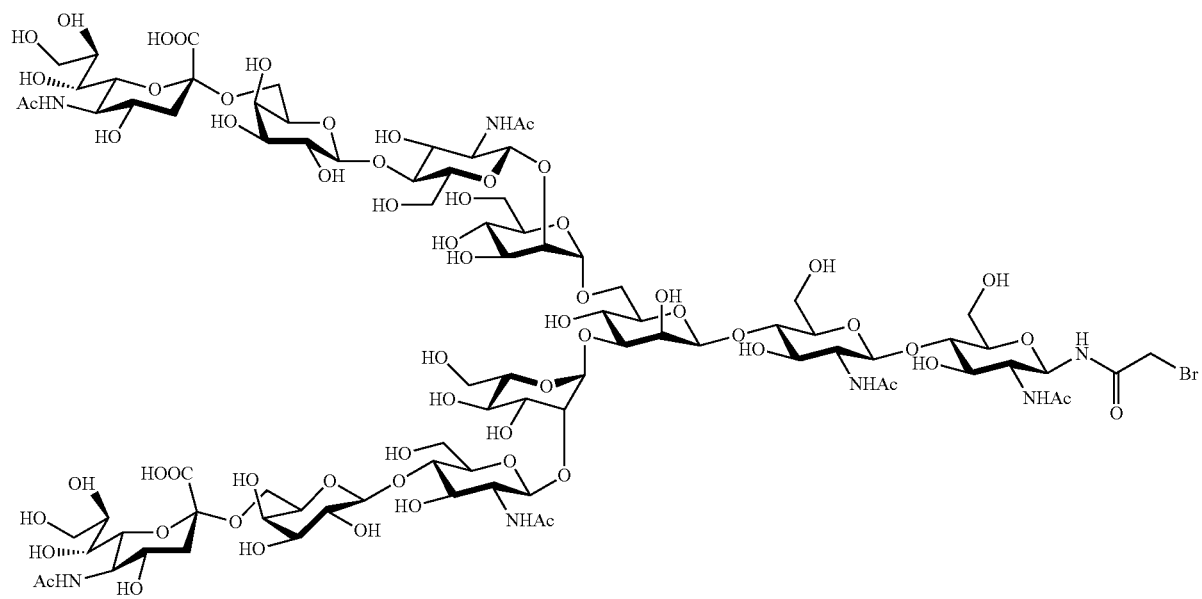

Upon completion of the reaction, sodium mercaptoethanesulfonate solution (200 mM sodium mercaptoethanesulfonate) was added, and left at room temperature for 30 minutes. The solution after the reaction had completed was demineralized by reverse phase HPLC [column: SHISEIDO Proteonavi] and lyophilized.

The crude purified product obtained by the above step was dissolved in silver acetate solution (60 mM silver acetate, 7.5 M urea, and 875 mM acetic acid), and left at room temperature for 4 hours. After the reaction, dithiothreitol solution (2 M dithiothreitol) was added. To the reactant was added a buffer solution at 8.5 (8 M guanidine hydrochloride and 0.1 M trishydroxymethylaminomethane), and demineralized by HPLC [column: SHISEIDO Proteonavi] and lyophilized.

The lyophilizate obtained was dissolved in a buffer solution at pH 8.5 (8 M guanidine hydrochloric acid solution and 0.1 M trishydroxymethylaminomethane), and left at room temperature for 30 minutes. The solution was substituted under cooling conditions (4° C.) to diluted guanidine hydrochloride solution (4.5 M guanidine hydrochloride and 0.1 M trishydroxymethylaminomethane). To the substituted solution was added copper sulfate solution (300 mM copper (II) sulfate pentahydrate), and left for 4 hours under cooling conditions (4° C.). After the reaction, ethylenediaminetetraacetic acid (400 mM ethylenediaminetetraacetic acid) was Example 3-2

Synthesis of 2-6 DiSialo(Q48C-S75C-N79C-K107C-R112C-E136C) (SEQ ID NO. 47)

IFN 1-78(C30Acm-Q48C-S75C)MESNA (SEQ ID NO. 25) and IFN 79-165(N79C-K107C-R112C-E136C-C140Acm) (SEQ ID NO. 43 were dissolved in a buffer solution at pH 7.2 comprising 4-mercaptophenylacetic acid (8 M guanidine hydrochloric acid solution, 0.1 M phosphoric acid solution, and 125 mM 4-mercaptophenylacetic acid), and left at room temperature. After 24 hours, dithiothreitol solution (2 M dithiothreitol) was added to the reaction solution, and left at room temperature for 3 hours. The solution after the reaction had completed was demineralized by reverse phase HPLC [column: SHISEIDO Proteonavi] and lyophilized.

Mass spectrometry (ESI ionization method) was performed with the crude purified product obtained similarly to (Example 3-1). As a result, the mass of the compound obtained corresponded with the mass of the target 2-6 diSialo(Q48C-S75C-N79C-K107C-R112C- E136C) (calculated value=33331.8 Da, actual value=33331.2 Da).

Example 3-3

Synthesis of 2-3DiSialo(S1C-N3C-Q48C-N79C-K107C-R112C) (SEQ ID NO. 48)

With IFN 1-78(S1Thi-N3C-C30Acm-Q48C)Ethan (SEQ ID NO. 5) and IFN 79-165(N79C-K107C-R112C-C140Acm) (SEQ ID NO. 34), disialo glycosylated IFN-β was synthesized similarly to (Example 3-1) except that the bromoacetylated disialo sugar chain represented by the following Formula (8) was alternatively used. As a result of performing mass spectrometry (ESI ionization method), the mass of the compound obtained corresponded with the mass of the target 2-3disialo(S1C-N3C-Q48C-N79C-K107C-R112C) (calculated value=33346.9 Da, actual value=33346.6 Da).

[Chemical Formula 22]

Formula(8)

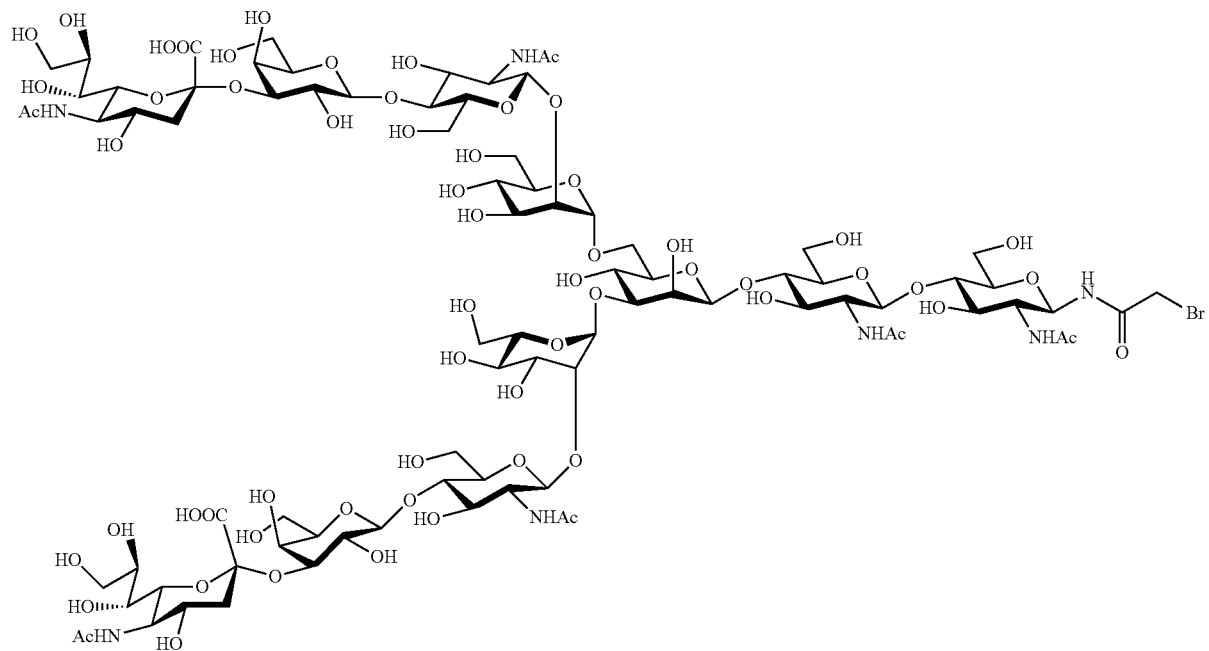

Example 3-4

Synthesis of Other Disialo Glycosylated IFN-β

The synthesis of the compounds shown below was performed with a method similar to (Example 3-1).

2-6 diSialo(S1C-N3C-Q48C-N79C-K107C-R112C) (SEQ ID NO. 49)
2-6 diSialo(S1C-Q48C-N79C-T99C-K107C-R112C) (SEQ ID NO. 50)
2-6 diSialo(S1C-Q48C-N79C-K107C-R112C-H130C) (SEQ ID NO. 51)
2-6 diSialo(S1C-Q48C-N79C-K107C-R112C-E136C) (SEQ ID NO. 52)
2-6 diSialo(S1C-Q48C-N79C-K107C-R112C-H139C) (SEQ ID NO. 53)
2-6 diSialo(S1C-Q48C-N79C-K107C-R112C-R164C) (SEQ ID NO. 54)
2-6 diSialo(S1C-Y29C-Q48C-N79C-K107C-E136C) (SEQ ID NO. 55)
2-6 diSialo(S1C-M35C-Q48C-N79C-K107C-E136C) (SEQ ID NO. 56)
2-6 diSialo(S1C-E41C-Q48C-N79C-K107C-E136C) (SEQ ID NO. 57)
2-6 diSialo(S1C-Q48C-S75C-N79C-K107C-E136C) (SEQ ID NO. 58)
2-6 diSialo(S1C-E28C-Q48C-R70C-N79C) (SEQ ID NO. 59)
2-6 diSialo(S1C-Q48C-N79C-K107C-R112C) (SEQ ID NO. 60)
2-6 diSialo(S1C-Q48C-N79C-K107C) (SEQ ID NO. 61)
2-6 diSialo(S1C-N3C-Q48C-N79C) (SEQ ID NO. 62)
2-6 diSialo(S1C-N79C-K107C-E136C) (SEQ ID NO. 63)

The synthesis of the compounds shown below was performed with a method similar to (Example 3-2).

2-6 diSialo(E41C-S75C-N79C-E103C-K107C-E136C) (SEQ ID NO. 64)
2-6 diSialo(E41C-S75C-N79C-E106C-K107C-E136C) (SEQ ID NO. 65)
2-6 diSialo(E41C-S75C-N79C-K107C-D109C-E136C) (SEQ ID NO. 66)
2-6 diSialo(E41C-S75C-N79C-K107C-R112C-E136C) (SEQ ID NO. 67)
2-6 diSialo(E41C-S75C-N79C-K107C-L115C-E136C) (SEQ ID NO. 68)
2-6 diSialo(E41C-S75C-N79C-K107C-L119C-E136C) (SEQ ID NO. 69)
2-6 diSialo(N24C-N79C-K107C-R112C-E136C) (SEQ ID NO. 70)
2-6 diSialo(G25C-N79C-K107C-R112C-E136C) (SEQ ID NO. 71)
2-6 diSialo(K32C-N79C-K107C-R112C-E136C) (SEQ ID NO. 72)

2-6 diSialo(M35C-N79C-K107C-R112C-E136C) (SEQ ID NO. 73)
2-6 diSialo(D38C-N79C-K107C-R112C-E136C) (SEQ ID NO. 74)
2-6 diSialo(E41C-N79C-K107C-R112C-E136C) (SEQ ID NO. 75)
2-6 diSialo(F7C-N79C-K107C-R112C-E136C) (SEQ ID NO. 76)
2-6 diSialo(Q48C-N79C-K107C-R112C-E136C) (SEQ ID NO. 77)
2-6 diSialo(S75C-N79C-K107C-R112C-E136C) (SEQ ID NO. 78)
2-6 diSialo(E41C-S75C-N79C-K107C-E136C) (SEQ ID NO. 79)
2-6 diSialo(E42C-S75C-N79C-K107C-E136C) (SEQ ID NO. 80)
2-6 diSialo(Q45C-S75C-N79C-K107C-E136C) (SEQ ID NO. 81)
2-6 diSialo(L46C-S75C-N79C-K107C-E136C) (SEQ ID NO. 82)
2-6 diSialo(Q47C-S75C-N79C-K107C-E136C) (SEQ ID NO. 83)
2-6 diSialo(Q48C-S75C-N79C-K107C-E136C) (SEQ ID NO. 84)
2-6 diSialo(F49C-S75C-N79C-K107C-E136C) (SEQ ID NO. 85)
2-6 diSialo(Q50C-S75C-N79C-K107C-E136C) (SEQ ID NO. 86)
2-6 diSialo(N79C-K107C-R112C-E136C) (SEQ ID NO. 87)
2-6 diSialo(E28C-N79C-K107C-E136C) (SEQ ID NO. 88)
2-6 diSialo(M35C-N79C-K107C-E136C) (SEQ ID NO. 89)
2-6 diSialo(R70C-N79C-K107C-E136C) (SEQ ID NO. 90)
2-6 diSialo(S75C-N79C-K107C-E136C) (SEQ ID NO. 91)

The synthesis of the compound shown below was performed with a method similar to (Example 3-3).
2-6 diSialo(E41C-S75C-N79C-K107C-E136C) (SEQ ID NO. 79)

Example 3-5

Synthesis of 2-6 diSialo(S1C-R26C-Q48C-A67C-N79-A88C) (SEQ ID NO. 100)

Example 3-5-A

Synthesis of IFN 1-25(S1Thi)thiophenyl (SEQ ID NO. 101)

Amino-PEGA resin (from Merck & Co., Inc.) (50 μmol) was added onto a column for solid phase synthesis, 4-hydroxymethyl-3-methoxyphenoxy butyric acid (HMPB) (125 μmol), O-benzotriazol-1-yl-1,1,3,3-tetramethyluronium tetrafluoroborate (TBTU) (125 μmol), and N-ethylmorpholine (125 μmol) were dissolved in dimethylformamide (DMF) (125 ml), and stirred at room temperature for 4 hours. The resin was sufficiently washed with DMF are dichloromethane (DCM). Subsequently, Fmoc-Trp(Boc)-OH (0.25 mmol), 1-mesitylenesulfonyl-3-nitro-1,2,4-triazole (MSNT) (0.25 mmol), and N-methylimidazole (0.187 mmol) were dissolved in DCM (1.25 ml) and added to the column for solid phase synthesis, and then stirred for 4 hours.

The resin was washed with DCM and DMF, and the Fmoc group as treated for 15 minutes with 20% piperidine/DMF solution (2 ml) to allow deprotection. This was washed with DMF, and the subsequent peptide chain elongation employed the method shown below to sequentially condense amino acids.

The amino acid protected with an Fmoc or Boc group was dissolved in DMF, and the solution was added to the solid phase synthesis column (0.25 mmol). 0.2 M 1-[bis(dimethylamino)methylene]-5-chloro-1H-benzotriazolium 3-oxide hexafluorophosphate (HCTU)/DMF (0.25 mmol) was added to the solid phase synthesis column, and 0.8 M N-methyl morpholine/DMF (0.50 mmol) or 0.8 M 2,6,4-trimethylpyridine/DMF (0.50 mmol) was added to the column for solid phase synthesis. After stirring at room temperature for 15 or 30 minutes, the resin was washed with DMF, and the Fmoc group was treated for 10 minutes with 20% piperidine/DMF solution (2 ml) to deprotection. This operation was repeated, and amino acids were sequentially condensed by Fmoc solid phase synthesis method.

After washing the resin obtained with DCM and DMF, a mixed solution of trifluoroethanol and acetic acid (1:1) was added, and the protected peptide was concentrated from the resin by stirring for 18 hours at room temperature. The reaction solution comprising the protected peptide was concentrated under reduced pressure, and then dried under reduced pressure. The dried protected peptide was dissolved in DMF (2.1 mL), and then cooled under nitrogen atmosphere to −15° C. to −20° C. To this was added thiophenol as the thiol source (0.2 mmol), and then benzotriazol-1-yloxy-trispyrrolidinophosphonium hexafluorophosphate (PyBOP) (1.4 mmol), then diisopropylethylamine (DIPEA) (0.2 mmol) were added. After stirring at −15° C. to −20° C. for 2 hours, trifluoroacetic acid (0.2 mL) was added, and this was allowed to gradually return to room temperature. When the temperature was back to room temperature, the reaction solution was concentrated under reduced pressure. To the residue obtained was added trifluoroacetic acid:water:triisopropylsilane (=92.5:2.5:5), and this was stirred at room temperature. After 2 hours, this solution was again added to a separately prepared diethyl ether and allowed to precipitate, then subjected to centrifugal separation, and the solution portion was removed to obtain a residue comprising the target peptide thioester form. This residue obtained was purified with HPLC [column: SHISEIDO Proteonavi], and as a result of mass analysis by ESI-MS, the mass of the compound obtained corresponded with the mass of the target IFN 1-25(S1Thi)thiophenyl (SEQ ID NO. 101) (calculated value=3062.6 Da, actual value=3062.5 Da).

Example 3-5-B

Synthesis of IFN 26-47(R26C-C30Acm)Ethanthiol (SEQ ID NO. 102)

A peptide fragment was synthesized similarly to the operations of (Example 3-5-A). Ethanthiol was used as the thiol source for IFN 26-47(R26C-C30Acm)Ethanthiol.

As a result of mass analysis by ESI-MS, the synthesis compound corresponded with the mass of the target IFN 26-47(R26C-C30Acm)Ethanthiol (SEQ ID NO. 102) (calculated value=2844.4 Da, actual value=2844.5 Da).

Example 3-5-C

Synthesis of IFN 48-66(Q48Thi)MESNA (SEQ ID NO. 103)

Amino-PEGA resin (from Merck & Co., Inc.) (50 μmol) was added onto a column for solid phase synthesis, 3-Fmoc-4-diaminobenzoic acid (150 μmol), 1-[bis(dimethylamino)methylene]-5-chloro-1H-benzotriazolium 3-oxide hexafluorophosphate (HCTU) (150 μmol), and diisopropylethylamine (300 μmol) were dissolved in DMF (1.25 ml), and stirred at room temperature for 1 hour.

After stirring, the resin was washed with DMF, the Fmoc group was heated for 15 minutes with 20% piperidine/DMF solution (2 ml) to allow deprotection, and then the resin was sufficiently washed, with DMF. Amino acids were sequentially condensed in the subsequent peptide chain elongation employing the method shown below.

The amino acid protected with an Fmoc or Boc group was dissolved in DMF, and the solution was added to the solid phase synthesis column (0.25 mmol). 0.2 M 1-[bis(dimethylamino)methylene]-5-chloro-1H-benzotriazolium 3-oxide hexafluorophosphate (HCTU)/DMF (0.25 mmol) was added to the solid phase synthesis column, and 0.8 M N-methyl morpholine/DMF (0.50 mmol) or 0.8 M 2,6,4-trimethylpyridine/DMF (0.50 mmol) was added to the column for solid phase synthesis. After stirring at room temperature for 15 or 30 minutes, the resin was washed with DMF, and the Fmoc group was treated for 10 minutes with 20% piperidine/DMF solution (2 ml) to allow deprotection. This operation was repeated, and amino acids were sequentially condensed by Fmoc solid phase synthesis method.

After washing the resin obtained with DMF and DCM, 4-Nitrophenyl Chloroformate (1.4 mmol) was dissolved in DCM, added to the solid phase synthesis column, and then stirred at room temperature for 40 minutes. After stirring the resin was washed with DCM and DMF, diisopropylethylamine (5.0 mmol) dissolved in DMF solution was added, and stirred at room temperature for 15 minutes. After washing the resin obtained with DMF and DCM, trifluoroacetic acid:water:triisopropylsilane (=92.5:2.5:5) was added, and this was stirred at room temperature. After 2 hours, the resin was sufficiently washed with DMF and DCM, and then the resin was sufficiently washed with a buffer solution at pH 8.5 comprising sodium 2-mercaptoethanesulfonate (6 M guanidine hydrochloric acid solution, 0.2 M phosphoric acid solution, and 1 M sodium 2-mercaptoethanesulfonate). The above buffer was added to the resin, and stirred at room temperature for 2 hours. After stirring, the solution obtained was purified with HPLC [column: SHISEIDO Proteonavi], and as a result of mass analysis by ESI-MS, the mass of the compound obtained corresponded with the mass of the target IFN 48-66(Q48Thi)MESNA (SEQ ID NO. 103) (calculated value=2413.8 Da, actual value=2413.9 Da).

Example 3-5-D

Synthesis of Disialo Glycosylated IFN 67-87(A67Thi,N79)thiophenyl (SEQ ID NO. 104)

Amino-PEGA resin (from Merck & Co., Inc.) (50 μmol) was added onto a column for solid phase synthesis, 3-Fmoc-4-diaminobenzoic acid (150 μmol), 1-[bis(dimethylamino)methylene]-5-chloro-1H-benzotriazolium 3-oxide hexafluorophosphate (HCTU) (150 μmol) , and diisopropylethylamine (300 μmol) were dissolved in DMF (1.25 ml), and stirred at room temperature for 1 hour.

After stirring the resin was washed with DMF, the Fmoc group was treated for 15 minutes with 20% piperidine/DMF solution (2 ml) to allow deprotection, and then the resin was sufficiently washed with DMF. Amino acids were sequentially condensed in the subsequent peptide chain elongation employing the method shown below.

The amino acid protected with an Fmoc or Boc group was dissolved in DMF, and the solution was added to the solid phase synthesis column (0.25 mmol). 0.2 M 1-[bis(dimethylamino)methylene]-5-chloro-1H-benzotriazolium 3-oxide hexafluorophosphate (HCTU)/DMF (0.25 mmol) was added to the solid phase synthesis column, and 0.8 M N-methyl morpholine/DMF (0.50 mmol) or 0.8 M 2,6,4-trimethylpyridine (0.50 mmol) was added to the column for solid phase synthesis. After stirring at room temperature for 15 or 30 minutes, resin was washed with DMF, and the Fmoc group was treated for 10 minutes with 20% piperidine/DMF solution (2 ml) to allow protection. This operation was repeated, and amino acids were sequentially by Fmoc solid phase synthesis method.

In the 8-residue peptide obtained, the Fmoc group was deprotected by treating with 20% piperidine/DMF solution (2 ml) for 15 minutes. After washing with DMF, dibenzyl disialo sugar chain asparagine (0.2 mmol) and DEPBT (0.2 mmol) were dissolved in DMF/DMSO (1:1 mixed solution, 2.2 ml) in a separately prepared centrifuge tube, placed in the column for solid phase synthesis, DIPEA (0.15 mmoL) was added, and stirred at room temperature for 18 hours. Upon washing with DMF and DCM, a 9-residue sugar chain peptide bound to a dibenzyl disialo sugar chain asparagine represented by the following Formula (18) was obtained on the solid phase.

[Chemical Formula 23]

Formula(18)

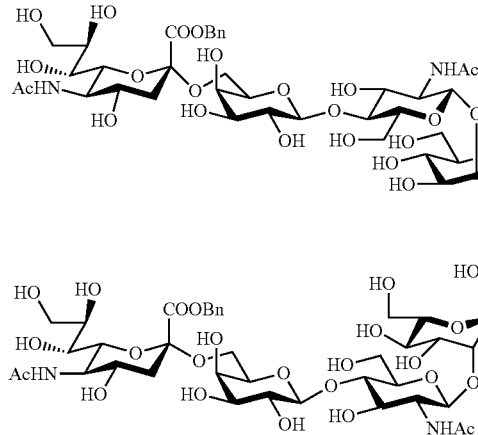
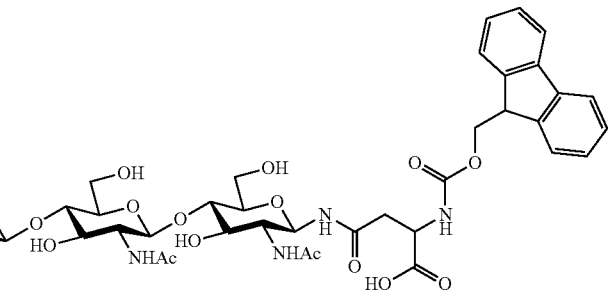

In the subsequent glycopeptide chain elongation, amino acids were sequentially condensed with the method shown below.

An amino acid having the amino acid protected with an Fmoc group, HOBt (0.50 mmol), and DIPCI (0.475 mmol) were dissolved in DMF (6.3 ml), activated for 15 minutes, and then placed in the column for solid phase synthesis. After room temperature stirring for 1 hour, the Fmoc group was treated for 20 minutes with 20% piperidine/DMF solution (2 ml) to allow protection. This operation was repeated, and amino acids were sequentially condensed.

After washing the resin obtained with DCM and DMF, a mixed solution of trifluoroethanol and acetic acid (1:1) was added so that the resin was sufficiently soaked, and the resin and the glycosylated peptide fragment was cleaved by stirring for 18 hours at room temperature. The cleaved resin was filtered off, and the reaction solution was concentrated under reduced pressure. The residue obtained was concentrated to obtain a sugar chain peptide having the amino acid side chain protected.

The glycosylated peptide fragment obtained (50 mmol) was transferred to a recovery flask, dissolved in DMF, and that cooled under nitrogen atmosphere to −15° C. to −20° C. To this was added thiophenol (0.15 mmol), and then PyBOP (2.5 mmol), then DIPEA (0.15 mmol) were added. After stirring at −15° C. to −20° C. for 2 hours, trifluoroacetic acid was added, and this was allowed to gradually return to room temperature. When the temperature was back to room temperature, the reaction solution was concentrated under reduced pressure. To the residue obtained was added trifluoroacetic acid:water:TIPS (=95:2.5:2.5), and this was stirred at room temperature. After 2 hours, this solution was again added to a separately prepared diethyl ether and allowed to precipitate, then subjected to centrifugal separation, and the solution portion was removed to obtain a residue comprising the target peptide thioester form. This residue obtained was purified with HPLC [column: SHISEIDO proteonavi], and as a result of mass analysis by ESI-MS, the mass of the compound obtained corresponded with the mass of the target disialo glycosylated IFN 67-87 (A67Thi,N79)thiophenyl (SEQ ID NO. 104) (calculated value=4903.1 Da, actual value=4903.1 Da).

Example 3-5-E

Synthesis of IFN 88-165(C140Acm) (SEQ ID NO. 105)

Amino-PEGA resin (from Merck & Co., Inc.) (50 µmol) was added onto a column for solid phase synthesis, 4-hydroxymethyl-3-methoxyphenoxy butyric acid (HMPB) (125 µmol), O-benzotriazol-1-yl-1,1,3,3-tetramethyluronium tetrafluoroborate (TBTU) (125 µmol) and N-ethylmorpholine (125 µmol) were dissolved in DMF (1.25 ml), and stirred at room temperature for 4 hours. The resin was sufficiently washed with DMF and DCM. Subsequently, Fmoc-Asn (Trt)-OH (0.25 mmol), 1-mesitylenesulfonyl-3-nitro-1,2,4-triazole (MSNT) (0.25 mmol), and N-methylimidazole (0.187 mmol) were dissolved in DCM (1.25 ml) and placed in the column for solid phase synthesis, and then stirred for 4 hours.

After stirring, the resin was washed with DCM and DMF, and the Fmoc group was treated for 15 minutes with 20% piperidine/DMF solution (2 ml) to allow deprotection. After washing with DMF, the subsequent peptide chain elongation employed the method shown below to sequentially condense amino acids.

The amino acid protected with an Fmoc or Boc group was dissolved in DMF, and the solution was added to the solid phase synthesis column (0.25 mmol). 0.2 M 1-[bis(dimethylamino)methylene]-5-chloro-1H-benzotriazolium 3-oxide hexafluorophosphate (HCTU)DMF (0.25 mmol) was added to the solid phase synthesis column, and 0.8 M N-methyl morpholine/DMF (0.50 mmol) or 0.8 M 2,6,4-trimethylpyridine/DMF (0.50 mmol) was added to the column for solid phase synthesis. After stirring at room temperature for 15 or 30 minutes, the resin was washed with DMF, and the Fmoc group was treated for 10 minutes with 20% piperidine/DMF solution (2 ml) to allow deprotection. This operation was repeated, and amino acids were sequentially condensed by Fmoc solid phase synthesis method.

To the resin obtained was added trifluoroacetic acid:water:phenol:thioanisole:triisopropylsilane (=95:2.5:2.5:2.5:5), and this was stirred at room temperature. After 3 hours, this solution was again added to a separately prepared diethyl ether and allowed to precipitate, then subjected to centrifugal separation, and the solution portion was removed to obtain a residue comprising the target oxide. This residue obtained was purified with reverse phase HPLC [column: SHISEIDO Proteonavi] and as a result of mass analysis by ESI-MS, the mass of the compound obtained corresponded with the mass of IFN 88-165(C140Acm) (SEQ ID NO. 105) (calculated value=9647.3 Da, actual value=9647.2 Da).

Example 3-5-F

Binding of Each Fragment (Step 1. Kinetic Ligation Step)
IFN 1-25(S1Thi)thiophenyl (SEQ ID NO. 101) and IFN 26-47(R26C-C30Acm)Ethanthiol (SEQ ID NO. 102) were dissolved in a buffer solution at pH 6.8 (8 M guanidine hydrochloric acid solution, 0.2 M phosphoric acid solution, and 20 mM TCEP), and allowed to react at room temperature for 3 hours. The solution after the reaction had completed was purified by reverse phase HPLC [column: SHISEIDO Proteonavi] and lyophilized. As a result of mass analysis of this lyophilized product obtained by ESI-MS, the mass of the compound obtained corresponded with the mass of IFN 1-47(S1Thi-R26C-C30Acm)Ethanthiol (SEQ ID NO. 106) (calculated value=5796.8 Da, actual value=5796.7 Da).

(Step 2. Native Chemical Ligation Step A)
Disialo glycosylated IFN 67-87(A67Thi,N79)thiophenyl (SEQ ID NO. 104) and IFN 88-165(C140Acm) (SEQ ID NO. 105) were dissolved in a buffer solution at pH 7.2 (8 M guanidine hydrochloric acid solution, 0.2 M phoshoric acid solution and 20 mM TCEP), thiophenol (3% V/V) was added, and allowed to react at room temperature. After 23 hours, methoxyamine solution (6 M guanidine hydrochloride, 0.2 M methoxyamine hydrochloride, and 20 mM TCEP) was added to the reaction solution, the pH was adjusted to 4.0, and then allowed to react at room temperature for 4 hours. To the reaction solution was added 50 mM NaOH aqueous solution to make the reaction solution basic, and then allowed to react on ice for 0.5 hours. Upon completion of the reaction, the solution after the reaction had completed was purified by reverse phase HPLC [column: SHISEIDO Proteonavi] to obtain a lyophilized product. As a result of mass analysis of this lyophilized product obtained by ESI-MS, the mass of the compound obtained corresponded with the mass of disialo glycosylated IFN 67-165 (A67C-N79-A88C-C140Acm) (SEQ ID NO. 107) (calculated value=14247.9 Da, actual value=14247.2 Da).

(Step 3. Native Chemical Ligation Step B)
Disialo glycosylated IFN 67-165(A67C-N79-A88C-C140Acm) (SEQ ID NO. 107) obtained in step 2 and IFN 48-66(Q48Thi)MESNA (SEQ ID NO. 103) were dissolved in a buffer solution at pH 7.2 (8 M guanidine hydrochloric acid solution, 0.2 M phosphoric acid solution, 20 mM TCEP, and 30 mM MPAA), and allowed to react at room temperature. After 18 hours, methoxyamine solution (6 M guanidine hydrochloride, 0.2 M methoxyamine hydrochloride, and 20 mM TCEP) was added to the reaction solution, the pH was adjusted to 4.0, and then allowed to react at room temperature. After 5 hours, to the reaction solution was added sodium 2-mercaptoethanesulfonate, and allowed to react at room temperature for 1 hour. Upon completion of the reaction, the solution after the reaction had completed was purified by reverse phase HPLC [column: SHISEIDO Proteonavi] to obtain a lyophilized product. As a result of mass analysis of this lyophilized product obtained by ESI-MS, the mass of the compound obtained corresponded with the mass of disialo glycosylated IFN 48-165(Q48C-A67C-N79-A88C-C140Acm) (SEQ ID NO. 108) (calculated value=16507.6 Da, actual value=16507.9 Da).

(Step 4. Native Chemical Ligation Step C)

Similarly to step 3, IFN 1-47(S1Thi-R26C-C30Acm) Ethanthiol (SEQ ID NO. 106) obtained in step 1 and disialo glycosylated IFN 48-165(Q48C,A67C,N79,A88C, C140Acm) (SEQ ID NO. 108) were allowed to react. As a result of mass analysis by ESI-MS, the compound obtained from the reaction corresponded with the mass of the target disialo glycosylated IFN 1-165(S1C-R26C-C30Acm-Q48C-A67C-N79-A88C-C140Acm) (SEQ ID NO. 109) (calculated value=22230.2 Da, actual value=22230.3 Da).

(Step 5. Glycosylation Step)

Disialo glycosylated IFN 1-165(S1C-R26C-C30Acm-Q48C-A67C-N79-A88C-C140Acm) (SEQ ID NO. 109) obtained in step 4 was dissolved in a buffer solution at pH 8.5 (8 M guanidine hydrochloric acid solution, 0.1 M tris solution), the bromoacetylated disialo sugar chain represented by the following Formula (19) (25 equivalents) was added, and allowed to react at room temperature 2 hours.

[Chemical Formula 24]

the side chain of asparagine (SEQ ID NO. 110) (calculated value=33545.4 Da, actual value=33545.5 Da).

(Step 6. Deprotection of Acm Group)

The lyophilizate obtained by the above step 5 was dissolved in silver acetate solution (100 mM silver acetate and 90% acetic acid aqueous solution), and allowed to react at room temperature. After 4 hours, the production of the target product was confirmed with HPLC and ESI-MS. To the reaction solution was added dithiothreitol, stirred at room temperature for 15 minutes, and then subjected to centrifugal separation, and the supernatant excluding the precipitate was collected. This supernatant collected was filtered with a membrane filter; the filtrate portion comprising the target product was purified by reverse phase HPLC [column: SHISEIDO Proteonavi] to obtain a lyophilized product. As a result of mass analysis of this lyophilized product obtained by ESI-MS, the mass of the compound obtained corresponded with the mass of 2-6 diSialo(S1C-R26C-Q48C-A67C-N79-A88C) having disialo sugar chains added at positions 1, 26, 48, 67, and 88 via side chain sulfur atoms of cysteine and having a sugar chain added at position 79 via the side chain of asparagine (SEQ ID NO. 111) (calculated value=33403.3 Da, actual value=33403.2 Da).

(Step 7. Folding Step)

The lyophilizate obtained by the above step 6 was dissolved in a buffer solution at pH 8.5 (8 M guanidine hydrochloric acid solution and 0.1 M trishydroxymethylaminomethane), and left at room temperature for 30 minutes. The solution was substituted under cooling conditions (4° C.) to diluted guanidine hydrochloride solution (4.5 M guanidine hydrochloride and 0.1 M trishydroxymethylaminomethane). To the substituted solution was added copper sulfate solution (300 mM copper (II) sulfate pentahydrate), and left for 3 hours under cooling conditions (4° C.). After Formula(19)

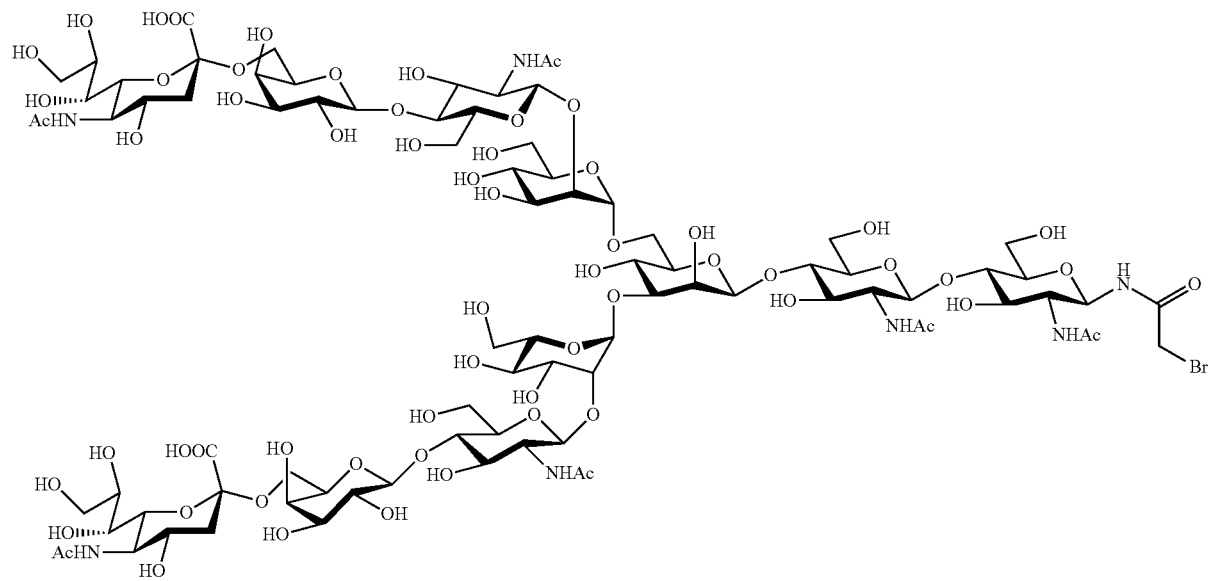

Upon completion of the reaction, the reaction solution was purified by reverse phase HPLC [column: SHISEIDO Proteonavi] to obtain a lyophilized podia As a result of mass analysis of this lyophilized product obtained by ESI-MS, the mass of the compound obtained corresponded with the mass of 2-6 diSialo(S1C-R26C-C30Acm-Q48C-A67C-N79-A88C-C140Acm) having disialo sugar chains added at positions 1, 26, 48, 67, and 88 via side chain sulfur atoms of cysteine and having a sugar chain added at position 79 via the reaction, ethylenediaminetetraacetic acid (400 mM ethylenediaminetetraacetic acid) was added, and left under cooling conditions (4° C.) for 0.5 hours. The solution after reaction was subjected to overnight substitution to acetic acid solution (10 mM acetic acid solution) under cooling conditions (4° C.) to remove the denaturing agent. The solution after folding was purified by HPLC [column: SHISEIDO Proteonavi], and as a result of mass spectrometry (ESI ionization method), the mass of the compound obtained corresponded with the mass of the target 2-6 diSialo(S1C-R26C-Q48C-A67C-N79-A88C) (SEQ ID NO. 100) (calculated value=33401.2 Da, actual value=33401.2 Da).

Example 4

Synthesis of Monosialo Glycosylated IFN-β

Example 4-1

Synthesis of 2-6 monoSialo(S1C-Q48C-N79C-K107C-R112C-R123C) (SEQ ID NO. 93)

With IFN 1-78(S1Thi-C30Acm-Q48C)Ethan (SEQ ID NO. 3) and IFN 79-165(N79C-K107C-R112C-R123C-C140Acm) (SEQ ID NO. 31), monosialo glycosylated IFN-β was synthesized by a method similar to (Example 3-1) except that the bromoacetylated monosialo sugar chain mixture represented by the following Formulae (9) and (10) (compound ratio 1:1) (5 equivalents) were alternatively used. As a result of performing mass spectrometry (ESI ionization method), the mass of the compound obtained corresponded with the mass of the target 2-6 monoSialo (S1C-Q48C-N79C-K107C-R112C-R123C) (calculated value=31557.2 Da, actual value=31556.6 Da). The results of mass spectrometry for (Example 3-1) and (Example 4-1) are shown in FIG. 1.

[Chemical Formula 25]

Formula (9)

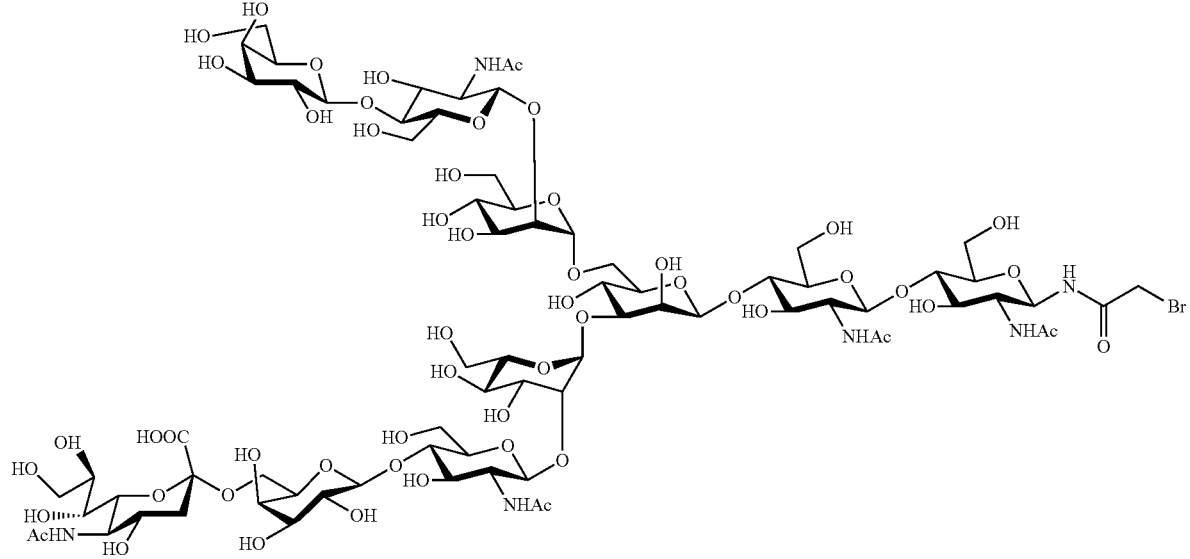

[Chemical Formula 26]

Formula (10)

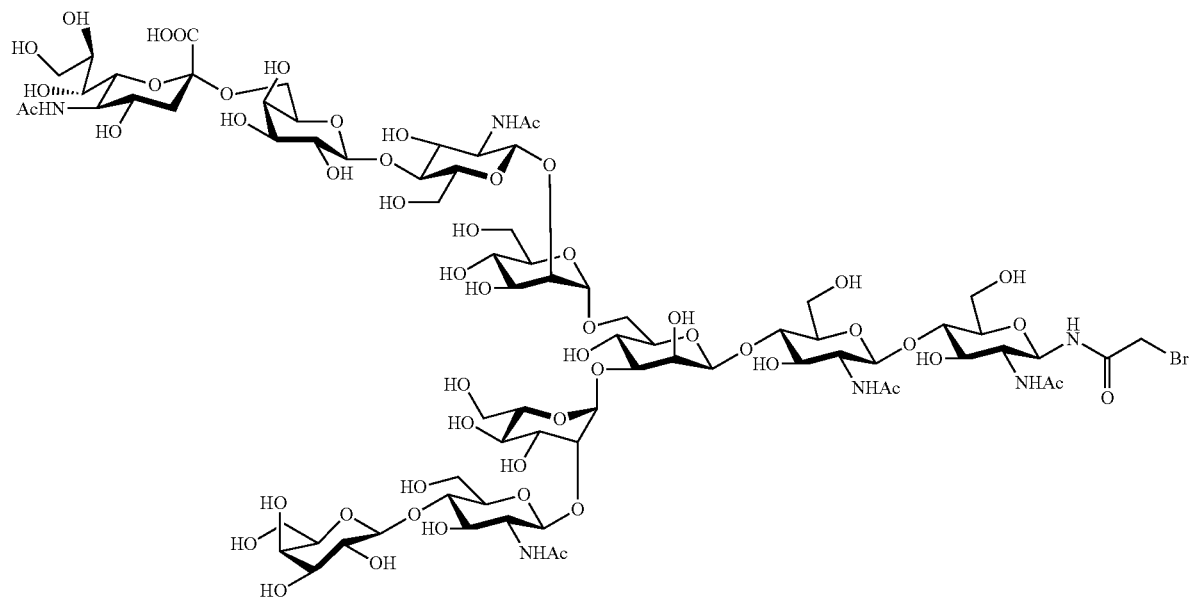

The compounds obtained in (Example 3-1) and (Example 4-1) were analyzed by SDS-PAGE and reverse phase HPLC [column: Waters BEH300]. The result of SDS-PAGE is shown in FIG. 2.

Looking at the result of SDS-PAGE, it was suggested that both compounds were uniformly glycosylated since clear bands were detected. Similarly, analysis by reverse phase HPLC also yielded data suggesting uniform glycosylation (Data not shown).

Moreover, the sugar chain portion was cleaved out from the compounds obtained in (Example 3-1) and (Example 4-1) by adding Endo-β-N-acetylglucosaminidase (Endo-M) (Tokyo Chemical Industry Co., Ltd.) under phosphate buffer (0.1 M phosphoric acid) solution at pH 6.0. The result of analysis by normal phase HPLC [column: Shodex NH2P-50] after labeling the reducing terminal of the free sugar chain obtained with 2-Aminobenzoic acid (Sigma Aldrich) is shown in FIG. 3. As a result of sugar chain structure analysis, a peak was confirmed at a retention time similar to the target disialo sugar chain, and the addition of the target sugar chain was confirmed.

Example 4-2

Synthesis of Other Monosialo Glycosylated IFN-β

The synthesis of the compounds shown below was performed with a method similar to (Example 4-1). 2-6 monoSialo(S1C-N3C-Q48C-N79C-K107C-R112C) (SEQ ID NO. 4-1) 2-6 monoSialo(S1C-Q48C-N79C-K107C) (SEQ ID NO. 95)

Example 5

Synthesis of Trisialo Glycosylated IFN-β

Example 5-1

Synthesis of 2-6 TriSialo(S1C-Q48C-N79C-K107C-R112C-R123C) (SEQ ID NO. 96)

With IFN 1-78(S1Thi-C30Acm-Q48C)Ethan (SEQ ID NO. 3) and IFN 79-165(N79C-K107C-R112C-R123C-C140Acm) (SEQ ID NO. 31), trisialo glycosylated IFN-β was synthesized by a method similar to (Example 3-1) except that the bromoacetylated trisialo sugar chain represented by the following Formula (11) (5 equivalents) was added. As a result of performing mass spectrometry (ESI ionization method), the mass of the compound obtained corresponded with the mass of the target 2-6 triSialo(S1C-Q48C-N79C-K107C-R112C-R123C) (calculated value=37244.3 Da, actual value=37243.2 Da).

[Chemical Formula 27]

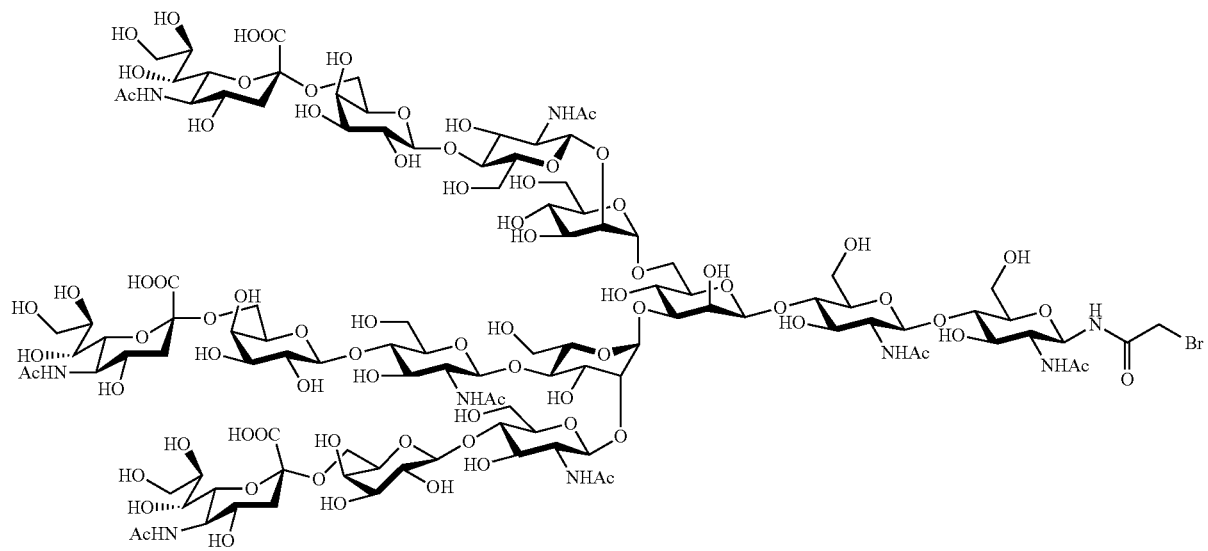

Formula (11)

Example 5-2

Synthesis of Other Trisialo Glycosylated IFN-β

The synthesis of the compound shown below was performed with a method similar to (Example 5-1). 2-6 triSialo (S1C-Q48C-N79C-K107C) (SEQ ID NO. 97)

Example 6

Synthesis of Tetrasialo Glycosylated IFN-β

[Chemical Formula 28]

Example 6-1

Synthesis of 2-6 TetraSialo(S1C-Q48C-N79C-K107C-R112C-R123C) (SEQ ID NO. 98)

With IFN 1-78(S1Thi-C30Acm-Q48C)Ethan (SEQ ID NO. 3) and IFN 79-165(N79C-K107C-R112C-R123C-C140Acm) (SEQ ID NO. 31), tetrasialo glycosylated IFN-β was synthesized by a method similar to (Example 3-1) except that the bromoacetylated tetrasialo sugar chain represented by the following Formula (12) (5 equivalents) was alternatively used. As a result of performing mass spectrometry (ESI ionization method), the mass of the compound obtained corresponded with the mass of the target 2-6 tetraSialo(S1C-Q48C-N79C-K107C-R112C-R123C) (calculated value=41183.8 Da, actual value=41182.6 Da).

Formula (12)

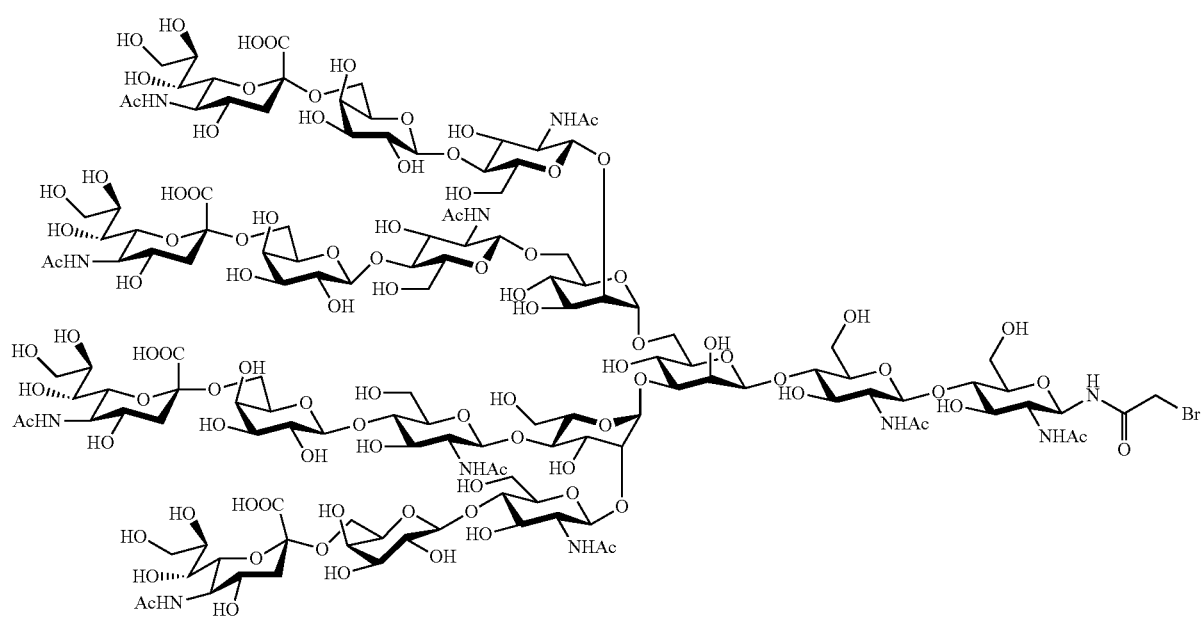

Example 6-2

Synthesis of Other Tetrasialo Glycosylated IFN-β

The synthesis of the compound shown below was performed with a method similar to (Example 6-1). 2-6 tetraSialo(S1C-Q48C-N79C-K107C) (SEQ ID NO. 99)

Mass spectrometry results of compounds obtained in Example 3-1, Example 3-2, Example 3-3, Example 3-4, Example 4-1, Example 4-2, Example 5-1, Example 5-2, Example 6-1, and Example 6-2 are shown in (Table 3) below.

TABLE 3

| Example Compound | | Theoretical value (MW) | Actual value (MW) | Ionization method |
|---|---|---|---|---|
| 3-1 | 2-6 diSialo (S1C-Q48C-N79C-K107C-R112C-R123C) | 33304.8 | 33303.6 | ESI |
| 3-2 | 2-6 diSialo (Q48C-S75C-N79C-K107C-R112C-E136C) | 33331.8 | 33331.2 | ESI |
| 3-3 | 2-3 diSialo (S1C-N3C-Q48C-N79C-K107C-R112C) | 33346.9 | 33346.6 | ESI |

TABLE 3-continued

| Example | Compound | Theoretical value (MW) | Actual value (MW) | Ionization method |
|---|---|---|---|---|
| 3-4 | 2-6 diSialo (S1C-N3C-Q48C-N79C-K107C-R112C) | 33346.9 | 33346.2 | ESI |
| 3-4 | 2-6 diSialo (S1C-Q48C-N79C-T99C-K107C-R112C) | 33359.9 | 33361.2 | ESI |
| 3-4 | 2-6 diSialo (S1C-Q48C-N79C-K107C-R112C-H130C) | 33323.8 | 33325.0 | ESI |
| 3-4 | 2-6 diSialo (S1C-Q48C-N79C-K107C-R112C-E136C) | 33331.8 | 33333.2 | ESI |
| 3-4 | 2-6 diSialo (S1C-Q48C-N79C-K107C-R112C-H139C) | 33323.8 | 33325.2 | ESI |
| 3-4 | 2-6 diSialo (S1C-Q48C-N79C-K107C-R112C-R164C) | 33304.8 | 33306.4 | ESI |
| 3-4 | 2-6 diSialo (S1C-Y29C-Q48C-N79C-K107C-E136C) | 33324.9 | 33325.4 | ESI |
| 3-4 | 2-6 diSialo (S1C-M35C-Q48C-N79C-K107C-E136C) | 33356.8 | 33356.2 | ESI |
| 3-4 | 2-6 diSialo (S1C-E14C-Q48C-N79C-K107C-E136C) | 33358.9 | 33358.8 | ESI |
| 3-4 | 2-6 diSialo (S1C-Q48C-S75C-N79C-K107C-E136C) | 33401.0 | 33400.4 | ESI |
| 3-4 | 2-6 diSialo (S1C-E28C-Q48C-R70C-N79C) | 31093.8 | 31093.2 | ESI |
| 3-4 | 2-6 diSialo (S1C-Q48C-N79C-K107C-R112C) | 31094.8 | 31094.0 | ESI |
| 3-4 | 2-6 diSialo (S1C-Q48C-N79C-K107C) | 28884.8 | 28883.6 | ESI |
| 3-4 | 2-6 diSialo (S1C-N79C-K107C-E136C) | 28883.8 | 28882.6 | ESI |
| 3-4 | 2-6 diSialo (S1C-N3C-Q48C-N79C) | 28898.9 | 28898.6 | ESI |
| 3-4 | 2-6 diSialo (E41C-S75C-N79C-E103C-K107C-E136C) | 33357.9 | 33356.9 | ESI |
| 3-4 | 2-6 diSialo (E41C-S75C-N79C-E106C-K107C-E136C) | 33357.9 | 33356.6 | ESI |
| 3-4 | 2-6 diSialo (E41C-S75C-N79C-K107C-D109C-E136C) | 33372.0 | 33370.5 | ESI |
| 3-4 | 2-6 diSialo (E41C-S75C-N79C-K107C-R112C-E136C) | 33330.9 | 33329.6 | ESI |
| 3-4 | 2-6 diSialo (E41C-S75C-N79C-K107C-L115C-E136C) | 33373.9 | 33372.7 | ESI |
| 3-4 | 2-6 diSialo (E41C-S75C-N79C-K107C-L119C-E136C) | 33373.9 | 33372.6 | ESI |
| 3-4 | 2-6 diSialo (N24C-N79C-K107C-R112C-E136C) | 31066.8 | 31066.0 | ESI |
| 3-4 | 2-6 diSialo (G25C-N79C-K107C-R112C-E136C) | 31123.8 | 31123.4 | ESI |
| 3-4 | 2-6 diSialo (K32C-N79C-K107C-R112C-E136C) | 31052.7 | 31052.4 | ESI |
| 3-4 | 2-6 diSialo (M35C-N79C-K107C-R112C-E136C) | 31049.7 | 31049.8 | ESI |
| 3-4 | 2-6 diSialo (D38C-N79C-K107C-R112C-E136C) | 31065.8 | 31065.4 | ESI |
| 3-4 | 2-6 diSialo (E41C-N79C-K107C-R112C-E136C) | 31051.8 | 31051.2 | ESI |
| 3-4 | 2-6 diSialo (F7C-N79C-K107C-R112C-E136C) | 31033.7 | 31033.2 | ESI |
| 3-4 | 2-6 diSialo (Q48C-N79C-K107C-R112C-E136C) | 31052.7 | 31052.4 | ESI |
| 3-4 | 2-6 diSialo (S75C-N79C-K107C-R112C-E136C) | 31093.8 | 31093.4 | ESI |
| 3-4 | 2-6 diSialo (E41C-S75C-N79C-K107C-E136C) | 31120.9 | 31119.5 | ESI |
| 3-4 | 2-6 diSialo (E42C-S75C-N79C-K107C-E136C) | 31120.9 | 31119.7 | ESI |
| 3-4 | 2-6 diSialo (Q45C-S75C-N79C-K107C-E136C) | 31121.9 | 31120.4 | ESI |
| 3-4 | 2-6 diSialo (L46C-S75C-N79C-K107C-E136C) | 31136.8 | 31135.6 | ESI |
| 3-4 | 2-6 diSialo (Q47C-S75C-N79C-K107C-E136C) | 31121.9 | 31120.7 | ESI |
| 3-4 | 2-6 diSialo (Q48C-S75C-N79C-K107C-E136C) | 31121.9 | 31120.5 | ESI |
| 3-4 | 2-6 diSialo (F49C-S75C-N79C-K107C-E136C) | 31102.8 | 31101.4 | ESI |
| 3-4 | 2-6 diSialo (Q50C-S75C-N79C-K107C-E136C) | 31121.9 | 31120.7 | ESI |
| 3-4 | 2-6 diSialo (N79C-K107C-R112C-E136C) | 28814.7 | 28814.2 | ESI |
| 3-4 | 2-6 diSialo (E28C-N79C-K107C-E136C) | 28841.8 | 28841.2 | ESI |
| 3-4 | 2-6 diSialo (M35C-N79C-K107C-E136C) | 28839.7 | 28839.0 | ESI |
| 3-4 | 2-6 diSialo (R70C-N79C-K107C-E136C) | 28814.7 | 28814.2 | ESI |
| 3-4 | 2-6 diSialo (S75C-N79C-K107C-E136C) | 28883.8 | 28682.6 | ESI |
| 3-4 | 2-3 diSialo (S1C-Q48C-N79C-K107C) | 28884.8 | 28888.4 | ESI |
| 4-1 | 2-6 diSialo (S1C-Q48C-N79C-K107C-R112C-R123C) | 31557.2 | 31556.6 | ESI |
| 4-2 | 2-6 diSialo (S1C-Q48C-N79C-K107C) | 27719.8 | 27719.4 | ESI |
| 4-2 | 2-6 diSialo (S1C-N3C-Q48C-N79C-K107C-R112C) | 31599.3 | 31598.8 | ESI |
| 5-1 | 2-6 diSialo (S1C-Q48C-N79C-K107C-R112C-R123C) | 37244.3 | 37243.2 | ESI |
| 5-2 | 2-6 diSialo (S1C-Q48C-N79C-K107C) | 31511.1 | 31512.8 | ESI |
| 6-1 | 2-6 diSialo (S1C-Q48C-N79C-K107C-R112C-R123C) | 41183.8 | 41182.6 | ESI |
| 6-2 | 2-6 diSialo (S1C-Q48C-N79C-K107C) | 34137.5 | 34139.0 | ESI |

Example 7

Pharmacokinetics of Quadruple, Quintuple, and Sextuple DiSialosugar Chain-Modified IFNβ in Mice

Example 7-11

Preparation of Administration Agents and Reagents 2-6 diSialo(S1C-Q48C-N79C-K107C) (SEQ ID NO. 61), 2-6 diSialo(S1C-Q48C-N79C-K107C-R112C) (SEQ ID NO. 60), 2-6 diSialo(S1C-Q48C-N79C-K107C-R112C-R123C) (SEQ ID NO. 46), and AVONEX® (Biogen Idec) were prepared at 588 nM with an acetate buffer comprising L-Arginine and polysorbate. AVONEX® is a natural IFN-β (IFN-β-1a) which was employed as a control agent. AVONEX® is manufactured with a CHO cell line, has one sugar chain at the position that is position 80 of natural human interferon β (the position corresponding to position 79 in the amino acid sequence represented by SEQ ID NO. 1 herein), and its sugar chain structure may be various sugar chains of complex N-linked sugar chains for each polypeptide.

Example 7-2

Administration and Blood Collection

Mice (Balb/c mouse, male, 8 weeks old, body weight 21-23 g) were administered at a dose of 2352 pmol/kg under full feeding from the dorsal subcutaneous with an insulin syringe Myjector 29 G×½ (Terumo Corporation) at a volume of 4 mL/kg. 75 μL of blood was collected from the tail vein with a heparin treated hematocrit capillary tube (HIRSHMANN LABORGERATE) before subcutaneous administration as well as at 10 minutes, 30 minutes, 1 hour, 2 hours, 4 hours, 6 hours, 8 hours, 12 hours, 16 hours, 24 hours, are 30 hours after administration. This was quickly mixed with 6 nM EDTA-PBS at the same volume as the collected blood and subjected to centrifugal separation (15000 rpm, 4 degrees, 10 minutes). 90 µL of the supernatant was collected as blood plasma sample. The blood plasma sample was stored frozen until used for measurement.

Example 7-2

Measurement of Blood Concentration

Human interferon β ELISA kit (Kamakura Techno-Science) was employed for the measurement of blood concentration of IFN-β. Quadruple-sextuple diSialosugar chain-modified IFN-β and AVONEX® from the same lot as those administered were employed as standards for creating a standard curve, and prepared to 200 pM, 100 pM, 50 pM, 25 pM, 12.5 pM, 6.25 pM, and 3.125 pM with the diluent attached to the kit. Blank blood plasma was added to the standard curve according to the dilution ratio of the blood plasma sample so that the amount brought in will be the same. A graph representation of the transition of IFN-β plasma concentration obtained is shown in FIG. 4.

As is shown in FIG. 4, when IFN-β concentration in blood plasma are compared, quadruple, quintuple, and sextuple disialosugar chain-modified IFN-β maintained a much higher plasma concentration than the control agent AVONEX® at any point of measurement, confirming improvement or retentivity in blood. In addition, since Tmax becomes slower as the number of diSialoglycosylation increased, it was thought that the transfer of the compound from the subcutaneous to the blood was delayed. Cmax or blood concentration in the dissipation phase became higher as the number of diSialoglycosylation increased. From this, it was shown that by adding diSialosugar chains, the stability of IFN-β in vivo is improved according to the number of diSialosugar chains.

Example 7-4

Calculation of Pharmacokinetical Parameters

From the transition of IFN-β plasma concentration obtained, using moment analysis, blood concentration area under the curve (AUC∞) was calculated by the trapezoidal rule. Moreover, maximum blood concentration (Cmax) and time to maximum blood concentration (Tmax) were determined from half-life in blood (t½), mean retention time (MRT), and the actual value from subcutaneous administration. The pharmacokinetical parameters obtained are shown in FIG. 5.

As is shown in FIG. 5, it was also shown from the results of moment analysis that the effect of diSialoglycosylated IFN-β for improving t½, and AUC, and MRT will increase according to the number of modification.

Example 8

Pharmacokinetics of DiSialoSugar Chain and MonoSialoSugar Chain Quadruple Glycosylated IFN-β in Mice Example 8-1

Preparation of Administration Agents and Reagents 2-6 diSialo(S1C-Q48C-N79C-K107C) (SEQ ID NO. 61), 2-6 monoSialo(S1C-Q48C-N79C-K107C) (SEQ ID NO. 95), and AVONEX® were prepared at 112 nM with an acetate buffer comprising L-Arginine and polysorbate.

Example 8-2

Administration and Blood Collection

Mice (Balb/c mouse, male, 8 weeks old, body weight 21-23 g) were administered at a dose of 448 pmol/kg under full feeding from the tail vein or the dorsal subcutaneous with an insulin syringe Myjector 29 G×½ (Terumo Corporation) at a volume of 4 mL/kg. 75 µL of blood was collected from the tail vein with a heparin treated hematocrit capillary tube (HIRSHMANN LABORGERATE) before subcutaneous administration as well as at 2 minutes, 10 minutes, 30 minutes, 1 hour, 3 hours, 6 hours, 8 hours, and 24 hours after administration for intravenous administration, and before administration as well as at 10 minutes, 30 minutes, 1 hour, 2 hours, 4 hours, 6 hours, 8 hours, 12 hours, 16 hours, 24 hours, are 30 hours after administration for subcutaneous administration. This was quickly mixed with EDTA-PBS at the same volume as the collected blood, and subjected to centrifugal separation (15000 rpm, 4 degrees, 10 minutes). 90 µL of the supernatant was collected as blood plasma sample. The blood plasma sample was stored frozen until used for measurement.

Example 8-3

Measurement of Blood Concentration

Human interferon β ELISA kit (Kamakura Techno-Science) was employed for the measurement of blood concentration of IFN-β. Quadruple diSialosugar chain-glycosylated IFN-β, quadruple monoSialosugar chain-glycosylated IFN-β, and AVONEX® from the same lot as those administered were employed as standards for creating a standard curve, and prepared to 200 pM, 100 pM, 50 pM, 25 pM, 12.5 pM, 6.25 pM, and 3.125 pM with the diluent attached to the kit. Blank blood plasma was added to the standard curve according to the dilution ratio of the blood plasma sample so that the amount brought in will be the same. A graph representation of the transition of IFN-β plasma concentration obtained is shown in FIG. 6.

As is shown in FIG. 6, when IFN-β concentration in blood plasma are compared, 2-6 diSialo(S1C-Q48C-N79C-K107C) was confirmed to be drastically improved in all of t½, AUC∞, and MRT than the control agent AVONEX® at any point of measurement. In contrast, in both subcutaneous administration and tail intravenous administration, 2-6 monoSialo(S1C-Q48C-N79C-K107C) in which sialylation was incomplete showed drastically low transition of blood concentration than the control agent AVONEX®. From this result, it was shown that all of the sugar chain terminals being sialylated largely contributes to improvement of retentivity of IFN-β in blood.

Example 8-4

Calculation of Pharmacokinetical Parameters

From the transition of IFN-β plasma concentration obtained, using moment analysis, plasma concentration area under the curve (AUC) was calculated by the trapezoidal rule. Moreover, predicted initial concentration (C0) for intravenous administration was determined by the extrapolation method, and further, maximum blood concentration (Cmax) and time to maximum blood concentration (Tmax) were determined from half-life in blood (t½), mean retention time (MRT), and the actual value from subcutaneous administration. The result is shown in FIG. 7.

As is shown in FIG. 7, it was also confirmed from the results of moment analysis that quadruple diSialosugar chain-modified IFN-β had an effect of improving t½, AUC∞, and MRT more than the control agent AVONEX®. On the other hand, quadruple monoSialosugar chain-modified IFN-β showed lower values for any of t½, AUC∞, and MRT than the control agent AVONEX®, confirming that it dissipates more quickly from the blood.

Example 9

Pharmacokinetics of Sextuple DiSialoSugar Chain and MonoSialoSugar Chain-Glycosylated IFN-β in Mice Example 9-1

Preparation of Administration Agents and Reagents 2-6 diSialo(S1C-Q48C-N79C-K107C-R112C-R123C) (SEQ ID NO. 46), 2-6 monoSialo(S1C-Q48C-N79C-K107C-R112C-R123C) (SEQ ID NO. 93), and AVONEX® were prepared at 588 nM with an acetate buffer comprising L-Arginine and polysorbate.

Example 9-2

Administration and Blood Collection

Mice (Balb/c mouse, male, body weight 21-23 g) were administered at a dose of 2352 pmol/kg under full feeding from the tail vein with an insulin syringe Myjector 29 G×½ (Terumo Corporation) at a volume of 4 mL/kg. 75 µL of blood was collected from the tail vein with a heparin treated hematocrit capillary tube (HIRSHMANN LABORGERATE) before intravenous administration as well as at 2 minutes, 10 minutes, 30 minutes, 1 hour, 3 hours, 6 hours, 8 hours, and 24 hours after administration. This was quickly mixed with EDTA-PBS at the same volume as the collected blood, and subjected to centrifugal separation (15000 rpm, 4 degrees, 10 minutes). 90 µL of the supernatant was collected as blood plasma sample. The blood plasma sample was stored frozen until used for measurement.

Example 9-3

Measurement of Blood Concentration

Human interferon β ELISA kit (Kamakura Techno-Science) was employed for the measurement of blood concentration of IFN-β. Quadruple diSialosugar chain-glycosylated IFN-β, quadruple monoSialosugar chain-glycosylated IFN-β, and AVONEX® from the same lot as those administered were employed as standards for creating a standard curve, and prepared to 200 pM, 100 pM, 50 pM, 25 pM, 12.5 pM, 6.25 pM, and 3.125 pM with the diluent attached to the kit. Blank blood plasma was added to the standard curve according to the dilution ratio of the blood plasma sample so that the amount brought in will be the same. A graph representation of the transition of IFN-β plasma concentration obtained is shown in FIG. 8.

Results similar to the above-described quadruple-modified IFN-β were also obtained for sextuple-modified IFN-β.

In other words, 2-6 diSialo(S1C-Q48C-N79C-K107C-R112C-R123C) was confirmed to be drastically improved in all of t½, AUC∞, and MRT than the control agent AVONEX®. On the other hand, 2-6 monoSialo(S1C-Q48C-N79C-K107C-R112C-R123C) showed drastically low transition of blood concentration than the control agent AVONEX® for tail intravenous administration. From this, it was also confirmed that for sextuple-glycosylated IFN-β, similarly to quadruple-glycosylated IFN-β, all of the sugar chain terminals being sialylated is extremely important for improvement of retentivity of IFN-β in blood.

Example 9-4

Calculation of Pharmacokinetical Parameters

From the transition of IFN-β plasma concentration obtained, using moment analysis, plasma concentration area under the curve (AUC) was calculated by the trapezoidal rule. Moreover, predicted initial concentration (C0) for intravenous administration was determined by the extrapolation method, and further, half-life in blood (t½) and mean retention time (MRT) were determined. The result is shown in FIG. 9.

As is shown in FIG. 9, it was also confirmed from the results of moment analysis that 2-6 diSialo(S1C-Q48C-N79C-K107C-R112C-R123C) drastically improves all of t½, AUC∞, and MRT more than the control agent AVONEX®. On the other hand, 2-6 monoSialo(S1C-Q48C-N79C-K107C-R112C-R123C) showed lower values for any of t½, AUC∞, and MRT than the control agent AVONEX®, indicating that it dissipates more quickly from the blood.

Example 10

Pharmacokinetics of Sextuple DiSialoSugar Chain-Modified IFN-β and PEG20K-Modified IFN-β in Mice Example 10-1

Preparation of Administration Agents and Reagents 2-6 diSialo(S1C-Q48C-N79C-K107C-R112C-R123C) (SEQ ID NO. 46), PEG20K-modified IFN-β, and AVONEX® were prepared at 558 nM with an acetate buffer comprising L-Arginine and polysorbate.

Example 10-2

Administration and Blood Collection

Mice (Balb/c mouse, male, 8 weeks old, body weight 21-23 g) were administered at a dose of 2352 pmol/kg under full feeding from the dorsal subcutaneous with an insulin syringe Myjector 29 G×½ (Terumo Corporation) at a volume of 4 mL/kg. 75 µL of blood was collected from the tail vein with a heparin treated hematocrit capillary tube (HIRSHMANN LABORGERATE) before subcutaneous administration as well as at 10 minutes, 30 minutes, 1 hour, 2 hours, 4 hours, 6 hours, 8 hours, 12 hours, 16 hours, 24 hours, are 30 hours after administration. This was quickly mixed with EDTA-PBS at the same volume as the collected blood, and subjected to centrifugal separation (15000 rpm, 4 degrees, 10 minutes). 90 µL of the supernatant was collected as blood plasma sample. The blood plasma sample was stored frozen until used for measurement.

Example 10-3

Measurement of Blood Concentration

Human interferon β ELISA kit (Kamakura Techno-Science) was employed for the measurement of blood concentration of IFN-β. Sextuple diSialosugar chain-modified IFN-β, PEG20K-modified IFN-β, and AVONEX® from the same lot as those administered were employed as standards for creating a standard curve, and prepared to 200 pM, 100 pM, 50 pM, 25 pM, 12.5 pM, 6.25 pM, and 3.125 pM with the diluent attached to the kit. Blank blood plasma was added to the standard curve according to the dilution ratio of the blood plasma sample so that the amount brought in will be the same. A graph representation of the transition of IFN-β plasma concentration obtained is shown in FIG. 10.

Example 10-4

Calculation of Pharmacokinetical Parameters

From the transition of IFN-β plasma concentration obtained, using moment analysis, blood concentration area under the curve (AUC) was calculated by the trapezoidal rule. Moreover, predicted initial concentration (C0) for intravenous administration was determined by the extrapolation method, and further, half-life in blood (t½) and mean retention time (MRT) were determined. The result is shown in FIG. 11.

As is shown in FIGS. 10 and 11, from the results of transition of plasma concentration and moment analysis, sextuple diSialosugar chain-modified IFN-β and PEG20K-modified IFN-β both drastically improved all of t½, AUC∞, and MRT than AVONEX®. Moreover, it was seen that sextuple diSialosugar chain-modified IFN-β surpasses PEG20K-modified IFN-β in regards to AUC∞ and Cmax.

For t½ and MRT, comparison between sextuple diSialosugar chain-modified IFN-β and PEG20K-modified IFN-β gave comparable results.

From the results, it was shown that sextuple diSialosugar chain-modified IFN-β improves the stability of AVONEX® in vivo to a comparable level with PEG20K or higher.

Example 11

In Vivo Antitumor Activity of Quadruple, Quintuple, and Sextuple DiSialosugar Chain-Modified IFN-β

The antitumor activity of quadruple, quintuple, and sextuple diSialosugar chain-modified IFN-β in vivo was evaluated with cancer-bearing mice.

Example 11-1

Cell Culture

Cancer-bearing mice prepared by inoculating Daudi cells which are human Burkitt's lymphoma was employed for the antitumor activity test. The medium employed was RPMI1640 (Invitrogen) supplemented with 10% Fetal Bovine Serum (GIBCO) subjected to inactivation treatment at 56° C. for 30 minutes and penicillin/streptomycin (SIGMA). The culture plate employed was a Non-treat dish (IWAKI). Culture was performed at 37° C. under 5% $CO_2$ concentration condition and passaged once every 2-3 days.

Example 11-2

Preparation of Cancer-Bearing Mice

Cultured Daudi cells were collected in a tube and subjected to centrifugal separation (1300 rpm, 4 degrees, 3 minutes). The supernatant was removed with an aspirator, HBSS (Nacalai) was added, and cells were suspended. This was then again subjected to centrifugal separation, and the supernatant was removed. This cell washing treatment was performed for a total of three times. In addition, the number of cells was calculated with a hermocytometer, and a cell suspension was prepared with HBSS at $2 \times 10^8$ cells/mL. Immediately before Daudi cell inoculation, Matrigel (BD) at the same volume as the cell suspension was added to allow double dilution, and a cell suspension for inoculation was prepared. The cell suspension for inoculation was stored on ice until immediately before inoculation. Somnopentyl (Kyoritsu Seiyaku) was employed as the anesthetic ding diluted to 5 mg/mL with PBS. 300 μL of the anesthetic drug was intraperitoneally administered to SCID mice (C.B-17/Icr-scid/scidJcl mouse, male, 6 weeks old) (CLEA Japan) with an insulin syringe Myjector 29 G×½ (Terumo Corporation). After confirming that anesthesia was introduced, a shaver was used to shave the right flank of the mice. A 26 G ½ injection needle (Terumo) and a 1 mL glass syringe (Terumo) were employed to subcutaneously inoculate 100 μL of the cell suspension for inoculation.

Approximately 30 days after the cell inoculation treatment, the major axis (mm) and the minor axis (mm) of the tumor tissue formed were measured with a caliper (Mitsutoyo). The tumor volume ($mm^3$) was determined with the numeric values obtained. The tumor volume was calculated with the formula: tumor volume ($mm^3$)=major axis (mm)× minor axis (mm)×minor axis (mm)×0.5, and the cancer-bearing mice were grouped into four groups (n=4/group). The tumor volume at the time of grouping was approximately 800 $mm^3$.

Example 11-3

Preparation of Administration Fluid 2-6 diSialo(S1C-Q48C-N79C-K107C) (SEQ ID NO. 61), 2-6 diSialo(S1C-Q48C-N79C-K107C-R112C) (SEQ ID NO. 60), 2-6 diSialo(S1C-Q48C-N79C-K107C-R112C-R123C) (SEQ ID NO. 46), 2-6 diSialo(S1C-N3C-Q48C-N79C-K107C-R112C) (SEQ ID NO. 49), as well as the control agent AVONEX® were prepared at 588 nM with an acetate buffer comprising L-Arginine and polysorbate. The preparation of the administration fluid was performed immediately before administration.

Example 11-4

Administration Method

The administration fluid prepared was employed to administer to the dorsal subcutaneous so that the dose will be 2352 pmol/kg, at a volume of 4 mL/kg with an insulin syringe Myjector 29 G×½. The Vehicle administration group was administered an acetate buffer comprising L-Arginine and polysorbate employed for preparing the administration fluid at a volume of 4 mL/kg. The day of grouping and initial administration was set at day 0, and dorsal subcutaneous administration was performed on alternate days for five times until day 9.

Example 11-5

Evaluation of Antitumor Activity Power

Cancer tissue was resected from mice on day 24 after start of administration, and the wet tissue weight was measured. As an indicator of antitumor activity, the relative value of the wet tissue weight of the quadruple-sextuple diSialosugar chain-modified IFN-β and AVONEX® administration group when the wet tissue weight of the Vehicle administration group was set as 100% (% T/C: test/control) was calculated. The result is shown in FIG. 12.

As is shown in FIG. 12, the relative value of the wet tissue weight of the cancer tissue (% T/C) was 44.5% for the AVONEX® administration group, whereas the values were 0.3% for the 2-6 diSialo(S1C-Q48C-N79C-K107C-R112C-R123C) administration group, 0.4% for the 2-6 diSialo(S1C-N3C-Q48C-N79C-K107C-R112C) administration group, 18.9% for the 2-6 diSialo(S1C-Q48C-N79C-K107C-R112C) administration group, and 28.1% for the 2-6 diSialo (S1C-Q48C-N79C-K107C) administration group, and the quadruple, quintuple, and sextuple diSialosugar chain-modified IFN-β of the present invention almost eradicated cancer tissue, or showed superior antitumor activity to an extent that greatly reduced cancer tissue.

From the above results, when subcutaneous administration was carried out once a day, alternate day×5 times, and at 2352 pmol/kg, a trend of strong antitumor activity was observed as the number of diSialoglycosylation increased.

Example 12

In Vivo Antitumor Activity of Sextuple DiSialosugar/MonoSialosugar Chain-Modified IFN-β

Cells were cultured with a method similar to (Example 11-1), and cancer-bearing mice were prepared with a method similar to (Example 11-2).

The administration fluid was prepared with a method similar to (Example 11-3) except that the administration fluid of (Example 11-3) was 2-6 diSialo(S1C-Q48C-N79C-K107C-R112C-R123C) (SEQ ID NO. 46), 2-6 monoSialo (S1C-Q48C-N79C-K107C-R112C-R123C) (SEQ ID NO. 93), and the control agent AVONEX®, and administered to cancer-bearing mice with a method similar to (Example 11-4).

Cancer tissue was resected from mice on day 22 after start of administration, and the wet tissue weight was measured. As an indicator of antitumor activity, the relative value of the wet tissue weight of the AVONEX® administration group when the wet tissue weight of the Vehicle administration group was set at 100% (% T/C: test/control) was calculated. The result is shown in FIG. 13.

As is shown in FIG. 13, the relative value of the wet tissue weight of the cancer tissue (% T/C) was 63.0% for the AVONEX® administration group, whet as the value was 1.3% for the sextuple diSialosugar chain-modified IFN-β administration group, and strong antitumor activity was confirmed. On the other hand, the value was 79.3% for the sextuple monoSialosugar chain-modified IFN-β administration group.

From the above results, when subcutaneous administration was carried out once a day, alternate day x 5 times, and at 2352 pmol/kg, with sextuple diSialosugar chain-modified IFN-β, strong antitumor activity to an extent that almost eradicated cancer tissue that was far superior than the AVONEX® administration group was shown. On the other hand, with sextuple monoSialosugar chain-modified wherein only one of the two non-reducing terminals is sialylated, antitumor activity superior than the AVONEX® administration group was not seen. From this, it was found that all of the non-reducing terminals being sialylated is important for antitumor activity.

Example 13

In Vivo Antitumor Activity of Sextuple DiSialosugar/TriSialosugar/TetraSialosugar Chain-Modified IFN-β

Cells were cultured with a method similar to (Example 11-1), and cancer-bearing mice were prepared with a method similar to (Example 11-2).

The administration fluid was prepared with a method similar to (Example 11-3) except that the administration fluid of (Example 11-3) was 2-6 diSialo(S1C-Q48C-N79C-K107C-R112C-R123C) (SEQ ID NO. 46), 2-6 triSialo(S1C-Q48C-N79C-K107C-R112C-R123C) (SEQ ID NO. 96), 2-6 tetraSialo(S1C-Q48C-N79C-K107C-R112C-R123C) (SEQ ID NO. 98), and the control agent AVONEX®, and administered to cancer-bearing mice with a method similar to (Example 11-4).

Cancer tissue was resected from mice on day 21 after start of administration, and the wet tissue weight was measured. As an indicator of antitumor activity, the relative value of the wet tissue weight of the AVONEX® administration group when the wet tissue weight of the Vehicle administration group was set at 100% (% T/C: test/control)) was calculated. The result is shown in FIG. 14.

As is shown in FIG. 14, the relative value of the wet tissue weight of the cancer tissue (% T/C) was 55.5% for the AVONEX® administration group, whereas the values were 3.6% for the sextuple diSialosugar chain-modified IFN-β administration group, 9.1% for the sextuple tetraSialosugar chain-modified IFN-β administration group, and 28.7% for the sextuple triSialosugar chain-modified IFN-β administration group, and it was shown that any of the sextuple sugar chain-modified IFN-β have strong antitumor activity.

In regards to the sugar chain structure, when focusing on the difference in the number of branches in the sugar chain, although the sextuple biantennary diSialosugar chain-modified form shows strong antitumor activity, the sextuple triantennary triSialosugar chain-modified form and the sextuple tetraantennary tetraSialosugar chain-modified form showed antitumor activity that was weaker than the sextuple diSialosugar chain-modified form. It is thought that the difference in cell growth inhibitory activity in vitro such as that shown in the result of Example 16 described below (Table 4) or the difference in blood kinetics in vivo and the like are possibly related to this.

Example 14

In Vivo Antitumor Activity of Sextuple DiSialosugar Chain-Modified IFN-β and PEG20K-Modified IFN-β

Cells were cultured with a method similar to (Example 11-1), and cancer-bearing mice were prepared with a method similar to (Example 11-2).

The administration fluid was prepared with a method similar to (Example 11-3) except that the administration fluid of (Example 11-3) was 2-6 diSialo(S1C-Q48C-N79C-K107C-R112C-R123C) (SEQ ID NO. 46), PEG20K-modified IFN-β and control agent AVONEX®, and administered to cancer-bearing mice with a method similar to (Example 11-4).

Cancer tissue was resected from mice on day 21 after start of administration, and the wet tissue weight was measured. As an indicator of antitumor activity, the relative value of the wet tissue weight of the AVONEX® administration group when the wet tissue weight of the Vehicle administration group was set at 100% (T/C %:test/control) was calculated. The result is shown in FIG. 15.

As is shown in FIG. 15, the relative value of the wet tissue weight of the cancer tissue (% T/C) was 62.6% for the AVONEX® administration group, whereas the value was 0.3% for the sextuple diSialosugar chain-modified IFN-β administration group, and extremely high antitumor activity to an extent that almost eradicated carter tissue was shown. On the other hand, the % T/C of the PEG20K-modified IFN-β administration group was 58.5% which was merely a comparable level to the control agent AVONEX® administration group. From this, it became clear that sextuple diSialosugar chain-modified IFNβ has extremely superior IFN-β activity compared to the control agent AVONEX® and the PEG20K-modified IFN-β knows as conventional technology.

Generally, as conventional technology, addition of PEG to polypeptides has been performed in order to improve physical stability or plasma stability of proteins. Also in (Example 10) of the present invention, PEGylated IFN-β showed significantly improved transition of blood concentration compared to AVONEX®. However, in (Example 14), PEGylated IFN-β only showed antitumor activity that was merely a comparable level to AVONEX®. In other words, no improvement was seen in regards to IFN-β antitumor activity with PEGylation that is generally known to have an effect of improving retentivity in blood, whereas the glycosylated IFN-β of the present invention surprisingly had significantly high retentivity in blood than AVONEX® as shown in (Example 10), and also was significantly improved in regards to antitumor activity. From this, it was shown that the glycosylated IFN-β of the present invention is extremely useful as a pharmaceutical compared to natural or PEGylated IFN-β.

Example 15

In Vitro Cell Growth Inhibitory Activity of Quadruple, Quintuple, and Sextuple-Glycosylated IFN-β

The cell growth inhibitory activity of quadruple, quintuple, and sextuple-glycosylated IFN-β in vitro was evaluated by the following method.

Human Burkitt's lymphoma cell strain Daudi was suspended in 10% Fetal bovine serum, 100 U/mL penicillin, and 100 µg/mL streptomycine-containing RPMI 1640 medium (10% FCS-RPMI1640) to $1.25 \times 10^5$ cells/mL. The cell suspension was seeded in a 96-well flat bottom plate at $1 \times 10^4$ cells/80 µL/well each. Further, 20 µL/well each of the multiply glycosylated IFN-β serially diluted with 10% FCS-RPMI1640 were added, and this was cultured in a $CO_2$ incubator adjusted to 5% $CO_2$ concentration at 37 degrees for 3 days. The cell growth inhibitory activity was measured with mitochondria dehydrogenase activity at day 3 of culture as the indicator with Cell counting kit-8 (DOJINDO) according to the manual attached to the kit.

Moreover, AVONEX® was used as the control. The IC50 value was calculated with GraphPad Prism. The results are shown in (Table 4) below.

TABLE 4

| Compound | IC(50) |
|---|---|
| Avonex | 4.34 ± 1.01 |
| PEG20K (N-terminus) | 26.58 ± 2.31 |
| 2-6 monoSialo (S1C-Q48C-N79C-K107C-R112C-R123C) | 1.33 ± 0.35 |
| 2-6 diSialo (S1C-Q48C-N79C-K107C-R112C-R123C) | 1.56 ± 0.20 |
| 2-6 monoSialo (S1C-N3C-Q48C-N79C-K107C-R112C) | 1.50 ± 0.75 |
| 2-6 diSialo (S1C-N3C-Q48C-N79C-K107C-R112C) | 1.98 ± 0.54 |
| 2-6 diSialo (S1C-Q48C-N79C-T99C-K107C-R112C) | 2.16 ± 0.95 |
| 2-6 diSialo (S1C-Q48C-N79C-K107C-R112C-H130C) | 1.29 ± 0.41 |
| 2-6 diSialo (S1C-Q48C-N79C-K107C-R112C-E136C) | 2.39 ± 0.85 |
| 2-6 diSialo (S1C-Q48C-N79C-K107C-R112C-H139C) | 2.81 ± 0.74 |
| 2-6 diSialo (S1C-Q48C-N79C-K107C-R112C-R164C) | 2.74 ± 0.50 |
| 2-6 diSialo (S1C-Y29C-Q48C-N79C-K107C-E136C) | 2.05 ± 0.77 |
| 2-6 diSialo (S1C-M35C-Q48C-N79C-K107C-E136C) | 1.75 ± 0.45 |
| 2-6 diSialo (S1C-E41C-Q48C-N79C-K107C-E136C) | 2.06 ± 0.39 |
| 2-6 diSialo (S1C-Q48C-S75C-N79C-K107C-E136C) | 1.95 ± 0.36 |
| 2-6 diSialo (Q48C-S75C-N79C-K107C-R112C-E136C) | 1.16 ± 0.12 |
| 2-6 diSialo (E41C-S75C-N79C-E103C-K107C-E136C) | 0.88 ± 0.25 |
| 2-6 diSialo (E41C-S75C-N79C-E106C-K107C-E136C) | 1.11 ± 0.47 |
| 2-6 diSialo (E41C-S75C-N79C-K107C-D109C-E136C) | 1.14 ± 0.47 |
| 2-6 diSialo (E41C-S75C-N79C-K107C-R112C-E136C) | 1.26 ± 0.60 |
| 2-6 diSialo (E41C-S75C-N79C-K107C-L115C-E136C) | 1.24 ± 0.60 |
| 2-6 diSialo (E41C-S75C-N79C-K107C-L119C-E136C) | 0.98 ± 0.46 |
| 2-3 diSialo (S1C-N3C-Q48C-N79C-K107C-R112C) | 1.65 ± 1.09 |
| 2-6 triSialo (S1C-Q48C-N79C-K107C-R112C-R123C) | 5.71 ± 1.06 |
| 2-6 tetraSialo (S1C-Q48C-N79C-K107C-R112C-R123C) | 25.2 ± 4.18 |
| 2-6 diSialo (S1C-E28C-Q48C-R70C-N79C) | 1.53 ± 0.53 |
| 2-6 diSialo (S1C-Q48C-N79C-K107C-R112C) | 1.97 ± 0.80 |
| 2-6 diSialo (N24C-N79C-K107C-R112C-E136C) | 1.03 ± 0.37 |
| 2-6 diSialo (Q25C-N79C-K107C-R112C-E136C) | 2.20 ± 0.77 |
| 2-6 diSialo (K32C-N79C-K107C-R112C-E136C) | 1.14 ± 0.27 |
| 2-6 diSialo (M35C-N79C-K107C-R112C-E136C) | 1.18 ± 0.40 |
| 2-6 diSialo (D38C-N79C-K107C-R112C-E136C) | 1.19 ± 0.39 |
| 2-6 diSialo (E41C-N79C-K107C-R112C-E136C) | 0.96 ± 0.23 |
| 2-6 diSialo (F7C-N79C-K107C-R112C-E136C) | 1.08 ± 0.13 |
| 2-6 diSialo (Q48C-N79C-K107C-R112C-E136C) | 0.99 ± 0.16 |
| 2-6 diSialo (S75C-N79C-K107C-R112C-E136C) | 1.13 ± 0.20 |
| 2-6 diSialo (E41C-S75C-N79C-K107C-E136C) | 1.04 ± 0.14 |
| 2-6 diSialo (E42C-S75C-N79C-K107C-E136C) | 1.17 ± 0.07 |
| 2-6 diSialo (Q45C-S75C-N79C-K107C-E136C) | 0.88 ± 0.15 |
| 2-6 diSialo (L46C-S75C-N79C-K107C-E136C) | 1.26 ± 0.14 |
| 2-6 diSialo (Q47C-S75C-N79C-K107C-E136C) | 0.98 ± 0.09 |
| 2-6 diSialo (Q48C-S75C-N79C-K107C-E136C) | 3.05 ± 0.31 |
| 2-6 diSialo (F49C-S75C-N79C-K107C-E136C) | 1.04 ± 0.12 |
| 2-6 diSialo (Q50C-S75C-N79C-K107C-E136C) | 1.12 ± 0.08 |
| 2-6 monoSialo (S1C-Q48C-N79C-K107C) | 1.75 ± 0.46 |
| 2-6 diSialo (S1C-Q48C-N79C-K107C) | 1.07 ± 0.43 |
| 2-3 diSialo (S1C-Q48C-N79C-K107C) | 1.45 ± 0.58 |
| 2-6 diSiala (S1C-N3C-Q48C-N79C) | 1.96 ± 0.63 |
| 2-6 diSalo (N79C-K107C-R112C-E136C) | 2.89 ± 0.84 |
| 2-6 diSialo (S1C-N79C-K107C-E136C) | 1.52 ± 0.65 |
| 2-6 diSialo (E28C-N79C-K107C-E136C) | 1.93 ± 0.77 |
| 2-6 diSialo (M35C-N79C-K107C-E136C) | 2.19 ± 0.82 |
| 2-6 diSialo (R70C-N79C-K107C-E136C) | 1.44 ± 0.46 |
| 2-6 diSialo (S75C-N79C-K107C-E136C) | 2.11 ± 0.67 |
| 2-6 triSialo (S1C-Q48C-N79C-K107C) | 2.01 ± 0.57 |
| 2-6 tetraSialo (S1C-Q48C-N79C-K107C) | 2.17 ± 0.85 |

As shown in (Table 4), improvement in cell growth inhibitory activity in vitro was also seen with various glycosylated polypeptides that were glycosylated at a position different from glycosylated IFN-β in which an effect of improvement in antitumor activity was seen herein. In regards to the glycosylated polypeptides shown in (Table 4), similarly to the aforementioned glycosylation polypeptides, it is thought that the glycosylated polypeptide of the present invention wherein all of the non-reducing terminals are sialylated can also be used as a pharmaceutical having interferon β activity and as a pharmaceutical superior in interferon activity such as antitumor activity.

From the above, the quadruple-sextuple-glycosylated IFN-β of the present invention was shown to have a higher retentivity in blood and a higher antitumor activity than natural IFN-β (AVONEX®).

As shown in FIGS. 4, 5, and 12, it was shown that disialo glycosylated IFN-β will have a higher retentivity in blood as well as higher antitumor activity as the number of sugar chains increased from quadruple to quintuple, quintuple to sextuple, etc.

Moreover, in the present invention, it was shown that all of the non-reducing terminals of the sugar chain being sialylated is important for improvement of retentivity of IFN-β in blood and improvement of antitumor activity in vivo.

Moreover, in all the cases of employing various sugar chains such as disialo sugar chains as well as trisialo sugar chains and tetrasialo sugar chains as a sugar chain having all of the non-reducing terminals of the sugar chain sialylated, it was shown to have a higher retentivity in blood and a higher antitumor activity than natural IFN-β (AVONEX®).

Accordingly, the glycosylated polypeptide of the present invention is thought to be useful as a pharmaceutical having superior interferon β activity.

The invention claimed is:

1. A glycosylated polypeptide having interferon β activity, wherein said glycosylated polypeptide is any polypeptide selected from the group consisting of the following (1) to (3):
   (1) a polypeptide consisting of the amino acid sequence of SEQ ID NO:1;
   (2) a polypeptide having one to ten amino acids deleted, substituted, or added in the polypeptide consisting of the amino acid sequence of SEQ ID NO:1; and
   (3) a polypeptide having 90% or more identity to the amino acid sequence of SEQ ID NO:1,
   wherein amino acids at 4 to 6 locations in the polypeptides of (1) to (3) are substituted with glycosylated Asn and/or Cys, wherein said glycosylated Asn or Cys are present at a position selected from the group consisting of positions 1, 3, 41, 48, 75, 79, 107, 112, 123, and 136, and any combination thereof, in the amino acid sequence of SEQ ID NO:1, and all of the non-reducing terminals of sugar chains in said glycosylated amino acids are sialylated.

2. A glycosylated polypeptide according to claim 1, wherein the sugar chains in said respective glycosylated amino acids are each independently selected from the group consisting of a disialo sugar chain, a trisialo sugar chain, and a tetrasialo sugar chain.

3. A glycosylated polypeptide according to claim 1, wherein the sugar chains in said respective glycosylated amino acids are each independently selected from the group consisting of the following Formula (1), Formula (2), Formula (3), and Formula (4).

[Chemical Formula 1]

Formula (1)

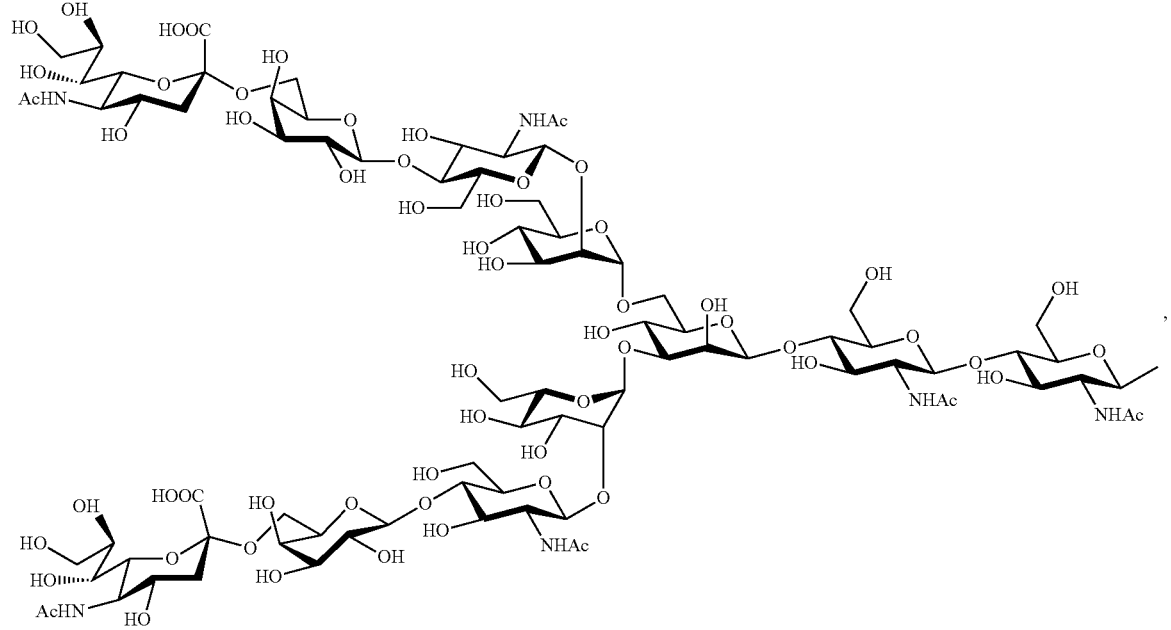

[Chemical Formula 2]
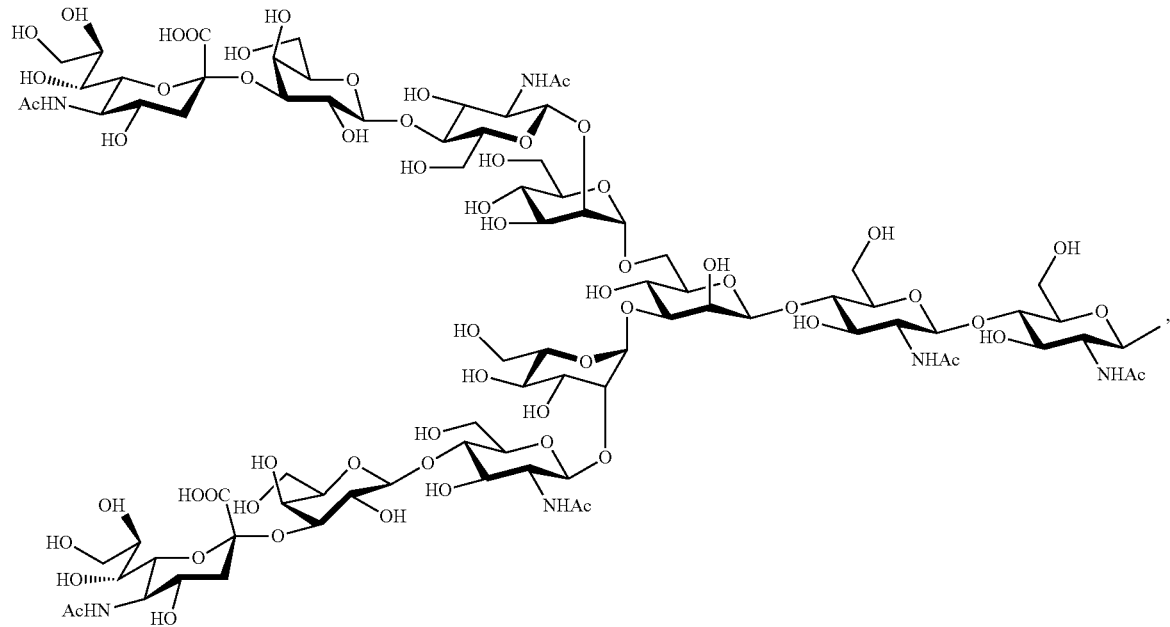
Formula (2)
[Chemical Formula 3]
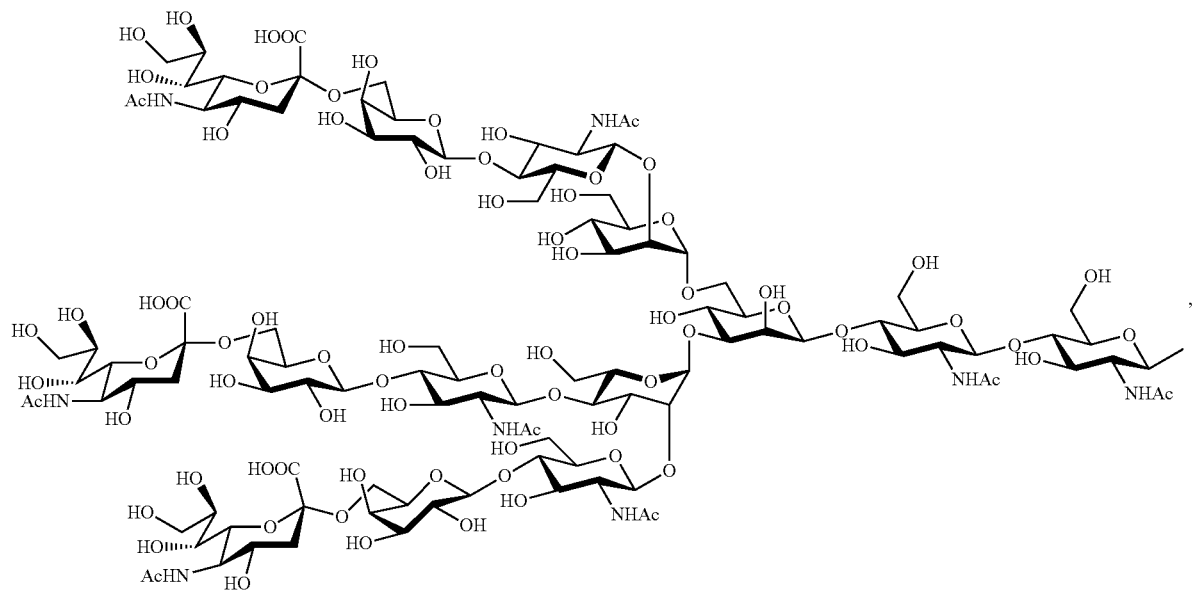
Formula (3)

[Chemical Formula 4]

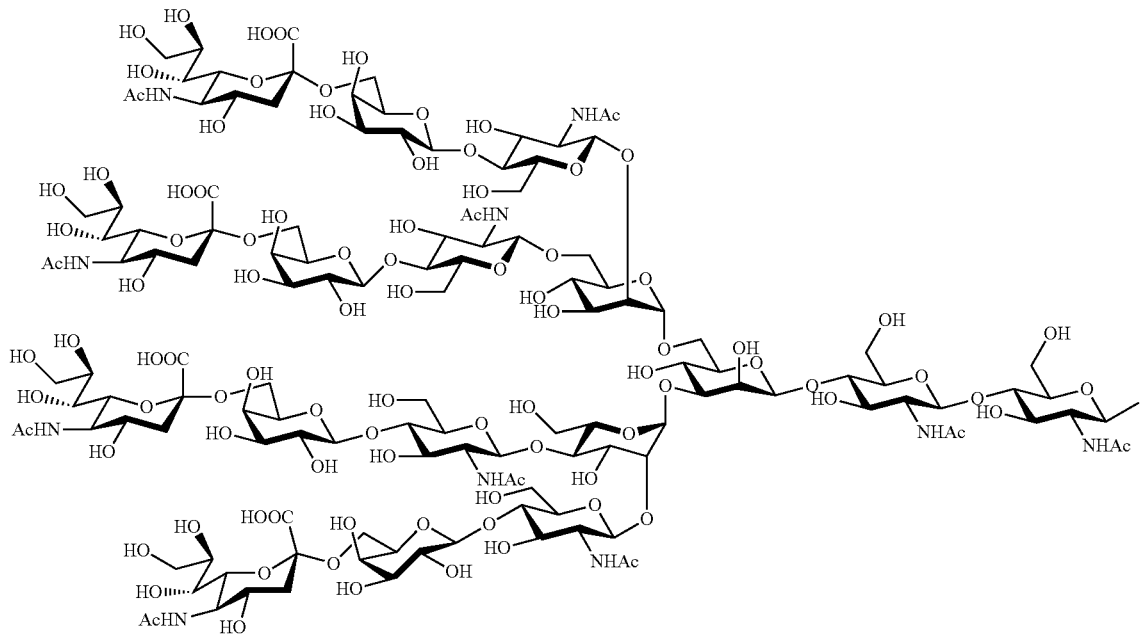

Formula (4)

4. A glycosylated polypeptide according to claim 1, wherein the sugar chains in said respective glycosylated amino acids are all identical in respect to the type of sugar configuring the sugar chain, the binding order, and the binding mode.

5. A glycosylated polypeptide according to claim 1, wherein said glycosylated polypeptide is chemically synthesized.

6. A pharmaceutical composition comprising:

(1) a glycosylated polypeptide according to claim 1 and/or a pharmaceutically acceptable salt thereof, and (2) a pharmaceutically acceptable carrier.

* * * * *

UNITED STATES PATENT AND TRADEMARK OFFICE
CERTIFICATE OF CORRECTION

PATENT NO.       : 10,053,499 B2
APPLICATION NO.  : 14/780133
DATED            : August 21, 2018
INVENTOR(S)      : Ohuchi et al.

It is certified that error appears in the above-identified patent and that said Letters Patent is hereby corrected as shown below:

On the Title Page

Item (56) References Cited, Other Publications, Haselberg et al. cite:
Please correct "noricovalently" to read -- noncovalently --

Item (56) References Cited, Other Publications, Revel cite:
Please correct "*Cyokines*" to read -- *Cytokines* --

Item (56) References Cited, Other Publications, Ruzicka et al. cite:
Please correct "far" to read -- for --

In the Specification

Column 2, Line 22:
Please correct "7,416,173" to read -- 7,446,173 --

Column 7, Line 12:
Please correct "161" to read -- 164 --

Column 9, Lines 8-9:
Please correct "2-6 diSialo(S1C-N3C-Q48C-N79C-K107C-R112C)" to read
-- 2-6 diSialo(S1C- Q48C-N79C-K107C-R112C) --

Column 9, Lines 16-18:1
Please replace:
"and 2-6 monoSialo(S1C-N3C-Q48C-N79C-K107C-R112C),
2-6 diSialo(S1C-Q48C-N79C-K107C-R112C-R123C)."
With:
-- and 2-6 monoSialo(S1C-Q48C-N79C-K107C-R112C-R123C). --

Signed and Sealed this
Fifth Day of February, 2019

Andrei Iancu
*Director of the United States Patent and Trademark Office*

CERTIFICATE OF CORRECTION (continued)
U.S. Pat. No. 10,053,499 B2

Column 15, Chemical Formula 10:
Please replace:

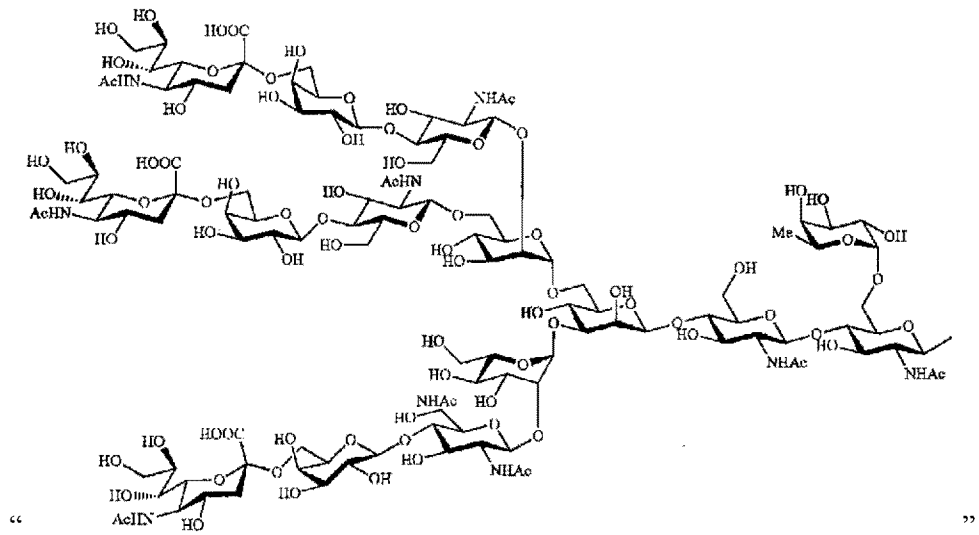

"                                                                                                    "

With:

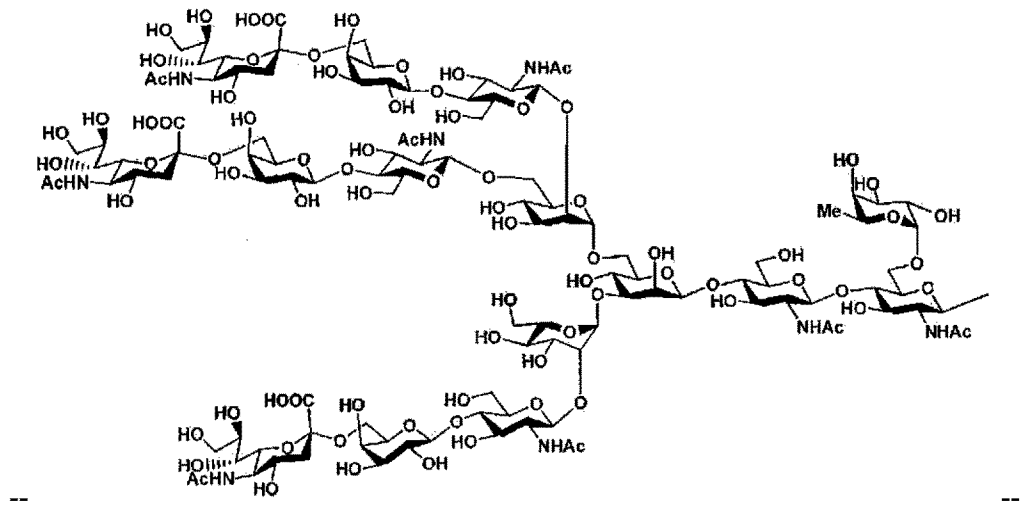

-- --

Column 22, Line 6:
Please correct "75,79,99," to read -- 75,99, --

Column 23, Line 40:
Please correct "70,79,117, and 136;" to read -- 70,79,107, and 136; --

Column 24, Line 24:
Please correct "about 2," to read -- about 1, 2, --

Column 28, Line 53:
Please correct "1-yl)" to read -- 1-yl --

Column 34, Line 30:
Please correct "(S1Thi-C30Acm-Q48C)" to read -- (S1Thi-C30Acm-M35C-Q48C) --
Column 39, Chemical Formula 18:
Please replace:
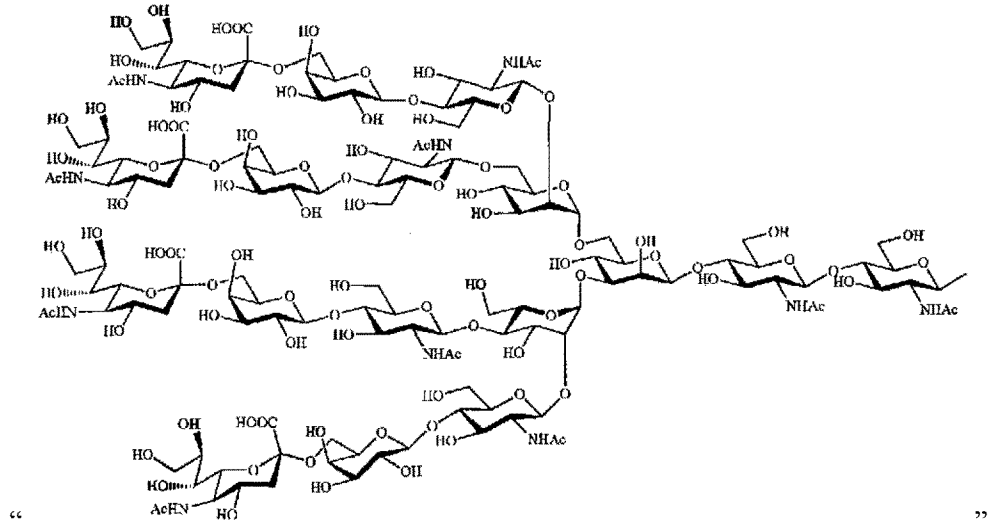
"                                                                                         "
With:
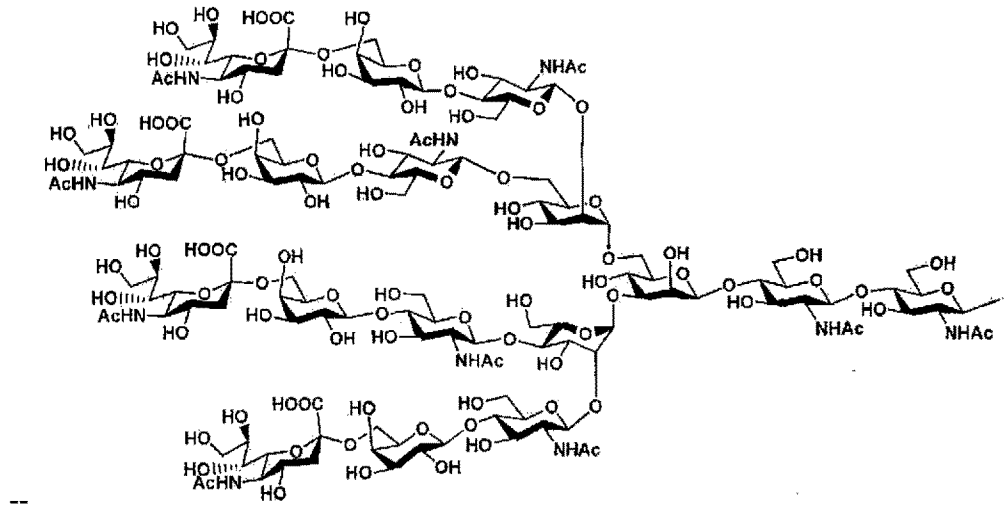
--                                                                                         --
Column 43, Line 23:
Please correct "SEQ ID NO. 3)" to read -- (SEQ ID NO. 3) --
Column 43, Line 31:
Please correct "(125 ml)" to read -- (1.25 ml) --
Column 53, Lines 36-37:
Please correct "2-6 diSialo(E41C-S75C-N79C-K107C-E136C) (SEQ ID NO. 79)" to read
-- 2-3 diSialo(S1C-Q48C-N79C-K107C) (SEQ ID NO. 92) --

CERTIFICATE OF CORRECTION (continued)
U.S. Pat. No. 10,053,499 B2

Column 53, Line 56:
Please correct "(125 ml)" to read -- (1.25 ml) --

Column 64, Line 2:
Please correct "NO. 4-1" to read -- NO. 94 --

Column 64, Line 9:
Please correct "IFN-62" to read -- IFN-β --

Column 69, Line 3:
Please correct "6 nM" to read -- 6 mM --

In the Claims

Column 221, Claim 1, Line 25:
Please correct "front" to read -- from --

SEQUENCE LISTING

```
<160> NUMBER OF SEQ ID NOS: 111

<210> SEQ ID NO 1
<211> LENGTH: 165
<212> TYPE: PRT
<213> ORGANISM: Artificial Sequence
<220> FEATURE:
<223> OTHER INFORMATION: expressed in Escherichia coli
<220> FEATURE:
<221> NAME/KEY: DISULFID
<222> LOCATION: (30)..(140)

<400> SEQUENCE: 1

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Asn Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Lys Glu Asp Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 2
<211> LENGTH: 166
<212> TYPE: PRT
<213> ORGANISM: Homo sapiens

<400> SEQUENCE: 2

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
```

```
                 35                  40                  45

Gln Phe Gln Lys Glu Asp Ala Ala Leu Thr Ile Tyr Glu Met Leu Gln
             50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Asp Phe Thr
             100                 105                 110

Arg Gly Lys Leu Met Ser Ser Leu His Leu Lys Arg Tyr Tyr Gly Arg
                115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 3
<211> LENGTH: 78
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 1C has Thiazolidine gourp
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with Ethanthiol

<400> SEQUENCE: 3

Cys Tyr Asn Leu Leu Gly Phe Leu Gln Arg Ser Ser Asn Phe Gln Ser
 1               5                  10                  15

Gln Lys Leu Leu Trp Gln Leu Asn Gly Arg Leu Glu Tyr Cys Leu Lys
                20                  25                  30

Asp Arg Met Asn Phe Asp Ile Pro Glu Glu Ile Lys Gln Leu Gln Cys
             35                  40                  45

Phe Gln Lys Glu Asp Ala Ala Leu Thr Ile Tyr Glu Met Leu Gln Asn
         50                  55                  60

Ile Phe Ala Ile Phe Arg Gln Asp Ser Ser Ser Thr Gly Trp
 65                  70                  75

<210> SEQ ID NO 4
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 1C has Thiazolidine gourp
<220> FEATURE:
<221> NAME/KEY: BINDING
<222> LOCATION: (30)..(30)
<223> OTHER INFORMATION: Acm
<220> FEATURE:
```

<221> NAME/KEY: BINDING
<222> LOCATION: (78)..(78)
<223> OTHER INFORMATION: alkylthioester-modified with MESNA

<400> SEQUENCE: 4

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Cys Thr Gly Trp
65                  70                  75

<210> SEQ ID NO 5
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 1C has Thiazolidine gourp
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with Ethanthiol

<400> SEQUENCE: 5

Cys Tyr Cys Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp
65                  70                  75

<210> SEQ ID NO 6
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 1C has Thiazolidine gourp
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with Ethanthiol

<400> SEQUENCE: 6

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Cys Tyr Cys Leu Lys
            20                  25                  30

Asp Arg Met Asn Phe Asp Ile Pro Glu Glu Ile Lys Gln Leu Gln Cys
            35                  40                  45

Phe Gln Lys Glu Asp Ala Ala Leu Thr Ile Tyr Glu Met Leu Gln Asn
        50                  55                  60

Ile Phe Ala Ile Phe Cys Gln Asp Ser Ser Ser Thr Gly Trp
65                  70                  75

<210> SEQ ID NO 7
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 7

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Gln
            35                  40                  45

Phe Gln Lys Glu Asp Ala Ala Leu Thr Ile Tyr Glu Met Leu Gln Asn
        50                  55                  60

Ile Phe Ala Ile Phe Arg Gln Asp Ser Ser Ser Thr Gly Trp
65                  70                  75

<210> SEQ ID NO 8
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 1C has Thiazolidine gourp
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 8

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Gln
            35                  40                  45

```
Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp
65                  70                  75

<210> SEQ ID NO 9
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 9

Ser Tyr Asn Leu Leu Gly Cys Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp
65                  70                  75

<210> SEQ ID NO 10
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 10

Ser Tyr Asn Leu Leu Gly Phe Leu Gln Arg Ser Ser Asn Phe Gln Ser
1               5                   10                  15

Gln Lys Leu Leu Trp Gln Leu Cys Gly Arg Leu Glu Tyr Cys Leu Lys
            20                  25                  30

Asp Arg Met Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp
65                  70                  75

<210> SEQ ID NO 11
<211> LENGTH: 78
<212> TYPE: PRT
<213> ORGANISM: Artificial sequence
<220> FEATURE:
```

<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 11

Ser Tyr Asn Leu Leu Gly Phe Leu Gln Arg Ser Ser Asn Phe Gln Ser
1               5                   10                  15

Gln Lys Leu Leu Trp Gln Leu Asn Cys Arg Leu Glu Tyr Cys Leu Lys
            20                  25                  30

Asp Arg Met Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp
65                  70                  75

<210> SEQ ID NO 12
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 12

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Cys Tyr Cys Leu Lys
            20                  25                  30

Asp Arg Met Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp
65                  70                  75

<210> SEQ ID NO 13
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 13

Ser Tyr Asn Leu Leu Gly Phe Leu Gln Arg Ser Ser Asn Phe Gln Ser

```
                1               5                    10                   15
            Gln Lys Leu Leu Trp Gln Leu Asn Gly Arg Leu Glu Tyr Cys Leu Cys
                        20                  25                  30

Asp Arg Met Asn Phe Asp Ile Pro Glu Glu Ile Lys Gln Leu Gln Gln
                        35                  40                  45

Phe Gln Lys Glu Asp Ala Ala Leu Thr Ile Tyr Glu Met Leu Gln Asn
                        50                  55                  60

Ile Phe Ala Ile Phe Arg Gln Asp Ser Ser Thr Gly Trp
            65                  70                  75

<210> SEQ ID NO 14
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 14

Ser Tyr Asn Leu Leu Gly Phe Leu Gln Arg Ser Ser Asn Phe Gln Ser
            1               5                   10                  15

Gln Lys Leu Leu Trp Gln Leu Asn Gly Arg Leu Glu Tyr Cys Leu Lys
                        20                  25                  30

Asp Arg Cys Asn Phe Asp Ile Pro Glu Glu Ile Lys Gln Leu Gln Gln
                        35                  40                  45

Phe Gln Lys Glu Asp Ala Ala Leu Thr Ile Tyr Glu Met Leu Gln Asn
                        50                  55                  60

Ile Phe Ala Ile Phe Arg Gln Asp Ser Ser Thr Gly Trp
            65                  70                  75

<210> SEQ ID NO 15
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 15

Ser Tyr Asn Leu Leu Gly Phe Leu Gln Arg Ser Ser Asn Phe Gln Ser
            1               5                   10                  15

Gln Lys Leu Leu Trp Gln Leu Asn Gly Arg Leu Glu Tyr Cys Leu Lys
                        20                  25                  30

Asp Arg Met Asn Phe Cys Ile Pro Glu Glu Ile Lys Gln Leu Gln Gln
                        35                  40                  45

Phe Gln Lys Glu Asp Ala Ala Leu Thr Ile Tyr Glu Met Leu Gln Asn
                        50                  55                  60

Ile Phe Ala Ile Phe Arg Gln Asp Ser Ser Thr Gly Trp
            65                  70                  75
```

```
<210> SEQ ID NO 16
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 16

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Cys Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp
65                  70                  75

<210> SEQ ID NO 17
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 17

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp
65                  70                  75

<210> SEQ ID NO 18
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
```

```
<221> NAME/KEY: BINDING
<222> LOCATION: (78)..(78)
<223> OTHER INFORMATION: alkylthioester-modified with MESNA

<400> SEQUENCE: 18

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Cys Gln Asp Ser Ser Ser Thr Gly Trp
65                  70                  75

<210> SEQ ID NO 19
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 19

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Cys Thr Gly Trp
65                  70                  75

<210> SEQ ID NO 20
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 20

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Cys Glu Ile Lys Gln Leu Gln Gln
```

```
                    35                  40                  45

Phe Gln Lys Glu Asp Ala Ala Leu Thr Ile Tyr Glu Met Leu Gln Asn
         50                  55                  60

Ile Phe Ala Ile Phe Arg Gln Asp Ser Ser Cys Thr Gly Trp
 65                  70                  75
```

<210> SEQ ID NO 21
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 21

```
Ser Tyr Asn Leu Leu Gly Phe Leu Gln Arg Ser Ser Asn Phe Gln Ser
  1               5                  10                  15

Gln Lys Leu Leu Trp Gln Leu Asn Gly Arg Leu Glu Tyr Cys Leu Lys
                 20                  25                  30

Asp Arg Met Asn Phe Asp Ile Pro Glu Cys Ile Lys Gln Leu Gln Gln
             35                  40                  45

Phe Gln Lys Glu Asp Ala Ala Leu Thr Ile Tyr Glu Met Leu Gln Asn
         50                  55                  60

Ile Phe Ala Ile Phe Arg Gln Asp Ser Ser Cys Thr Gly Trp
 65                  70                  75
```

<210> SEQ ID NO 22
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 22

```
Ser Tyr Asn Leu Leu Gly Phe Leu Gln Arg Ser Ser Asn Phe Gln Ser
  1               5                  10                  15

Gln Lys Leu Leu Trp Gln Leu Asn Gly Arg Leu Glu Tyr Cys Leu Lys
                 20                  25                  30

Asp Arg Met Asn Phe Asp Ile Pro Glu Glu Ile Lys Cys Leu Gln Gln
             35                  40                  45

Phe Gln Lys Glu Asp Ala Ala Leu Thr Ile Tyr Glu Met Leu Gln Asn
         50                  55                  60

Ile Phe Ala Ile Phe Arg Gln Asp Ser Ser Cys Thr Gly Trp
 65                  70                  75
```

<210> SEQ ID NO 23
<211> LENGTH: 78
<212> TYPE: PRT
<213> ORGANISM: Artificial sequence

```
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 23

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Cys Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Cys Thr Gly Trp
65                  70                  75

<210> SEQ ID NO 24
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 24

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Cys Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Cys Thr Gly Trp
65                  70                  75

<210> SEQ ID NO 25
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 25
```

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Cys Thr Gly Trp
65                  70                  75

<210> SEQ ID NO 26
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 26

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Gln
        35                  40                  45

Cys Gln Lys Glu Asp Ala Ala Leu Thr Ile Tyr Glu Met Leu Gln Asn
    50                  55                  60

Ile Phe Ala Ile Phe Arg Gln Asp Ser Ser Cys Thr Gly Trp
65                  70                  75

<210> SEQ ID NO 27
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 27

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Gln
        35                  40                  45

Phe Cys Lys Glu Asp Ala Ala Leu Thr Ile Tyr Glu Met Leu Gln Asn
    50                  55                  60

Ile Phe Ala Ile Phe Arg Gln Asp Ser Ser Cys Thr Gly Trp 65                  70                  75

<210> SEQ ID NO 28
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 1C has Thiazolidine gourp
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 28

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Cys Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp
65                  70                  75

<210> SEQ ID NO 29
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 1C has Thiazolidine gourp
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 29

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Cys Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp
65                  70                  75

<210> SEQ ID NO 30
<211> LENGTH: 78

```
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 1C has Thiazolidine gourp
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (78)..(78)
<223> OTHER INFORMATION: alkylthioester-modified with MESNA

<400> SEQUENCE: 30

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Cys Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp
65                  70                  75

<210> SEQ ID NO 31
<211> LENGTH: 87
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (62)..(62)
<223> OTHER INFORMATION: Acm

<400> SEQUENCE: 31

Cys Glu Thr Ile Val Glu Asn Leu Leu Ala Asn Val Tyr His Gln Ile
1               5                   10                  15

Asn His Leu Lys Thr Val Leu Glu Glu Lys Leu Glu Cys Glu Asp Phe
            20                  25                  30

Thr Cys Gly Lys Leu Met Ser Ser Leu His Leu Lys Cys Tyr Tyr Gly
        35                  40                  45

Arg Ile Leu His Tyr Leu Lys Ala Lys Glu Tyr Ser His Cys Ala Trp
    50                  55                  60

Thr Ile Val Arg Val Glu Ile Leu Arg Asn Phe Tyr Phe Ile Asn Arg
65                  70                  75                  80

Leu Thr Gly Tyr Leu Arg Asn
                85

<210> SEQ ID NO 32
<211> LENGTH: 87
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (62)..(62)
<223> OTHER INFORMATION: Acm

<400> SEQUENCE: 32
```

-continued

Cys Glu Thr Ile Val Glu Asn Leu Leu Ala Asn Val Tyr His Gln Ile
1               5                   10                  15

Asn His Leu Lys Thr Val Leu Glu Glu Lys Leu Glu Lys Glu Asp Phe
                20                  25                  30

Thr Arg Gly Lys Leu Met Ser Ser Leu His Leu Lys Arg Tyr Tyr Gly
            35                  40                  45

Arg Ile Leu His Tyr Leu Lys Ala Lys Glu Tyr Ser His Cys Ala Trp
        50                  55                  60

Thr Ile Val Arg Val Glu Ile Leu Arg Asn Phe Tyr Phe Ile Asn Arg
65                  70                  75                  80

Leu Thr Gly Tyr Leu Arg Asn
                85

<210> SEQ ID NO 33
<211> LENGTH: 87
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (62)..(62)
<223> OTHER INFORMATION: Acm

<400> SEQUENCE: 33

Cys Glu Thr Ile Val Glu Asn Leu Leu Ala Asn Val Tyr His Gln Ile
1               5                   10                  15

Asn His Leu Lys Thr Val Leu Glu Glu Lys Leu Glu Cys Glu Asp Phe
                20                  25                  30

Thr Arg Gly Lys Leu Met Ser Ser Leu His Leu Lys Arg Tyr Tyr Gly
            35                  40                  45

Arg Ile Leu His Tyr Leu Lys Ala Lys Glu Tyr Ser His Cys Ala Trp
        50                  55                  60

Thr Ile Val Arg Val Glu Ile Leu Arg Asn Phe Tyr Phe Ile Asn Arg
65                  70                  75                  80

Leu Thr Gly Tyr Leu Arg Asn
                85

<210> SEQ ID NO 34
<211> LENGTH: 87
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (62)..(62)
<223> OTHER INFORMATION: Acm

<400> SEQUENCE: 34

Cys Glu Thr Ile Val Glu Asn Leu Leu Ala Asn Val Tyr His Gln Ile
1               5                   10                  15

Asn His Leu Lys Thr Val Leu Glu Glu Lys Leu Glu Cys Glu Asp Phe
                20                  25                  30

Thr Cys Gly Lys Leu Met Ser Ser Leu His Leu Lys Arg Tyr Tyr Gly
            35                  40                  45

Arg Ile Leu His Tyr Leu Lys Ala Lys Glu Tyr Ser His Cys Ala Trp
        50                  55                  60

Thr Ile Val Arg Val Glu Ile Leu Arg Asn Phe Tyr Phe Ile Asn Arg
65                  70                  75                  80

Leu Thr Gly Tyr Leu Arg Asn
                85

<210> SEQ ID NO 35
<211> LENGTH: 87
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (62)..(62)
<223> OTHER INFORMATION: Acm

<400> SEQUENCE: 35

Cys Glu Thr Ile Val Glu Asn Leu Leu Ala Asn Val Tyr His Gln Ile
1               5                   10                  15

Asn His Leu Lys Thr Val Leu Glu Glu Lys Leu Glu Cys Glu Asp Phe
            20                  25                  30

Thr Arg Gly Lys Leu Met Ser Ser Leu His Leu Lys Arg Tyr Tyr Gly
        35                  40                  45

Arg Ile Leu His Tyr Leu Lys Ala Lys Cys Tyr Ser His Cys Ala Trp
    50                  55                  60

Thr Ile Val Arg Val Glu Ile Leu Arg Asn Phe Tyr Phe Ile Asn Arg
65                  70                  75                  80

Leu Thr Gly Tyr Leu Arg Asn
                85

<210> SEQ ID NO 36
<211> LENGTH: 87
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (62)..(62)
<223> OTHER INFORMATION: Acm

<400> SEQUENCE: 36

Cys Glu Thr Ile Val Glu Asn Leu Leu Ala Asn Val Tyr His Gln Ile
1               5                   10                  15

Asn His Leu Lys Cys Val Leu Glu Glu Lys Leu Glu Cys Glu Asp Phe
            20                  25                  30

Thr Cys Gly Lys Leu Met Ser Ser Leu His Leu Lys Arg Tyr Tyr Gly
        35                  40                  45

Arg Ile Leu His Tyr Leu Lys Ala Lys Glu Tyr Ser His Cys Ala Trp
    50                  55                  60

Thr Ile Val Arg Val Glu Ile Leu Arg Asn Phe Tyr Phe Ile Asn Arg
65                  70                  75                  80

Leu Thr Gly Tyr Leu Arg Asn
                85

<210> SEQ ID NO 37
<211> LENGTH: 87
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (62)..(62)
<223> OTHER INFORMATION: Acm

<400> SEQUENCE: 37

Cys Glu Thr Ile Val Glu Asn Leu Leu Ala Asn Val Tyr His Gln Ile
1               5                   10                  15

Asn His Leu Lys Thr Val Leu Glu Cys Lys Leu Glu Cys Glu Asp Phe
            20                  25                  30

Thr Arg Gly Lys Leu Met Ser Ser Leu His Leu Lys Arg Tyr Tyr Gly
        35                  40                  45

Arg Ile Leu His Tyr Leu Lys Ala Lys Cys Tyr Ser His Cys Ala Trp
    50                  55                  60

Thr Ile Val Arg Val Glu Ile Leu Arg Asn Phe Tyr Phe Ile Asn Arg
65                  70                  75                  80

Leu Thr Gly Tyr Leu Arg Asn
                85

<210> SEQ ID NO 38
<211> LENGTH: 87
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (62)..(62)
<223> OTHER INFORMATION: Acm

<400> SEQUENCE: 38

Cys Glu Thr Ile Val Glu Asn Leu Leu Ala Asn Val Tyr His Gln Ile
1               5                   10                  15

Asn His Leu Lys Thr Val Leu Glu Glu Lys Leu Cys Cys Glu Asp Phe
            20                  25                  30

Thr Arg Gly Lys Leu Met Ser Ser Leu His Leu Lys Arg Tyr Tyr Gly
        35                  40                  45

Arg Ile Leu His Tyr Leu Lys Ala Lys Cys Tyr Ser His Cys Ala Trp
    50                  55                  60

Thr Ile Val Arg Val Glu Ile Leu Arg Asn Phe Tyr Phe Ile Asn Arg
65                  70                  75                  80

Leu Thr Gly Tyr Leu Arg Asn
                85

<210> SEQ ID NO 39
<211> LENGTH: 87
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (62)..(62)
<223> OTHER INFORMATION: Acm

<400> SEQUENCE: 39

Cys Glu Thr Ile Val Glu Asn Leu Leu Ala Asn Val Tyr His Gln Ile
1               5                   10                  15

Asn His Leu Lys Thr Val Leu Glu Glu Lys Leu Glu Cys Glu Cys Phe
            20                  25                  30

Thr Arg Gly Lys Leu Met Ser Ser Leu His Leu Lys Arg Tyr Tyr Gly
        35                  40                  45

Arg Ile Leu His Tyr Leu Lys Ala Lys Cys Tyr Ser His Cys Ala Trp
    50                  55                  60

Thr Ile Val Arg Val Glu Ile Leu Arg Asn Phe Tyr Phe Ile Asn Arg
65                  70                  75                  80

Leu Thr Gly Tyr Leu Arg Asn
                85

<210> SEQ ID NO 40
<211> LENGTH: 87
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (62)..(62)
<223> OTHER INFORMATION: Acm

<400> SEQUENCE: 40

Cys Glu Thr Ile Val Glu Asn Leu Leu Ala Asn Val Tyr His Gln Ile
1               5                   10                  15

Asn His Leu Lys Thr Val Leu Glu Glu Lys Leu Glu Cys Glu Asp Phe
                20                  25                  30

Thr Arg Gly Lys Cys Met Ser Ser Leu His Leu Lys Arg Tyr Tyr Gly
            35                  40                  45

Arg Ile Leu His Tyr Leu Lys Ala Lys Cys Tyr Ser His Cys Ala Trp
        50                  55                  60

Thr Ile Val Arg Val Glu Ile Leu Arg Asn Phe Tyr Phe Ile Asn Arg
65                  70                  75                  80

Leu Thr Gly Tyr Leu Arg Asn
                85

<210> SEQ ID NO 41
<211> LENGTH: 87
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (62)..(62)
<223> OTHER INFORMATION: Acm

<400> SEQUENCE: 41

Cys Glu Thr Ile Val Glu Asn Leu Leu Ala Asn Val Tyr His Gln Ile
1               5                   10                  15

Asn His Leu Lys Thr Val Leu Glu Glu Lys Leu Glu Cys Glu Asp Phe
                20                  25                  30

Thr Arg Gly Lys Leu Met Ser Ser Cys His Leu Lys Arg Tyr Tyr Gly
            35                  40                  45

Arg Ile Leu His Tyr Leu Lys Ala Lys Cys Tyr Ser His Cys Ala Trp
        50                  55                  60

Thr Ile Val Arg Val Glu Ile Leu Arg Asn Phe Tyr Phe Ile Asn Arg
65                  70                  75                  80

Leu Thr Gly Tyr Leu Arg Asn
                85

<210> SEQ ID NO 42
<211> LENGTH: 87
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (62)..(62)
<223> OTHER INFORMATION: Acm

<400> SEQUENCE: 42

Cys Glu Thr Ile Val Glu Asn Leu Leu Ala Asn Val Tyr His Gln Ile
1               5                   10                  15

Asn His Leu Lys Thr Val Leu Glu Glu Lys Leu Glu Cys Glu Asp Phe
            20                  25                  30

Thr Cys Gly Lys Leu Met Ser Ser Leu His Leu Lys Arg Tyr Tyr Gly
        35                  40                  45

Arg Ile Leu Cys Tyr Leu Lys Ala Lys Glu Tyr Ser His Cys Ala Trp
    50                  55                  60

Thr Ile Val Arg Val Glu Ile Leu Arg Asn Phe Tyr Phe Ile Asn Arg
65                  70                  75                  80

Leu Thr Gly Tyr Leu Arg Asn
                85

<210> SEQ ID NO 43
<211> LENGTH: 87
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (62)..(62)
<223> OTHER INFORMATION: Acm

<400> SEQUENCE: 43

Cys Glu Thr Ile Val Glu Asn Leu Leu Ala Asn Val Tyr His Gln Ile
1               5                   10                  15

Asn His Leu Lys Thr Val Leu Glu Glu Lys Leu Glu Cys Glu Asp Phe
            20                  25                  30

Thr Cys Gly Lys Leu Met Ser Ser Leu His Leu Lys Arg Tyr Tyr Gly
        35                  40                  45

Arg Ile Leu His Tyr Leu Lys Ala Lys Cys Tyr Ser His Cys Ala Trp
    50                  55                  60

Thr Ile Val Arg Val Glu Ile Leu Arg Asn Phe Tyr Phe Ile Asn Arg
65                  70                  75                  80

Leu Thr Gly Tyr Leu Arg Asn
                85

<210> SEQ ID NO 44
<211> LENGTH: 87
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (62)..(62)
<223> OTHER INFORMATION: Acm

<400> SEQUENCE: 44

Cys Glu Thr Ile Val Glu Asn Leu Leu Ala Asn Val Tyr His Gln Ile
1               5                   10                  15

Asn His Leu Lys Thr Val Leu Glu Glu Lys Leu Glu Cys Glu Asp Phe
            20                  25                  30

Thr Cys Gly Lys Leu Met Ser Ser Leu His Leu Lys Arg Tyr Tyr Gly
        35                  40                  45

Arg Ile Leu His Tyr Leu Lys Ala Lys Glu Tyr Ser Cys Cys Ala Trp

```
                50                  55                  60
Thr Ile Val Arg Val Glu Ile Leu Arg Asn Phe Tyr Phe Ile Asn Arg
 65                  70                  75                  80

Leu Thr Gly Tyr Leu Arg Asn
                85

<210> SEQ ID NO 45
<211> LENGTH: 87
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (62)..(62)
<223> OTHER INFORMATION: Acm

<400> SEQUENCE: 45

Cys Glu Thr Ile Val Glu Asn Leu Leu Ala Asn Val Tyr His Gln Ile
  1               5                  10                  15

Asn His Leu Lys Thr Val Leu Glu Glu Lys Leu Glu Cys Glu Asp Phe
                 20                  25                  30

Thr Cys Gly Lys Leu Met Ser Ser Leu His Leu Lys Arg Tyr Tyr Gly
             35                  40                  45

Arg Ile Leu His Tyr Leu Lys Ala Lys Glu Tyr Ser His Cys Ala Trp
         50                  55                  60

Thr Ile Val Arg Val Glu Ile Leu Arg Asn Phe Tyr Phe Ile Asn Arg
 65                  70                  75                  80

Leu Thr Gly Tyr Leu Cys Asn
                85

<210> SEQ ID NO 46
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide
<220> FEATURE:
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: CARBOHYD
<222> LOCATION: (123)..(123)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 46

Cys Tyr Asn Leu Leu Gly Phe Leu Gln Arg Ser Ser Asn Phe Gln Ser
  1               5                  10                  15
```

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
            35                  40                  45

Phe Gln Lys Glu Asp Ala Ala Leu Thr Ile Tyr Glu Met Leu Gln Asn
 50                  55                  60

Ile Phe Ala Ile Phe Arg Gln Asp Ser Ser Thr Gly Trp Cys Glu
 65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
            100                 105                 110

Gly Lys Leu Met Ser Ser Leu His Leu Lys Cys Tyr Tyr Gly Arg Ile
            115                 120                 125

Leu His Tyr Leu Lys Ala Lys Glu Tyr Ser His Cys Ala Trp Thr Ile
            130                 135                 140

Val Arg Val Glu Ile Leu Arg Asn Phe Tyr Phe Ile Asn Arg Leu Thr
145                 150                 155                 160

Gly Tyr Leu Arg Asn
            165

<210> SEQ ID NO 47
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (75)..(75)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 47

Ser Tyr Asn Leu Leu Gly Phe Leu Gln Arg Ser Ser Asn Phe Gln Ser
 1               5                  10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
            35                  40                  45

Phe Gln Lys Glu Asp Ala Ala Leu Thr Ile Tyr Glu Met Leu Gln Asn
 50                  55                  60

Ile Phe Ala Ile Phe Arg Gln Asp Ser Ser Cys Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
            100                 105                 110

Gly Lys Leu Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 48
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-3) oligosaccharide
<220> FEATURE:
<221> NAME/KEY: CARBOHYD
<222> LOCATION: (3)..(3)
<223> OTHER INFORMATION: disialo(alpha 2-3) oligosaccharide
<220> FEATURE:
<221> NAME/KEY: CARBOHYD
<222> LOCATION: (48)..(48)
<223> OTHER INFORMATION: disialo(alpha 2-3) oligosaccharide
<220> FEATURE:
<221> NAME/KEY: CARBOHYD
<222> LOCATION: (79)..(79)
<223> OTHER INFORMATION: disialo(alpha 2-3) oligosaccharide
<220> FEATURE:
<221> NAME/KEY: CARBOHYD
<222> LOCATION: (107)..(107)
<223> OTHER INFORMATION: disialo(alpha 2-3) oligosaccharide
<220> FEATURE:
<221> NAME/KEY: CARBOHYD
<222> LOCATION: (112)..(112)
<223> OTHER INFORMATION: disialo(alpha 2-3) oligosaccharide
<220> FEATURE:
<221> NAME/KEY: DISULFID
<222> LOCATION: (30)..(140)

<400> SEQUENCE: 48

Cys Tyr Cys Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
            100                 105                 110

Gly Lys Leu Met Ser Ser Leu His Leu Lys Arg Tyr Tyr Gly Arg Ile
        115                 120                 125

Leu His Tyr Leu Lys Ala Lys Glu Tyr Ser His Cys Ala Trp Thr Ile
        130                 135                 140

Val Arg Val Glu Ile Leu Arg Asn Phe Tyr Phe Ile Asn Arg Leu Thr
145                 150                 155                 160

Gly Tyr Leu Arg Asn
            165

<210> SEQ ID NO 49
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide
<220> FEATURE:
<221> NAME/KEY: CARBOHYD
<222> LOCATION: (3)..(3)
<223> OTHER INFORMATION: disialo(alpha 2-6) oligosaccharide
<220> FEATURE:
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 49

Cys Tyr Cys Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
            100                 105                 110

Gly Lys Leu Met Ser Ser Leu His Leu Lys Arg Tyr Tyr Gly Arg Ile
        115                 120                 125

Leu His Tyr Leu Lys Ala Lys Glu Tyr Ser His Cys Ala Trp Thr Ile
        130                 135                 140

Val Arg Val Glu Ile Leu Arg Asn Phe Tyr Phe Ile Asn Arg Leu Thr
145                 150                 155                 160

Gly Tyr Leu Arg Asn
            165

<210> SEQ ID NO 50
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide
<220> FEATURE:
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (99)..(99)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 50

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
50                  55                  60

Ile Phe Ala Ile Phe Arg Gln Asp Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Cys Val Leu Glu Glu Lys Leu Glu Cys Glu Asp Phe Thr Cys
            100                 105                 110

Gly Lys Leu Met Ser Ser Leu His Leu Lys Arg Tyr Tyr Gly Arg Ile
        115                 120                 125

Leu His Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
            165

<210> SEQ ID NO 51
<211> LENGTH: 165
<212> TYPE: PRT
<213> ORGANISM: Artificial sequence

```
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide
<220> FEATURE:
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: CARBOHYD
<222> LOCATION: (130)..(130)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 51

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
            100                 105                 110

Gly Lys Leu Met Ser Ser Leu His Leu Lys Arg Tyr Tyr Gly Arg Ile
        115                 120                 125

Leu Cys Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 52
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide
<220> FEATURE:
<221> NAME/KEY: CARBOHYD
<222> LOCATION: (48)..(48)
```

```
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 52

Cys Tyr Asn Leu Leu Gly Phe Leu Gln Arg Ser Ser Asn Phe Gln Ser
 1               5                  10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
            100                 105                 110

Gly Lys Leu Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 53
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide
<220> FEATURE:
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
```

```
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: CARBOHYD
<222> LOCATION: (139)..(139)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 53

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
            100                 105                 110

Gly Lys Leu Met Ser Ser Leu His Leu Lys Arg Tyr Tyr Gly Arg Ile
            115                 120                 125

Leu His Tyr Leu Lys Ala Lys Glu Tyr Ser Cys Cys Ala Trp Thr Ile
        130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 54
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide
<220> FEATURE:
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: CARBOHYD
<222> LOCATION: (164)..(164)
<223> OTHER INFORMATION: disialo(alpha 2-6) oligosaccharide
<220> FEATURE:
```

<221> NAME/KEY: DISULFID
<222> LOCATION: (30)..(140)

<400> SEQUENCE: 54

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
            100                 105                 110

Gly Lys Leu Met Ser Ser Leu His Leu Lys Arg Tyr Tyr Gly Arg Ile
        115                 120                 125

Leu His Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Cys Asn
                165

<210> SEQ ID NO 55
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide
<220> FEATURE:
<221> NAME/KEY: CARBOHYD
<222> LOCATION: (29)..(29)
<223> OTHER INFORMATION: disialo(alpha 2-6) oligosaccharide
<220> FEATURE:
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 55

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Cys Cys Leu Lys

```
            20                  25                  30
Asp Arg Met Asn Phe Asp Ile Pro Glu Glu Ile Lys Gln Leu Gln Cys
            35                  40                  45

Phe Gln Lys Glu Asp Ala Ala Leu Thr Ile Tyr Glu Met Leu Gln Asn
        50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Arg
            100                 105                 110

Gly Lys Leu Met Ser Ser Leu His Leu Lys Arg Tyr Tyr Gly Arg Ile
            115                 120                 125

Leu His Tyr Leu Lys Ala Lys Cys Tyr Ser His Cys Ala Trp Thr Ile
        130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 56
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide
<220> FEATURE:
<221> NAME/KEY: CARBOHYD
<222> LOCATION: (35)..(35)
<223> OTHER INFORMATION: disialo(alpha 2-6) oligosaccharide
<220> FEATURE:
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 56

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Cys Asn Phe Asp Ile Pro Glu Glu Ile Lys Gln Leu Gln Cys
            35                  40                  45

Phe Gln Lys Glu Asp Ala Ala Leu Thr Ile Tyr Glu Met Leu Gln Asn
        50                  55                  60

Ile Phe Ala Ile Phe Arg Gln Asp Ser Ser Ser Thr Gly Trp Cys Glu
```

```
                65                  70                  75                  80
Thr Ile Val Glu Asn Leu Leu Ala Asn Val Tyr His Gln Ile Asn His
                    85                  90                  95

Leu Lys Thr Val Leu Glu Glu Lys Leu Glu Cys Glu Asp Phe Thr Arg
                100                 105                 110

Gly Lys Leu Met Ser Ser Leu His Leu Lys Arg Tyr Tyr Gly Arg Ile
                115                 120                 125

Leu His Tyr Leu Lys Ala Lys Cys Tyr Ser His Cys Ala Trp Thr Ile
            130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 57
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide
<220> FEATURE:
<221> NAME/KEY: CARBOHYD
<222> LOCATION: (41)..(41)
<223> OTHER INFORMATION: disialo(alpha 2-6) oligosaccharide
<220> FEATURE:
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 57

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
                20                  25                  30

Asp Arg Met Asn Phe Asp Ile Pro Cys Glu Ile Lys Gln Leu Gln Cys
            35                  40                  45

Phe Gln Lys Glu Asp Ala Ala Leu Thr Ile Tyr Glu Met Leu Gln Asn
        50                  55                  60

Ile Phe Ala Ile Phe Arg Gln Asp Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Arg
                100                 105                 110

Gly Lys Leu Met Ser Ser Leu His Leu Lys Arg Tyr Tyr Gly Arg Ile
```

```
                115                 120                 125
Leu His Tyr Leu Lys Ala Lys Cys Tyr Ser His Cys Ala Trp Thr Ile
        130                 135                 140
Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 58
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide
<220> FEATURE:
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (75)..(75)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 58

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Cys Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165
```

<210> SEQ ID NO 59
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide
<220> FEATURE:
<221> NAME/KEY: CARBOHYD
<222> LOCATION: (28)..(28)
<223> OTHER INFORMATION: disialo(alpha 2-6) oligosaccharide
<220> FEATURE:
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (70)..(70)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 59

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Cys Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Cys Gln Asp Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Lys Glu Asp Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
            165

<210> SEQ ID NO 60
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide

```
<220> FEATURE:
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 60

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
            100                 105                 110

Gly Lys Leu Met Ser Ser Leu His Leu Lys Arg Tyr Tyr Gly Arg Ile
        115                 120                 125

Leu His Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 61
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide
<220> FEATURE:
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
```

<221> NAME/KEY: DISULFID
<222> LOCATION: (30)..(140)

<400> SEQUENCE: 61

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 62
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide
<220> FEATURE:
<221> NAME/KEY: CARBOHYD
<222> LOCATION: (3)..(3)
<223> OTHER INFORMATION: disialo(alpha 2-6) oligosaccharide
<220> FEATURE:
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 62

Cys Tyr Cys Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

```
Ile Phe Ala Ile Phe Arg Gln Asp Ser Ser Thr Gly Trp Cys Glu
 65                  70                  75                  80

Thr Ile Val Glu Asn Leu Leu Ala Asn Val Tyr His Gln Ile Asn His
                 85                  90                  95

Leu Lys Thr Val Leu Glu Glu Lys Leu Glu Lys Glu Asp Phe Thr Arg
            100                 105                 110

Gly Lys Leu Met Ser Ser Leu His Leu Lys Arg Tyr Tyr Gly Arg Ile
            115                 120                 125

Leu His Tyr Leu Lys Ala Lys Glu Tyr Ser His Cys Ala Trp Thr Ile
            130                 135                 140

Val Arg Val Glu Ile Leu Arg Asn Phe Tyr Phe Ile Asn Arg Leu Thr
145                 150                 155                 160

Gly Tyr Leu Arg Asn
            165

<210> SEQ ID NO 63
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 63

Cys Tyr Asn Leu Leu Gly Phe Leu Gln Arg Ser Ser Asn Phe Gln Ser
  1               5                  10                  15

Gln Lys Leu Leu Trp Gln Leu Asn Gly Arg Leu Glu Tyr Cys Leu Lys
             20                  25                  30

Asp Arg Met Asn Phe Asp Ile Pro Glu Glu Ile Lys Gln Leu Gln Gln
             35                  40                  45

Phe Gln Lys Glu Asp Ala Ala Leu Thr Ile Tyr Glu Met Leu Gln Asn
 50                  55                  60

Ile Phe Ala Ile Phe Arg Gln Asp Ser Ser Ser Thr Gly Trp Cys Glu
 65                  70                  75                  80

Thr Ile Val Glu Asn Leu Leu Ala Asn Val Tyr His Gln Ile Asn His
                 85                  90                  95

Leu Lys Thr Val Leu Glu Glu Lys Leu Glu Cys Glu Asp Phe Thr Arg
            100                 105                 110

Gly Lys Leu Met Ser Ser Leu His Leu Lys Arg Tyr Tyr Gly Arg Ile
            115                 120                 125

Leu His Tyr Leu Lys Ala Lys Cys Tyr Ser His Cys Ala Trp Thr Ile
            130                 135                 140

Val Arg Val Glu Ile Leu Arg Asn Phe Tyr Phe Ile Asn Arg Leu Thr
145                 150                 155                 160
```

Gly Tyr Leu Arg Asn
            165

<210> SEQ ID NO 64
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (41)..(41)
<223> OTHER INFORMATION: disialo(alpha 2-6) oligosaccharide
<220> FEATURE:
<221> NAME/KEY: CARBOHYD
<222> LOCATION: (75)..(75)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (103)..(103)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 64

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Cys Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Cys Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Cys Lys Leu Glu Cys Glu Asp Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
            165

<210> SEQ ID NO 65
<211> LENGTH: 165
<212> TYPE: PRT
<213> ORGANISM: Artificial sequence

```
<220> FEATURE:
<223> OTHER INFORMATION: chemically synthesized
<220> FEATURE:
<221> NAME/KEY: CARBOHYD
<222> LOCATION: (41)..(41)
<223> OTHER INFORMATION: disialo(alpha 2-6) oligosaccharide
<220> FEATURE:
<221> NAME/KEY: CARBOHYD
<222> LOCATION: (75)..(75)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (106)..(106)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 65

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Cys Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Cys Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Cys Cys Glu Asp Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 66
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (41)..(41)
<223> OTHER INFORMATION: disialo(alpha 2-6) oligosaccharide
<220> FEATURE:
<221> NAME/KEY: CARBOHYD
<222> LOCATION: (75)..(75)
```

<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (109)..(109)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 66

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Cys Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Cys Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Cys Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 67
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (41)..(41)
<223> OTHER INFORMATION: disialo(alpha 2-6) oligosaccharide
<220> FEATURE:
<221> NAME/KEY: CARBOHYD
<222> LOCATION: (75)..(75)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide

```
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 67

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Cys Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Cys Thr Gly Trp Cys Glu
65              70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
            100                 105                 110

Gly Lys Leu Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 68
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (41)..(41)
<223> OTHER INFORMATION: disialo(alpha 2-6) oligosaccharide
<220> FEATURE:
<221> NAME/KEY: CARBOHYD
<222> LOCATION: (75)..(75)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (115)..(115)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
```

<221> NAME/KEY: DISULFID
<222> LOCATION: (30)..(140)

<400> SEQUENCE: 68

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Cys Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Cys Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Arg
            100                 105                 110

Gly Lys Cys Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 69
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (41)..(41)
<223> OTHER INFORMATION: disialo(alpha 2-6) oligosaccharide
<220> FEATURE:
<221> NAME/KEY: CARBOHYD
<222> LOCATION: (75)..(75)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (119)..(119)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 69

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys

-continued

```
                    20                  25                  30
Asp Arg Met Asn Phe Asp Ile Pro Cys Glu Ile Lys Gln Leu Gln Gln
                35                  40                  45

Phe Gln Lys Glu Asp Ala Ala Leu Thr Ile Tyr Glu Met Leu Gln Asn
 50                  55                  60

Ile Phe Ala Ile Phe Arg Gln Asp Ser Ser Thr Gly Trp Cys Glu
 65                  70                  75                  80

Thr Ile Val Glu Asn Leu Leu Ala Asn Val Tyr His Gln Ile Asn His
                 85                  90                  95

Leu Lys Thr Val Leu Glu Glu Lys Leu Glu Cys Glu Asp Phe Thr Arg
                100                 105                 110

Gly Lys Leu Met Ser Ser Cys His Leu Lys Arg Tyr Tyr Gly Arg Ile
                115                 120                 125

Leu His Tyr Leu Lys Ala Lys Cys Tyr Ser His Cys Ala Trp Thr Ile
                130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 70
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (24)..(24)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 70

Ser Tyr Asn Leu Leu Gly Phe Leu Gln Arg Ser Ser Asn Phe Gln Ser
 1               5                  10                  15

Gln Lys Leu Leu Trp Gln Leu Cys Gly Arg Leu Glu Tyr Cys Leu Lys
                20                  25                  30

Asp Arg Met Asn Phe Asp Ile Pro Glu Glu Ile Lys Gln Leu Gln Gln
                35                  40                  45

Phe Gln Lys Glu Asp Ala Ala Leu Thr Ile Tyr Glu Met Leu Gln Asn
 50                  55                  60

Ile Phe Ala Ile Phe Arg Gln Asp Ser Ser Thr Gly Trp Cys Glu
 65                  70                  75                  80

Thr Ile Val Glu Asn Leu Leu Ala Asn Val Tyr His Gln Ile Asn His
                 85                  90                  95
```

Leu Lys Thr Val Leu Glu Glu Lys Leu Glu Cys Glu Asp Phe Thr Cys
                100                 105                 110

Gly Lys Leu Met Ser Ser Leu His Leu Lys Arg Tyr Tyr Gly Arg Ile
            115                 120                 125

Leu His Tyr Leu Lys Ala Lys Cys Tyr Ser His Cys Ala Trp Thr Ile
        130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 71
<211> LENGTH: 165
<212> TYPE: PRT
<213> ORGANISM: Artificial sequence
<220> FEATURE:
<223> OTHER INFORMATION: chemically synthesized
<221> NAME/KEY: CARBOHYD
<222> LOCATION: (25)..(25)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 71

Ser Tyr Asn Leu Leu Gly Phe Leu Gln Arg Ser Ser Asn Phe Gln Ser
1               5                   10                  15

Gln Lys Leu Leu Trp Gln Leu Asn Cys Arg Leu Glu Tyr Cys Leu Lys
            20                  25                  30

Asp Arg Met Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
                100                 105                 110

Gly Lys Leu Met Ser Ser Leu His Leu Lys Arg Tyr Tyr Gly Arg Ile
            115                 120                 125

Leu His Tyr Leu Lys Ala Lys Cys Tyr Ser His Cys Ala Trp Thr Ile
        130                 135                 140

Val Arg Val Glu Ile Leu Arg Asn Phe Tyr Phe Ile Asn Arg Leu Thr
145                 150                 155                 160

Gly Tyr Leu Arg Asn

<210> SEQ ID NO 72
<211> LENGTH: 165
<212> TYPE: PRT
<213> ORGANISM: Artificial sequence
<220> FEATURE:
<223> OTHER INFORMATION: chemically synthesized
<221> NAME/KEY: CARBOHYD
<222> LOCATION: (32)..(32)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 72

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Cys
            20                  25                  30

Asp Arg Met Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
            100                 105                 110

Gly Lys Leu Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 73
<211> LENGTH: 165
<212> TYPE: PRT
<213> ORGANISM: Artificial sequence
<220> FEATURE:
<223> OTHER INFORMATION: chemically synthesized
<221> NAME/KEY: CARBOHYD
<222> LOCATION: (35)..(35)
<223> OTHER INFORMATION: disialo(alpha 2-6) oligosaccharide
<220> FEATURE:
<221> NAME/KEY: CARBOHYD

```
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 73

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Cys Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
            100                 105                 110

Gly Lys Leu Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 74
<211> LENGTH: 165
<212> TYPE: PRT
<213> ORGANISM: Artificial sequence
<220> FEATURE:
<223> OTHER INFORMATION: chemically synthesized
<221> NAME/KEY: CARBOHYD
<222> LOCATION: (38)..(38)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
```

<220> FEATURE:
<221> NAME/KEY: DISULFID
<222> LOCATION: (30)..(140)

<400> SEQUENCE: 74

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Cys Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
            100                 105                 110

Gly Lys Leu Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 75
<211> LENGTH: 165
<212> TYPE: PRT
<213> ORGANISM: Artificial sequence
<220> FEATURE:
<223> OTHER INFORMATION: chemically synthesized
<221> NAME/KEY: CARBOHYD
<222> LOCATION: (41)..(41)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 75

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Cys Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
                100                 105                 110

Gly Lys Leu Met Ser Ser Leu His Leu Lys Arg Tyr Tyr Gly Arg Ile
            115                 120                 125

Leu His Tyr Leu Lys Ala Lys Cys Tyr Ser His Cys Ala Trp Thr Ile
        130                 135                 140

Val Arg Val Glu Ile Leu Arg Asn Phe Tyr Phe Ile Asn Arg Leu Thr
145                 150                 155                 160

Gly Tyr Leu Arg Asn
            165

<210> SEQ ID NO 76
<211> LENGTH: 165
<212> TYPE: PRT
<213> ORGANISM: Artificial sequence
<220> FEATURE:
<223> OTHER INFORMATION: chemically synthesized
<221> NAME/KEY: CARBOHYD
<222> LOCATION: (7)..(7)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 76

Ser Tyr Asn Leu Leu Gly Cys Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
                100                 105                 110

Gly Lys Leu Met Ser Ser Leu His Leu Lys Arg Tyr Tyr Gly Arg Ile

Leu His Tyr Leu Lys Ala Lys Cys Tyr Ser His Cys Ala Trp Thr Ile
        130                 135                 140

Val Arg Val Glu Ile Leu Arg Asn Phe Tyr Phe Ile Asn Arg Leu Thr
145                 150                 155                 160

Gly Tyr Leu Arg Asn
            165

<210> SEQ ID NO 77
<211> LENGTH: 165
<212> TYPE: PRT
<213> ORGANISM: Artificial sequence
<220> FEATURE:
<223> OTHER INFORMATION: chemically synthesized
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 77

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
            100                 105                 110

Gly Lys Leu Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
            165

<210> SEQ ID NO 78
<211> LENGTH: 165

```
<212> TYPE: PRT
<213> ORGANISM: Artificial sequence
<220> FEATURE:
<223> OTHER INFORMATION: chemically synthesized
<221> NAME/KEY: CARBOHYD
<222> LOCATION: (75)..(75)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 78

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Cys Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
            100                 105                 110

Gly Lys Leu Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 79
<211> LENGTH: 165
<212> TYPE: PRT
<213> ORGANISM: Artificial sequence
<220> FEATURE:
<223> OTHER INFORMATION: chemically synthesized
<221> NAME/KEY: CARBOHYD
<222> LOCATION: (41)..(41)
<223> OTHER INFORMATION: disialo(alpha 2-6) oligosaccharide
<220> FEATURE:
<221> NAME/KEY: CARBOHYD
<222> LOCATION: (75)..(75)
<223> OTHER INFORMATION: disialo(alpha 2-6) oligosaccharide
<220> FEATURE:
<221> NAME/KEY: CARBOHYD
<222> LOCATION: (79)..(79)
```

-continued

<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 79

Ser Tyr Asn Leu Leu Gly Phe Leu Gln Arg Ser Ser Asn Phe Gln Ser
 1               5                  10                  15

Gln Lys Leu Leu Trp Gln Leu Asn Gly Arg Leu Glu Tyr Cys Leu Lys
            20                  25                  30

Asp Arg Met Asn Phe Asp Ile Pro Cys Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Cys Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 80
<211> LENGTH: 165
<212> TYPE: PRT
<213> ORGANISM: Artificial sequence
<220> FEATURE:
<223> OTHER INFORMATION: chemically synthesized
<221> NAME/KEY: CARBOHYD
<222> LOCATION: (42)..(42)
<223> OTHER INFORMATION: disialo(alpha 2-6) oligosaccharide
<220> FEATURE:
<221> NAME/KEY: CARBOHYD
<222> LOCATION: (75)..(75)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 80

```
Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Cys Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Cys Thr Gly Trp Cys Glu
65              70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 81
<211> LENGTH: 165
<212> TYPE: PRT
<213> ORGANISM: Artificial sequence
<220> FEATURE:
<223> OTHER INFORMATION: chemically synthesized
<221> NAME/KEY: CARBOHYD
<222> LOCATION: (45)..(45)
<223> OTHER INFORMATION: disialo(alpha 2-6) oligosaccharide
<220> FEATURE:
<221> NAME/KEY: CARBOHYD
<222> LOCATION: (75)..(75)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 81

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Cys Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Cys Thr Gly Trp Cys Glu
```

```
                65                  70                  75                  80
Thr Ile Val Glu Asn Leu Leu Ala Asn Val Tyr His Gln Ile Asn His
                    85                  90                  95

Leu Lys Thr Val Leu Glu Glu Lys Leu Glu Cys Glu Asp Phe Thr Arg
                    100                 105                 110

Gly Lys Leu Met Ser Ser Leu His Leu Lys Arg Tyr Tyr Gly Arg Ile
                    115                 120                 125

Leu His Tyr Leu Lys Ala Lys Cys Tyr Ser His Cys Ala Trp Thr Ile
                    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 82
<211> LENGTH: 165
<212> TYPE: PRT
<213> ORGANISM: Artificial sequence
<220> FEATURE:
<223> OTHER INFORMATION: chemically synthesized
<221> NAME/KEY: CARBOHYD
<222> LOCATION: (46)..(46)
<223> OTHER INFORMATION: disialo(alpha 2-6) oligosaccharide
<220> FEATURE:
<221> NAME/KEY: CARBOHYD
<222> LOCATION: (75)..(75)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 82

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
                20                  25                  30

Asp Arg Met Asn Phe Asp Ile Pro Glu Glu Ile Lys Gln Cys Gln Gln
                35                  40                  45

Phe Gln Lys Glu Asp Ala Ala Leu Thr Ile Tyr Glu Met Leu Gln Asn
                50                  55                  60

Ile Phe Ala Ile Phe Arg Gln Asp Ser Ser Cys Thr Gly Trp Cys Glu
65                  70                  75                  80

Thr Ile Val Glu Asn Leu Leu Ala Asn Val Tyr His Gln Ile Asn His
                    85                  90                  95

Leu Lys Thr Val Leu Glu Glu Lys Leu Glu Cys Glu Asp Phe Thr Arg
                    100                 105                 110

Gly Lys Leu Met Ser Ser Leu His Leu Lys Arg Tyr Tyr Gly Arg Ile
                    115                 120                 125

Leu His Tyr Leu Lys Ala Lys Cys Tyr Ser His Cys Ala Trp Thr Ile
                    130                 135                 140
```

Val Arg Val Glu Ile Leu Arg Asn Phe Tyr Phe Ile Asn Arg Leu Thr
145                 150                 155                 160

Gly Tyr Leu Arg Asn
            165

<210> SEQ ID NO 83
<211> LENGTH: 165
<212> TYPE: PRT
<213> ORGANISM: Artificial sequence
<220> FEATURE:
<223> OTHER INFORMATION: chemically synthesized
<221> NAME/KEY: CARBOHYD
<222> LOCATION: (47)..(47)
<223> OTHER INFORMATION: disialo(alpha 2-6) oligosaccharide
<220> FEATURE:
<221> NAME/KEY: CARBOHYD
<222> LOCATION: (75)..(75)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 83

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Cys Gln
        35                  40                  45

Phe Gln Lys Glu Asp Ala Ala Leu Thr Ile Tyr Glu Met Leu Gln Asn
50                  55                  60

Ile Phe Ala Ile Phe Arg Gln Asp Ser Ser Cys Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
130                 135                 140

Val Arg Val Glu Ile Leu Arg Asn Phe Tyr Phe Ile Asn Arg Leu Thr
145                 150                 155                 160

Gly Tyr Leu Arg Asn
            165

<210> SEQ ID NO 84
<211> LENGTH: 165
<212> TYPE: PRT
<213> ORGANISM: Artificial sequence
<220> FEATURE:
<223> OTHER INFORMATION: chemically synthesized
<221> NAME/KEY: CARBOHYD -continued

```
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (75)..(75)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 84

Ser Tyr Asn Leu Leu Gly Phe Leu Gln Arg Ser Ser Asn Phe Gln Ser
 1               5                  10                  15

Gln Lys Leu Leu Trp Gln Leu Asn Gly Arg Leu Glu Tyr Cys Leu Lys
             20                  25                  30

Asp Arg Met Asn Phe Asp Ile Pro Glu Glu Ile Lys Gln Leu Gln Cys
         35                  40                  45

Phe Gln Lys Glu Asp Ala Ala Leu Thr Ile Tyr Glu Met Leu Gln Asn
     50                  55                  60

Ile Phe Ala Ile Phe Arg Gln Asp Ser Ser Cys Thr Gly Trp Cys Glu
 65                  70                  75                  80

Thr Ile Val Glu Asn Leu Leu Ala Asn Val Tyr His Gln Ile Asn His
                 85                  90                  95

Leu Lys Thr Val Leu Glu Glu Lys Leu Glu Cys Glu Asp Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 85
<211> LENGTH: 165
<212> TYPE: PRT
<213> ORGANISM: Artificial sequence
<220> FEATURE:
<223> OTHER INFORMATION: chemically synthesized
<221> NAME/KEY: CARBOHYD
<222> LOCATION: (49)..(49)
<223> OTHER INFORMATION: disialo(alpha 2-6) oligosaccharide
<220> FEATURE:
<221> NAME/KEY: CARBOHYD
<222> LOCATION: (75)..(75)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
```

```
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 85

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Gln
        35                  40                  45

Cys Gln Lys Glu Asp Ala Ala Leu Thr Ile Tyr Glu Met Leu Gln Asn
50                  55                  60

Ile Phe Ala Ile Phe Arg Gln Asp Ser Ser Cys Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 86
<211> LENGTH: 165
<212> TYPE: PRT
<213> ORGANISM: Artificial sequence
<220> FEATURE:
<223> OTHER INFORMATION: chemically synthesized
<221> NAME/KEY: CARBOHYD
<222> LOCATION: (50)..(50)
<223> OTHER INFORMATION: disialo(alpha 2-6) oligosaccharide
<220> FEATURE:
<221> NAME/KEY: CARBOHYD
<222> LOCATION: (75)..(75)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 86

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
```

```
                20                  25                  30

Asp Arg Met Asn Phe Asp Ile Pro Glu Glu Ile Lys Gln Leu Gln Gln
                35                  40                  45

Phe Cys Lys Glu Asp Ala Ala Leu Thr Ile Tyr Glu Met Leu Gln Asn
                50                  55                  60

Ile Phe Ala Ile Phe Arg Gln Asp Ser Ser Thr Gly Trp Cys Glu
 65                  70                  75                  80

Thr Ile Val Glu Asn Leu Leu Ala Asn Val Tyr His Gln Ile Asn His
                    85                  90                  95

Leu Lys Thr Val Leu Glu Glu Lys Leu Glu Cys Glu Asp Phe Thr Arg
                100                 105                 110

Gly Lys Leu Met Ser Ser Leu His Leu Lys Arg Tyr Tyr Gly Arg Ile
                115                 120                 125

Leu His Tyr Leu Lys Ala Lys Cys Tyr Ser His Cys Ala Trp Thr Ile
                130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 87
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (112)..(112)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 87

Ser Tyr Asn Leu Leu Gly Phe Leu Gln Arg Ser Ser Asn Phe Gln Ser
 1               5                  10                  15

Gln Lys Leu Leu Trp Gln Leu Asn Gly Arg Leu Glu Tyr Cys Leu Lys
                20                  25                  30

Asp Arg Met Asn Phe Asp Ile Pro Glu Glu Ile Lys Gln Leu Gln Gln
                35                  40                  45

Phe Gln Lys Glu Asp Ala Ala Leu Thr Ile Tyr Glu Met Leu Gln Asn
                50                  55                  60

Ile Phe Ala Ile Phe Arg Gln Asp Ser Ser Ser Thr Gly Trp Cys Glu
 65                  70                  75                  80

Thr Ile Val Glu Asn Leu Leu Ala Asn Val Tyr His Gln Ile Asn His
                    85                  90                  95

Leu Lys Thr Val Leu Glu Glu Lys Leu Glu Cys Glu Asp Phe Thr Cys
                100                 105                 110
```

```
Gly Lys Leu Met Ser Ser Leu His Leu Lys Arg Tyr Tyr Gly Arg Ile
            115                 120                 125

Leu His Tyr Leu Lys Ala Lys Cys Tyr Ser His Cys Ala Trp Thr Ile
        130                 135                 140

Val Arg Val Glu Ile Leu Arg Asn Phe Tyr Phe Ile Asn Arg Leu Thr
145                 150                 155                 160

Gly Tyr Leu Arg Asn
            165

<210> SEQ ID NO 88
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (28)..(28)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 88

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Cys Tyr Cys Leu Lys
            20                  25                  30

Asp Arg Met Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Arg
            100                 105                 110

Gly Lys Leu Met Ser Ser Leu His Leu Lys Arg Tyr Tyr Gly Arg Ile
            115                 120                 125

Leu His Tyr Leu Lys Ala Lys Cys Tyr Ser His Cys Ala Trp Thr Ile
        130                 135                 140

Val Arg Val Glu Ile Leu Arg Asn Phe Tyr Phe Ile Asn Arg Leu Thr
145                 150                 155                 160

Gly Tyr Leu Arg Asn
            165

<210> SEQ ID NO 89
<211> LENGTH: 165
<212> TYPE: PRT
<213> ORGANISM: Artificial sequence
```

```
<220> FEATURE:
<223> OTHER INFORMATION: chemically synthesized
<220> FEATURE:
<221> NAME/KEY: CARBOHYD
<222> LOCATION: (35)..(35)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 89

Ser Tyr Asn Leu Leu Gly Phe Leu Gln Arg Ser Ser Asn Phe Gln Ser
 1               5                  10                  15

Gln Lys Leu Leu Trp Gln Leu Asn Gly Arg Leu Glu Tyr Cys Leu Lys
            20                  25                  30

Asp Arg Cys Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
 50                  55                  60

Ile Phe Ala Ile Phe Arg Gln Asp Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Arg
           100                 105                 110

Gly Lys Leu Met Ser Ser Leu His Leu Lys Arg Tyr Tyr Gly Arg Ile
       115                 120                 125

Leu His Tyr Leu Lys Ala Lys Cys Tyr Ser His Cys Ala Trp Thr Ile
130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 90
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (70)..(70)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (136)..(136)
```

```
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 90

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Cys Gln Asp Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Cys Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 91
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (75)..(75)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (107)..(107)
<223> OTHER INFORMATION: disialo(alpha 2-6) oligosaccharide
<220> FEATURE:
<221> NAME/KEY: CARBOHYD
<222> LOCATION: (136)..(136)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 91

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
```

```
                50                  55                  60
Ile Phe Ala Ile Phe Arg Gln Asp Ser Ser Cys Thr Gly Trp Cys Glu
 65                  70                  75                  80

Thr Ile Val Glu Asn Leu Leu Ala Asn Val Tyr His Gln Ile Asn His
                 85                  90                  95

Leu Lys Thr Val Leu Glu Glu Lys Leu Glu Cys Glu Asp Phe Thr Arg
                100                 105                 110

Gly Lys Leu Met Ser Ser Leu His Leu Lys Arg Tyr Tyr Gly Arg Ile
                115                 120                 125

Leu His Tyr Leu Lys Ala Lys Cys Tyr Ser His Cys Ala Trp Thr Ile
                130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 92
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-3) oligosaccharide
<220> FEATURE:
<221> NAME/KEY: CARBOHYD
<222> LOCATION: (48)..(48)
<223> OTHER INFORMATION: disialo(alpha 2-3) oligosaccharide
<220> FEATURE:
<221> NAME/KEY: CARBOHYD
<222> LOCATION: (79)..(79)
<223> OTHER INFORMATION: disialo(alpha 2-3) oligosaccharide
<220> FEATURE:
<221> NAME/KEY: CARBOHYD
<222> LOCATION: (107)..(107)
<223> OTHER INFORMATION: disialo(alpha 2-3) oligosaccharide
<220> FEATURE:
<221> NAME/KEY: DISULFID
<222> LOCATION: (30)..(140)

<400> SEQUENCE: 92

Cys Tyr Asn Leu Leu Gly Phe Leu Gln Arg Ser Ser Asn Phe Gln Ser
 1               5                  10                  15

Gln Lys Leu Leu Trp Gln Leu Asn Gly Arg Leu Glu Tyr Cys Leu Lys
                20                  25                  30

Asp Arg Met Asn Phe Asp Ile Pro Glu Glu Ile Lys Gln Leu Gln Cys
                35                  40                  45

Phe Gln Lys Glu Asp Ala Ala Leu Thr Ile Tyr Glu Met Leu Gln Asn
 50                  55                  60

Ile Phe Ala Ile Phe Arg Gln Asp Ser Ser Thr Gly Trp Cys Glu
 65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Arg
                100                 105                 110

Gly Lys Leu Met Ser Ser Leu His Leu Lys Arg Tyr Tyr Gly Arg Ile
                115                 120                 125

Leu His Tyr Leu Lys Ala Lys Glu Tyr Ser His Cys Ala Trp Thr Ile
                130                 135                 140
```

Val Arg Val Glu Ile Leu Arg Asn Phe Tyr Phe Ile Asn Arg Leu Thr
145                 150                 155                 160

Gly Tyr Leu Arg Asn
            165

<210> SEQ ID NO 93
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: monosialo oligosaccharide
<220> FEATURE:
<221> NAME/KEY: CARBOHYD
<222> LOCATION: (48)..(48)
<223> OTHER INFORMATION: monosialo oligosaccharide
<220> FEATURE:
<221> NAME/KEY: CARBOHYD
<222> LOCATION: (79)..(79)
<223> OTHER INFORMATION: monosialo oligosaccharide
<220> FEATURE:
<221> NAME/KEY: CARBOHYD
<222> LOCATION: (107)..(107)
<223> OTHER INFORMATION: monosialo oligosaccharide
<220> FEATURE:
<221> NAME/KEY: CARBOHYD
<222> LOCATION: (112)..(112)
<223> OTHER INFORMATION: monosialo oligosaccharide
<220> FEATURE:
<221> NAME/KEY: CARBOHYD
<222> LOCATION: (123)..(123)
<223> OTHER INFORMATION: monosialo oligosaccharide
<220> FEATURE:
<221> NAME/KEY: DISULFID
<222> LOCATION: (30)..(140)

<400> SEQUENCE: 93

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
            100                 105                 110

Gly Lys Leu Met Ser Ser Leu His Leu Lys Cys Tyr Tyr Gly Arg Ile
        115                 120                 125

Leu His Tyr Leu Lys Ala Lys Glu Tyr Ser His Cys Ala Trp Thr Ile
130                 135                 140

Val Arg Val Glu Ile Leu Arg Asn Phe Tyr Phe Ile Asn Arg Leu Thr
145                 150                 155                 160

Gly Tyr Leu Arg Asn
            165

<210> SEQ ID NO 94
<211> LENGTH: 165

```
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: monosialo oligosaccharide
<220> FEATURE:
<221> NAME/KEY: CARBOHYD
<222> LOCATION: (3)..(3)
<223> OTHER INFORMATION: monosialo oligosaccharide
<220> FEATURE:
<221> NAME/KEY: CARBOHYD
<222> LOCATION: (48)..(48)
<223> OTHER INFORMATION: monosialo oligosaccharide
<220> FEATURE:
<221> NAME/KEY: CARBOHYD
<222> LOCATION: (79)..(79)
<223> OTHER INFORMATION: monosialo oligosaccharide
<220> FEATURE:
<221> NAME/KEY: CARBOHYD
<222> LOCATION: (107)..(107)
<223> OTHER INFORMATION: monosialo oligosaccharide
<220> FEATURE:
<221> NAME/KEY: CARBOHYD
<222> LOCATION: (112)..(112)
<223> OTHER INFORMATION: monosialo oligosaccharide
<220> FEATURE:
<221> NAME/KEY: DISULFID
<222> LOCATION: (30)..(140)

<400> SEQUENCE: 94

Cys Tyr Cys Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
            100                 105                 110

Gly Lys Leu Met Ser Ser Leu His Leu Lys Arg Tyr Tyr Gly Arg Ile
        115                 120                 125

Leu His Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 95
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: monosialo oligosaccharide
<220> FEATURE:
```

```
<221> NAME/KEY: CARBOHYD
<222> LOCATION: (48)..(48)
<223> OTHER INFORMATION: monosialo oligosaccharide
<220> FEATURE:
<221> NAME/KEY: CARBOHYD
<222> LOCATION: (79)..(79)
<223> OTHER INFORMATION: monosialo oligosaccharide
<220> FEATURE:
<221> NAME/KEY: CARBOHYD
<222> LOCATION: (107)..(107)
<223> OTHER INFORMATION: monosialo oligosaccharide
<220> FEATURE:
<221> NAME/KEY: DISULFID
<222> LOCATION: (30)..(140)

<400> SEQUENCE: 95

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 96
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: trisialo(alpha 2-6) oligosaccharide
<220> FEATURE:
<221> NAME/KEY: CARBOHYD
<222> LOCATION: (48)..(48)
<223> OTHER INFORMATION: trisialo(alpha 2-6) oligosaccharide
<220> FEATURE:
<221> NAME/KEY: CARBOHYD
<222> LOCATION: (79)..(79)
<223> OTHER INFORMATION: trisialo(alpha 2-6) oligosaccharide
<220> FEATURE:
<221> NAME/KEY: CARBOHYD
<222> LOCATION: (107)..(107)
<223> OTHER INFORMATION: trisialo(alpha 2-6) oligosaccharide
<220> FEATURE:
<221> NAME/KEY: CARBOHYD
<222> LOCATION: (112)..(112)
<223> OTHER INFORMATION: trisialo(alpha 2-6) oligosaccharide
<220> FEATURE:
<221> NAME/KEY: CARBOHYD
```

```
<222> LOCATION: (123)..(123)
<223> OTHER INFORMATION: trisialo(alpha 2-6) oligosaccharide
<220> FEATURE:
<221> NAME/KEY: DISULFID
<222> LOCATION: (30)..(140)

<400> SEQUENCE: 96

Cys Tyr Asn Leu Leu Gly Phe Leu Gln Arg Ser Ser Asn Phe Gln Ser
 1               5                  10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Cys
            100                 105                 110

Gly Lys Leu Met Ser Ser Leu His Leu Lys Cys Tyr Tyr Gly Arg Ile
        115                 120                 125

Leu His Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 97
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: trisialo(alpha 2-6) oligosaccharide
<220> FEATURE:
<221> NAME/KEY: CARBOHYD
<222> LOCATION: (48)..(48)
<223> OTHER INFORMATION: trisialo(alpha 2-6) oligosaccharide
<220> FEATURE:
<221> NAME/KEY: CARBOHYD
<222> LOCATION: (79)..(79)
<223> OTHER INFORMATION: trisialo(alpha 2-6) oligosaccharide
<220> FEATURE:
<221> NAME/KEY: CARBOHYD
<222> LOCATION: (107)..(107)
<223> OTHER INFORMATION: trisialo(alpha 2-6) oligosaccharide
<220> FEATURE:
<221> NAME/KEY: DISULFID
<222> LOCATION: (30)..(140)

<400> SEQUENCE: 97

Cys Tyr Asn Leu Leu Gly Phe Leu Gln Arg Ser Ser Asn Phe Gln Ser
 1               5                  10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45
```

```
Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Arg
            100                 105                 110

Gly Lys Leu Met Ser Ser Leu His Leu Lys Arg Tyr Tyr Gly Arg Ile
                115                 120                 125

Leu His Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 98
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: tetrasialo(alpha 2-6) oligosaccharide
<220> FEATURE:
<221> NAME/KEY: CARBOHYD
<222> LOCATION: (48)..(48)
<223> OTHER INFORMATION: tetrasialo(alpha 2-6) oligosaccharide
<220> FEATURE:
<221> NAME/KEY: CARBOHYD
<222> LOCATION: (79)..(79)
<223> OTHER INFORMATION: tetrasialo(alpha 2-6) oligosaccharide
<220> FEATURE:
<221> NAME/KEY: CARBOHYD
<222> LOCATION: (107)..(107)
<223> OTHER INFORMATION: tetrasialo(alpha 2-6) oligosaccharide
<220> FEATURE:
<221> NAME/KEY: CARBOHYD
<222> LOCATION: (112)..(112)
<223> OTHER INFORMATION: tetrasialo(alpha 2-6) oligosaccharide
<220> FEATURE:
<221> NAME/KEY: CARBOHYD
<222> LOCATION: (123)..(123)
<223> OTHER INFORMATION: tetrasialo(alpha 2-6) oligosaccharide
<220> FEATURE:
<221> NAME/KEY: DISULFID
<222> LOCATION: (30)..(140)

<400> SEQUENCE: 98

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95
```

```
Leu Lys Thr Val Leu Glu Glu Lys Leu Glu Cys Glu Asp Phe Thr Cys
            100                 105                 110

Gly Lys Leu Met Ser Ser Leu His Leu Lys Cys Tyr Tyr Gly Arg Ile
        115                 120                 125

Leu His Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 99
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: tetrasialo(alpha 2-6) oligosaccharide
<220> FEATURE:
<221> NAME/KEY: CARBOHYD
<222> LOCATION: (48)..(48)
<223> OTHER INFORMATION: tetrasialo(alpha 2-6) oligosaccharide
<220> FEATURE:
<221> NAME/KEY: CARBOHYD
<222> LOCATION: (79)..(79)
<223> OTHER INFORMATION: tetrasialo(alpha 2-6) oligosaccharide
<220> FEATURE:
<221> NAME/KEY: CARBOHYD
<222> LOCATION: (107)..(107)
<223> OTHER INFORMATION: tetrasialo(alpha 2-6) oligosaccharide
<220> FEATURE:
<221> NAME/KEY: DISULFID
<222> LOCATION: (30)..(140)

<400> SEQUENCE: 99

Cys Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Cys Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Cys Glu Asp Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 100
```

```
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide
<220> FEATURE:
<221> NAME/KEY: CARBOHYD
<222> LOCATION: (26)..(26)
<223> OTHER INFORMATION: disialo(alpha 2-6) oligosaccharide
<220> FEATURE:
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (67)..(67)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (88)..(88)
<223> OTHER INFORMATION: disialo(alpha 2-6) oligosaccharide
<220> FEATURE:
<221> NAME/KEY: DISULFID
<222> LOCATION: (30)..(140)

<400> SEQUENCE: 100

Cys Tyr Asn Leu Leu Gly Phe Leu Gln Arg Ser Ser Asn Phe Gln Ser
1               5                   10                  15

Gln Lys Leu Leu Trp Gln Leu Asn Gly Cys Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Cys Ile Phe Arg Gln Asp Ser Ser Ser Thr Gly Trp Asn Glu
65                  70                  75                  80

Thr Ile Val Glu Asn Leu Leu Cys Asn Val Tyr His Gln Ile Asn His
                85                  90                  95

Leu Lys Thr Val Leu Glu Glu Lys Leu Glu Lys Glu Asp Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 101
<211> LENGTH: 25
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 1C has Thiazolidine gourp
```

```
<220> FEATURE:
<221> NAME/KEY: BINDING
<222> LOCATION: (25)..(25)
<223> OTHER INFORMATION: alkylthioester-modified with Thiophenol

<400> SEQUENCE: 101

Cys Tyr Asn Leu Leu Gly Phe Leu Gln Arg Ser Ser Asn Phe Gln Ser
1               5                   10                  15

Gln Lys Leu Leu Trp Gln Leu Asn Gly
            20                  25

<210> SEQ ID NO 102
<211> LENGTH: 22
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (5)..(5)
<223> OTHER INFORMATION: Acm
<220> FEATURE:
<221> NAME/KEY: BINDING
<222> LOCATION: (22)..(22)
<223> OTHER INFORMATION: alkylthioester-modified with MESNA

<400> SEQUENCE: 102

Cys Leu Glu Tyr Cys Leu Lys Asp Arg Met Asn Phe Asp Ile Pro Glu
1               5                   10                  15

Glu Ile Lys Gln Leu Gln
            20

<210> SEQ ID NO 103
<211> LENGTH: 19
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 1C has Thiazolidine gourp
<220> FEATURE:
<221> NAME/KEY: BINDING
<222> LOCATION: (19)..(19)
<223> OTHER INFORMATION: alkylthioester-modified with Ethanthiol

<400> SEQUENCE: 103

Cys Phe Gln Lys Glu Asp Ala Ala Leu Thr Ile Tyr Glu Met Leu Gln
1               5                   10                  15
Asn Ile Phe

<210> SEQ ID NO 104
<211> LENGTH: 21
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 1C has Thiazolidine gourp
<220> FEATURE:
<221> NAME/KEY: CARBOHYD
<222> LOCATION: (13)..(13)
<223> OTHER INFORMATION: disialo(alpha 2-6) oligosaccharide
<220> FEATURE:
<221> NAME/KEY: BINDING
<222> LOCATION: (21)..(21)
<223> OTHER INFORMATION: alkylthioester-modified with Thiophenol
<400> SEQUENCE: 104
Cys Ile Phe Arg Gln Asp Ser Ser Ser Thr Gly Trp Asn Glu Thr Ile
1               5                   10                  15
```

Val Glu Asn Leu Leu
            20

<210> SEQ ID NO 105
<211> LENGTH: 78
<212> TYPE: PRT
<213> ORGANISM: Artificial sequence
<220> FEATURE:
<223> OTHER INFORMATION: chemically synthesized
<220> FEATURE:
<221> NAME/KEY: BINDING
<222> LOCATION: (53)..(53)
<223> OTHER INFORMATION: Acm

<400> SEQUENCE: 105

Cys Asn Val Tyr His Gln Ile Asn His Leu Lys Thr Val Leu Glu Glu
1               5                   10                  15

Lys Leu Glu Lys Glu Asp Phe Thr Arg Gly Lys Leu Met Ser Ser Leu
            20                  25                  30

His Leu Lys Arg Tyr Tyr Gly Arg Ile Leu His Tyr Leu Lys Ala Lys
        35                  40                  45

Glu Tyr Ser His Cys Ala Trp Thr Ile Val Arg Val Glu Ile Leu Arg
    50                  55                  60

Asn Phe Tyr Phe Ile Asn Arg Leu Thr Gly Tyr Leu Arg Asn
65                  70                  75

<210> SEQ ID NO 106
<211> LENGTH: 47
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 1C has Thiazolidine gourp
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (47)..(47)
<223> OTHER INFORMATION: alkylthioester-modified with Ethanthiol

<400> SEQUENCE: 106

Cys Tyr Asn Leu Leu Gly Phe Leu Gln Arg Ser Ser Asn Phe Gln Ser
1               5                   10                  15

Gln Lys Leu Leu Trp Gln Leu Asn Gly Cys Leu Glu Tyr Cys Leu Lys
            20                  25                  30

Asp Arg Met Asn Phe Asp Ile Pro Glu Glu Ile Lys Gln Leu Gln
        35                  40                  45

<210> SEQ ID NO 107
<211> LENGTH: 99
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (13)..(13)
<223> OTHER INFORMATION: disialo(alpha 2-6) oligosaccharide
<220> FEATURE:
<221> NAME/KEY: BINDING
<222> LOCATION: (74)..(74)
<223> OTHER INFORMATION: Acm

<400> SEQUENCE: 107

```
Cys Ile Phe Arg Gln Asp Ser Ser Ser Thr Gly Trp Asn Glu Thr Ile
1               5                   10                  15

Val Glu Asn Leu Leu Cys Asn Val Tyr His Gln Ile Asn His Leu Lys
            20                  25                  30

Thr Val Leu Glu Glu Lys Leu Glu Lys Glu Asp Phe Thr Arg Gly Lys
        35                  40                  45

Leu Met Ser Ser Leu His Leu Lys Arg Tyr Tyr Gly Arg Ile Leu His
    50                  55                  60

Tyr Leu Lys Ala Lys Glu Tyr Ser His Cys Ala Trp Thr Ile Val Arg
65                  70                  75                  80

Val Glu Ile Leu Arg Asn Phe Tyr Phe Ile Asn Arg Leu Thr Gly Tyr
                85                  90                  95

Leu Arg Asn

<210> SEQ ID NO 108
<211> LENGTH: 118
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (32)..(32)
<223> OTHER INFORMATION: disialo(alpha 2-6) oligosaccharide
<220> FEATURE:
<221> NAME/KEY: BINDING
<222> LOCATION: (93)..(93)
<223> OTHER INFORMATION: Acm

<400> SEQUENCE: 108

Cys Phe Gln Lys Glu Asp Ala Ala Leu Thr Ile Tyr Glu Met Leu Gln
1               5                   10                  15

Asn Ile Phe Cys Ile Phe Arg Gln Asp Ser Ser Ser Thr Gly Trp Asn
            20                  25                  30

Glu Thr Ile Val Glu Asn Leu Leu Cys Asn Val Tyr His Gln Ile Asn
        35                  40                  45

His Leu Lys Thr Val Leu Glu Glu Lys Leu Glu Lys Glu Asp Phe Thr
    50                  55                  60

Arg Gly Lys Leu Met Ser Ser Leu His Leu Lys Arg Tyr Tyr Gly Arg
65                  70                  75                  80

Ile Leu His Tyr Leu Lys Ala Lys Glu Tyr Ser His Cys Ala Trp Thr
                85                  90                  95

Ile Val Arg Val Glu Ile Leu Arg Asn Phe Tyr Phe Ile Asn Arg Leu
            100                 105                 110

Thr Gly Tyr Leu Arg Asn
        115

<210> SEQ ID NO 109
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: BINDING
<222> LOCATION: (30)..(30)
<223> OTHER INFORMATION: Acm
<220> FEATURE:
<221> NAME/KEY: BINDING
```

```
<222> LOCATION: (140)..(140)
<223> OTHER INFORMATION: Acm

<400> SEQUENCE: 109

Cys Tyr Asn Leu Leu Gly Phe Leu Gln Arg Ser Ser Asn Phe Gln Ser
1               5                   10                  15

Gln Lys Leu Leu Trp Gln Leu Asn Gly Cys Leu Glu Tyr Cys Leu Lys
            20                  25                  30

Asp Arg Met Asn Phe Asp Ile Pro Glu Glu Ile Lys Gln Leu Gln Cys
        35                  40                  45

Phe Gln Lys Glu Asp Ala Ala Leu Thr Ile Tyr Glu Met Leu Gln Asn
    50                  55                  60

Ile Phe Cys Ile Phe Arg Gln Asp Ser Ser Ser Thr Gly Trp Asn Glu
65                  70                  75                  80

Thr Ile Val Glu Asn Leu Leu Cys Asn Val Tyr His Gln Ile Asn His
                85                  90                  95

Leu Lys Thr Val Leu Glu Glu Lys Leu Glu Lys Glu Asp Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 110
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide
<220> FEATURE:
<221> NAME/KEY: CARBOHYD
<222> LOCATION: (26)..(26)
<223> OTHER INFORMATION: disialo(alpha 2-6) oligosaccharide
<220> FEATURE:
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (67)..(67)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (88)..(88)
<223> OTHER INFORMATION: disialo(alpha 2-6) oligosaccharide
<220> FEATURE:
<221> NAME/KEY: BINDING
<222> LOCATION: (30)..(30)
<223> OTHER INFORMATION: Acm
<220> FEATURE:
<221> NAME/KEY: BINDING
<222> LOCATION: (140)..(140)
<223> OTHER INFORMATION: Acm

<400> SEQUENCE: 110
```

```
Cys Tyr Asn Leu Leu Gly Phe Leu Gln Arg Ser Ser Asn Phe Gln Ser
1               5                   10                  15

Gln Lys Leu Leu Trp Gln Leu Asn Gly Cys Leu Glu Tyr Cys Leu Lys
            20                  25                  30

Asp Arg Met Asn Phe Asp Ile Pro Glu Glu Ile Lys Gln Leu Gln Cys
                35                  40                  45

Phe Gln Lys Glu Asp Ala Ala Leu Thr Ile Tyr Glu Met Leu Gln Asn
        50                  55                  60

Ile Phe Cys Ile Phe Arg Gln Asp Ser Ser Thr Gly Trp Asn Glu
65                  70                  75                  80

Thr Ile Val Glu Asn Leu Leu Cys Asn Val Tyr His Gln Ile Asn His
                85                  90                  95

Leu Lys Thr Val Leu Glu Glu Lys Leu Glu Lys Glu Asp Phe Thr Arg
            100                 105                 110

Gly Lys Leu Met Ser Ser Leu His Leu Lys Arg Tyr Tyr Gly Arg Ile
            115                 120                 125

Leu His Tyr Leu Lys Ala Lys Glu Tyr Ser His Cys Ala Trp Thr Ile
        130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 111
<211> LENGTH: 165
<212> TYPE: PRT
<213> ORGANISM: Artificial sequence
<220> FEATURE:
<223> OTHER INFORMATION: chemically synthesized
<220> FEATURE:
<221> NAME/KEY: CARBOHYD
<222> LOCATION: (1)..(1)
<223> OTHER INFORMATION: disialo(alpha 2-6) oligosaccharide
<220> FEATURE:
<221> NAME/KEY: CARBOHYD
<222> LOCATION: (26)..(26)
<223> OTHER INFORMATION: disialo(alpha 2-6) oligosaccharide
<220> FEATURE:
<221> NAME/KEY: CARBOHYD
<222> LOCATION: (48)..(48)
<223> OTHER INFORMATION: disialo(alpha 2-6) oligosaccharide
<220> FEATURE:
<221> NAME/KEY: CARBOHYD
<222> LOCATION: (67)..(67)
<223> OTHER INFORMATION: disialo(alpha 2-6) oligosaccharide
<220> FEATURE:
<221> NAME/KEY: CARBOHYD
<222> LOCATION: (79)..(79)
<223> OTHER INFORMATION: disialo(alpha 2-6) oligosaccharide
<220> FEATURE:
<221> NAME/KEY: CARBOHYD
<222> LOCATION: (88)..(88)
<223> OTHER INFORMATION: disialo(alpha 2-6) oligosaccharide

<400> SEQUENCE: 111

Cys Tyr Asn Leu Leu Gly Phe Leu Gln Arg Ser Ser Asn Phe Gln Ser
1               5                   10                  15

Gln Lys Leu Leu Trp Gln Leu Asn Gly Cys Leu Glu Tyr Cys Leu Lys
            20                  25                  30

Asp Arg Met Asn Phe Asp Ile Pro Glu Glu Ile Lys Gln Leu Gln Cys
                35                  40                  45

Phe Gln Lys Glu Asp Ala Ala Leu Thr Ile Tyr Glu Met Leu Gln Asn
        50                  55                  60
```

```
Ile Phe Cys Ile Phe Arg Gln Asp Ser Ser Ser Thr Gly Trp Asn Glu
65                  70                  75                  80

Thr Ile Val Glu Asn Leu Leu Cys Asn Val Tyr His Gln Ile Asn His
                85                  90                  95

Leu Lys Thr Val Leu Glu Glu Lys Leu Glu Lys Glu Asp Phe Thr Arg
            100                 105                 110

Gly Lys Leu Met Ser Ser Leu His Leu Lys Arg Tyr Tyr Gly Arg Ile
            115                 120                 125

Leu His Tyr Leu Lys Ala Lys Glu Tyr Ser His Cys Ala Trp Thr Ile
        130                 135                 140

Val Arg Val Glu Ile Leu Arg Asn Phe Tyr Phe Ile Asn Arg Leu Thr
145                 150                 155                 160

Gly Tyr Leu Arg Asn
                165
```